(12) United States Patent
Rajaraman et al.

(10) Patent No.: US 11,840,446 B2
(45) Date of Patent: Dec. 12, 2023

(54) FABRICATION OF 3D MICROELECTRODES AND USE THEREOF IN MULTI-FUNCTIONAL BIOSYSTEMS

(71) Applicant: UNIVERSITY OF CENTRAL FLORIDA RESEARCH FOUNDATION, INC., Orlando, FL (US)

(72) Inventors: Swaminathan Rajaraman, Orlando, FL (US); Charles Didier, Orlando, FL (US); Avra Kundu, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 367 days.

(21) Appl. No.: 16/908,666

(22) Filed: Jun. 22, 2020

(65) Prior Publication Data
US 2021/0024351 A1    Jan. 28, 2021

Related U.S. Application Data

(60) Provisional application No. 62/864,844, filed on Jun. 21, 2019.

(51) Int. Cl.
*B81C 1/00*   (2006.01)
*B81B 1/00*   (2006.01)
*C12M 1/34*   (2006.01)
*G01N 33/50*  (2006.01)

(52) U.S. Cl.
CPC .......... *B81C 1/00111* (2013.01); *B81B 1/008* (2013.01); *C12M 41/46* (2013.01); *G01N 33/5082* (2013.01); *B81B 2201/055* (2013.01); *B81C 2201/0146* (2013.01)

(58) Field of Classification Search
CPC ........................... B81C 1/00111; B81B 1/008
See application file for complete search history.

(56) References Cited

U.S. PATENT DOCUMENTS

| 2006/0202385 A1* | 9/2006 | Xu .................. B81C 1/00111 425/542 |
| 2009/0318833 A1* | 12/2009 | Lim ...................... A61M 5/329 264/220 |
| 2012/0085652 A1* | 4/2012 | Omanovic ............... C25D 9/02 205/235 |
| 2019/0046479 A1* | 2/2019 | Pathak ................. A61K 9/1641 |
| 2021/0033559 A1* | 2/2021 | Panat .................... H05K 3/125 |

OTHER PUBLICATIONS

FormLabs, Material Data sheet dated Sep. 13, 2018, Rev 06 1/22/22/2019; 1-7 pages.*

(Continued)

*Primary Examiner* — Moazzam Hossain
(74) *Attorney, Agent, or Firm* — Timothy H. Van Dyke; WOLTER, VAN DYKE, DAVIS, PLLC

(57) ABSTRACT

Disclosed herein is a microelectrode platform that may be used for multiple biosystem applications including cell culturing techniques and biosensing. Also disclosed are microfabrication techniques for inexpensively producing microelectrode platforms.

14 Claims, 52 Drawing Sheets

(56) References Cited

OTHER PUBLICATIONS

Kundu, Avra et al., Precision Vascular Delivery of Agrochemicals with Micromlled Microneedles (uMMNs), Scientific Reports, 2019, 8 pages.
Kundu, Avra et al., "3D Printing, Ink Casting and Micromachined Lamination (3D PICLuM): A Makerspace Approach to the Fabrication of Biological Microdevices", Micromachines, 2018, 23 pages.
Kundu, Avra et al., "Optimizatoin of makerspace microfabrication techniques and materials for the realization of planar, 3D printed microelectrode arrays in under four days", Royal Society of Chemistry, 2019, vol. 9, pp. 8949-8963.
Lacava, P.T. et al, "Interaction between endophytic bacteria from citrus plants and the phytopathogenic bacteria Xylella fastidiosa, causal agent of citrus-variegated chlorosis", Letters in Applied Microbiology, 2004, vol. 39, pp. 55-59.
Pimentel, David, "Amounts of Pesticides Reaching Target Pests: Environmental Impacts and Ethics", 1995, vol. 8, Issue 1, pp. 17-29.
Popov, K. et al., "New tool-workpiece setting up technology for micro-milling", Int. J. Adv. Manuf Technol, 2010, vol. 47, pp. 21-27.
Technical Resources, "Radial Chip Thinning", 2017, 2 pages.
Shamshiri, Redmond Ramin et al., "Research and development in agricultural robotics: A perspective of digital farming", Int. J. Agric & Biol Eng., Jul. 2018, vol. 11, No. 4, 14 pages.
Shatla, M. et al., "Analytical modeling of drilling and ball end milling", Journal of Materials Processing Technology, 2000, vol. 98, pp. 125-133.
Van Der Maaden, Koen et al., "Microneedle technologies for (trans)dermal drug and vaccine delivery", Journal of Controlled Release, 2012, vol. 161, pp. 645-655.
Walsh III, David I et al., "Enabling Microfluidics: from Clean Rooms to Makerspaces", Trends in Biotechnology, May 2017, vol. 35, No. 5, pp. 383-392.
Covino, B.S. et al., "Dissolution Behavior of 304 Stainless Steel in HNO3/HF Mixtures", Metallurgical Transactions A, Jan. 1986, vol. 17A, 13 pages.
Diaz, Nancy et al., "Energy Consumption Characterization and Reduction Strategies for Milling Machine Tool Use", Glocalized Solutions for Sustainability in Manufacturing: Proceedings of the 18th CIRP International 263 Conference on Life Cycle Engineering, Technische Universität Braunschweig, Braunschweig, Germany, May 2-4, 2011,5 pages.
Didier, Charles M. et al., "Facile, Packaging Substrate-Agnostic, Microfabrication and Assembly of Scalable 3D Metal Microelectrode Arrays for in Vitro Organ-On-A-Chip and Cellular Disease Modeling", Transducers 2019—Eurosensors XXXIII, Berlin, Germany, Jun. 23-27, 2019, 4 pages.
Dweiri, F. et al., "Fuzzy surface roughness modeling of CNC down milling of Alumic-79", Journal of Material Processing Technology, 2003, vol. 133, pp. 266-275.
Epa, "Flame Atomic Absorption Spectrophotometry", Feb. 2007, Revision 2, 23 pages.
Erner, Yair et al., "Morphology and Anatomy of Stems and Pedicels of Spring Flush Shoots Associated with Citrus Fruit Set", Annals of Botany, 1996, vol. 77, pp. 537-545.
Formlabs, "Materials Data Sheet", 7 pages, Dated Sep. 13, 2018; Rev 06 Jan. 22, 2019.
Gardner et al., "Biological Control of Plant Pathogens: Research, Commercialization, and Application in the USA", Plant Health Progress, May 10, 2002, 15 pages.
Jagoueix, Sandrine et al., "The Phloem-Limited Bacterium of Greening Disease of Citrus Is a Member of the a Subdivision of the Proteobacteria", International Journal of Systematic Bacteriology, Jul. 1994, vol. 44, No. 3, pp. 379-386.
Johnson, E.G., "Zinkicide a Nanotherapeutic for HLB", Oct. 9, 2020, https://portal.nifa.usda.gov/web/crisprojectpages/1005557-zinkicide-a-nanotherapeutic-for-hlb.html, 15 pages.
Jyung, W.H. et al., "Foliar Absorption—An Active Uptake Process", Amer. Jour Bot, 1964, vol. 51 No. 4, pp. 437-444.

* cited by examiner

| Ablation Stages | Impedance (Real in Ohms) Frequency (Hz) | | | Phase (-Degrees) | | |
|---|---|---|---|---|---|---|
| | 100Hz | 1kHz | 10kHz | 100Hz | 1kHz | 10kHz |
| Insulated Steel | High MOhms | High MOhms | High MOhms | -38.9° | -3.45° | -97.0° |
| Initial Ablation | 137.6 MOhms | 33.05 MOhms | 0.303 MOhms | -4.49° | -63.0° | -87.8° |
| 70μm Electrode | 87.05 kOhms | 45.50 kOhms | 11.12 kOhms | -17.0° | -34.6° | -41.2° |

FIG. 19

FABRICATION OF 3D MICROELECTRODES AND USE THEREOF IN MULTI-FUNCTIONAL BIOSYSTEMS

BACKGROUND

With the recent introduction of makerspace microfabrication technologies, additive microengineering in combination with suitable toolbox technologies can present rapid and novel solutions for the "Organs-on-a-chip" and cellular disease modeling fields. For these biological applications, one such toolbox, metal microfabrication, remains an underexplored technology for fabrication of 3D microelectrode arrays (MEAs). Selective Laser Sintering and Electron Discharge Machining have been utilized recently to develop 3D MEAs, however brittleness (former) and the necessary complex, non-repeatable packaging steps (latter) remain disadvantages of these approaches. Other technologies involve either metal coatings on polymer composites (example: SU-8) to achieve high aspect-ratio conductive 3D structures, or complex manipulation (example using Dielectrophoresis) of liquid metals (EGaIn) to achieve 2.5D electrodes that are not suitable for arbitrary 3D cell culture architectures. Additionally, both of these techniques cannot achieve conductivity approaching bulk metal.

Also, in recent years there has been a gradual transformation in the micromachining of biological microdevices such as microneedles. Traditional cleanroom-based microfabrication approaches are being replaced by non-conventional techniques outside the cleanroom which allows for the use of a different tool-set while offering a much larger material palette along with rapid fabrication timeframes, design modifications on-the-fly, cost effective, and scalable fabrication. The concept and demonstrated the use of 'Makerspace Microfabrication' has been previously disclosed [Kundu, A., Ausaf, T. & Rajaraman, S. 3D Printing, Ink Casting and Micromachined Lamination (3D PICLμM): A Makerspace Approach to the Fabrication of Biological Microdevices. *Micromachines* 9, 85 (2018); Kundu, A. et al. Optimization of makerspace microfabrication techniques and materials for the realization of planar, 3D printed microelectrode arrays in under four days. *RSC Adv.* 9, 8949-8963 (2019)] for fabricating MNs deployed in transdermal drug delivery applications. These MNs were fabricated using micro-stereo lithography (μSLA), an additive manufacturing technique. Such MNs are appropriate for penetrating soft tissue like skin having an Ultimate Tensile Strength (UTS) of ~40 MPa 13 since commercially available 3D printed materials can have an UTS only as high as 65 MPa 15,16. However, for penetrating trees, the UTS of the material used in MN fabrication needs to be an order of magnitude higher (~500 MPa).

BRIEF DESCRIPTION OF DRAWINGS

These and other features, aspects, and advantages of the present disclosure will become better understood with reference to the following description and appended claims where:

FIG. 19: Table of the associated device impedance and phase values, before insulation, and during the in-situ recorded stages.

GENERAL TERMS

Figure 1:
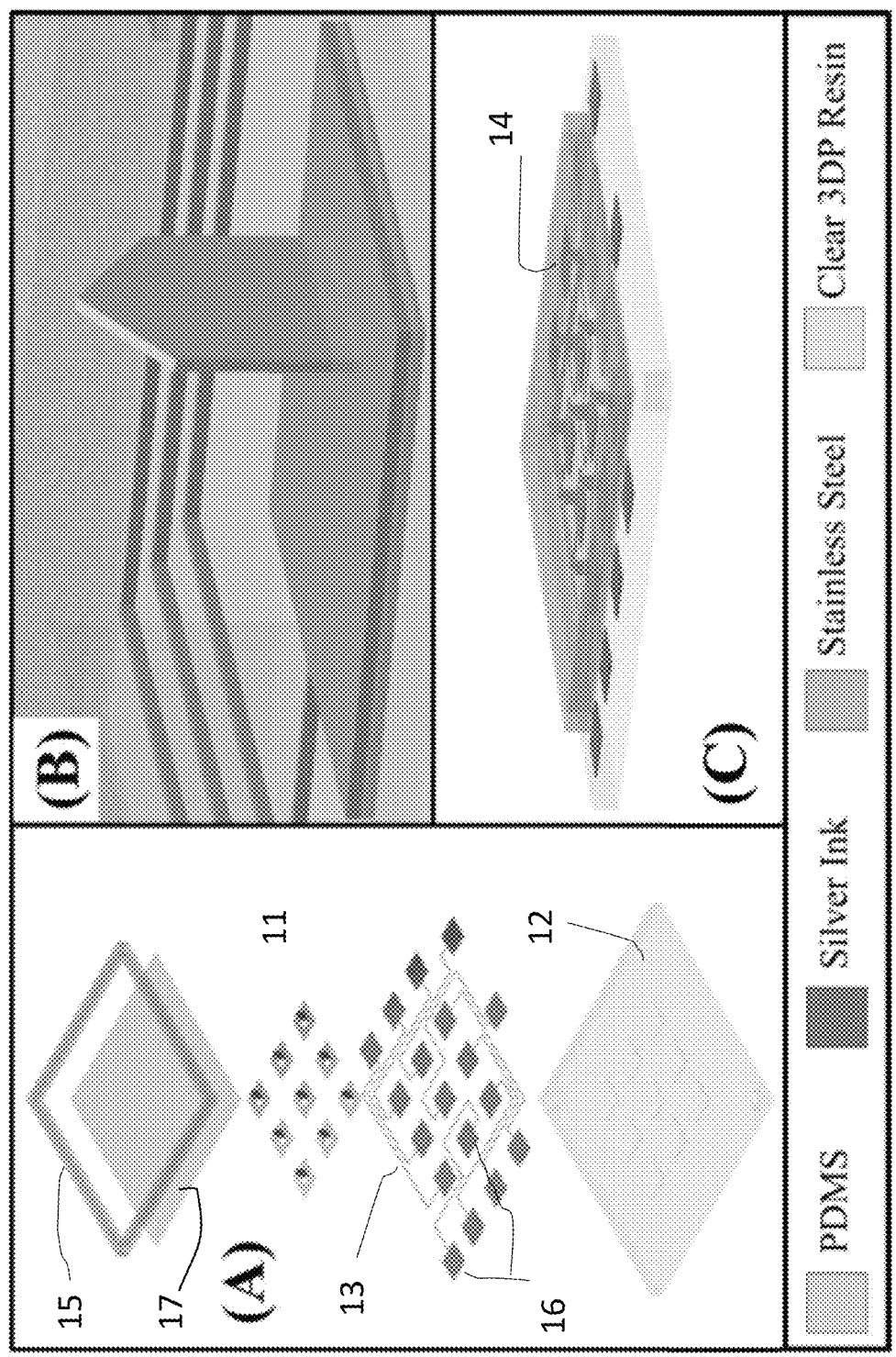
FIG. 1: Process flow for the development, assembly and characterization of the iteration 1 in vitro MEA platform. (A) Exploded schematic of the device, showing the 3D printed substrate, traces, electrode needles, insulation and culture well. (B) Close up of the assembled schematic, centered on the exposed electrode tip. (C) Overview of the assembled schematic.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has", "with," or variants thereof are used in either the detailed description and/or the claims, such terms are intended to be inclusive in a manner similar to the term "comprising."

The term "about" or "approximately" is meant to denote up to a 5, 6, 7, 8, 9, or 10 percent variance in the stated value or range. For example, about 2 includes values of 1.9 to 2.1.

The term "microscale" is meant to denote a size of from 1-1000 micrometers.

Unless specifically indicated, the microneedle array (MEA) or micromilled microneedles (MMN) may refer to the same structures. However, the purpose for which the structures are implemented typically dictates the designation of MEA or MNN. For example, MNN is typically the term used when the structures are implemented to penetrate tissue, such as plant tissue. MEA is typically the term used when the structures are used to deliver or sense electrical signals or interface with tissues such as neural tissue or muscle. Electrical signals may include voltage, current, and/or impedance.

DETAILED DESCRIPTION

Microfabricated electrode structures or microneedles are traditionally machined in 2D, and necessitate the transition to 3D for more complex tissue innervation. To facilitate this out-of-plane transfer to the final 3D conformation, a custom fabricated Hypodermic Needle Array (Hypo-Rig) was created. 3D printing provided the base for the structure, and 30G hypodermic needles created the defined transitioning array. The resulting Hypo-Rig array was successfully able to batch transition steel MEA arrays and micromilled microneedle arrays from 1×2 to 19×20 conformation in 2D to a tight, near-vertical grouping in 3D in a single step.

One embodiment pertains to the Hypo-Rig itself. Such a device can be used as a standalone hollow mesoneedle or microneedle array for drug delivery applications.

Basic force and angular transitions were characterized to assess the effectiveness of the $1^{st}$ generation Hypo-Rig device.

Embodiments disclosed herein also include a novel microelectrode or microneedle platform that has numerous important applications such as:
  Delivery of agrochemicals to plants
  Lab-on-a-chip applications
  Disease modeling applications
  Neuropharmacological testing
  Cardiotoxicity assessment
  Pre-clinical drug discovery
  High throughput phenotypic screening of drug candidates The microelectrode platforms described herein may not only be useful as a sensing (recording) and stimulation platform, but also a drug/therapeutic delivery system. The additional functionality of drug loaded nanofibers has made it possible for microelectrode platforms to simultaneously release molecules and act as a sensor, rendering the disclosed embodiments versatile and applicable in a large range of markets.

Also disclosed herein are novel fabrication methods for 3D microelectrode platforms that are fully functional for 3D cell culture applications.

The microfabrication system disclosed herein is simple in its design, and can be scaled appropriately for larger and customizable array configurations. The components of the device (printing resin, epoxy and hypodermic needles) are inexpensive and materials costs for the production of a single array in high volume is expected to be very affordable. The efficiency of the Rig's design, is far superior to the hand transitioning method which is traditionally used to transition 2D structures to 3D. Consistency in needle spread is also an advantage, which allows for more repeatable manufacturing.

Cell culture MEA fabrication, in addition to the inherent structures native to the Hypo-Rig itself. The Hypo-Rig can be used as a standalone 3D MEA or a hollow mesoneedle array for drug delivery application. These structures being the 3D designed and printed components, as well as the hollow needle, could lend itself to be used for an integrated microfluidic and inherent microelectrode array design. The device as it is fabricated now, can be used on a variety of materials and any number of configurations that could be necessary for a wider range of applications.

The Hypo-Rig expands on the batch fabrication process which is vital to a consistent device fabrication setting. The Rig eliminates the variability in 2D to 3D device/structure transitioning at the meso and microscales, and complements existing microfabrication and assembly techniques such as laser micromachining and micromilling that are currently in use for makerspace microfabrication spaces.

As noted above in the Background, microneedles were fabricated using micro-stereo lithography (μSLA), but the strength of the materials is not particularly suitable for penetrating plants and trees. The use of materials such as stainless steel (SS) or other materials with similar tensile strengths (UTS of ~500 MPa) provide a stronger enough material for penetrating plants and trees. SS based MNs can be fabricated using micromilling which is a subtractive manufacturing method that creates microscale features utilizing microscale cutting tools to remove unwanted bulk material to define the desired geometry. The microscale cutting tools vary in diameter from 5 to 400 μm and have edge radii that vary from 1 to 10 μm.

Overview

In vitro cell culture studies are absolutely essential in biological studies, as they create a controlled environment for accurate measurement and observation of cell populations. Extensions of these cultures include "on-a-chip" platforms, with "organ-on-a-chip" and "body-on-a-chip" models being highly sought after. Enhanced complexity of these models enables increased accuracy in the physiological system these can represent and approach in vivo like metrics. As the complexity of models increase to represent organs or multiple organs, the study of and integration of electrogenic cells becomes more and more paramount. These cells are often the regulatory cells, and pacemaker cells which play an important role in human physiology.

Microelectrode Arrays (MEAs) are then necessary to integrate into these culturing conditions not just for electrical interfacing (i.e., stimulation and recording), but then to study the downstream effects of these electrogenic cells on the organ model as a whole. These emerging markets of benchtop "organs-on-achip" and disease modeling assays require advanced and rapidly microfabricated analytical tools to interrogate the cell culture system and extract physiologically relevant metrics. While several of these biological systems (e.g. lung and liver) can be addressed with planar microsensors and microfluidics, unique electrogenic cell architectures, such as the nervous system, necessitate 3D electrical and optical probing to interface with an organoid, spheroid or microfabricated 3D culture systems. To meet the requirements of this rapidly expanding field, customized microfabrication and packaging strategies are desired to develop analytical tools for electrical interfacing with 3D cell constructs including microelectrodes. This chapter will describe the design, fabrication and characterization of a Makerspace enabled 3D MEA platform, centered on 3D printing, and an underutilized technique: metal microfabrication.

3D MEAs have traditionally been fabricated with glass, silicon or polymer fabrication typically involving chip fabrication and separate packaging steps to be presented in truly 3D form factors. Integrated, monolithically developed 3D MEAs remain rare due to multiple, and often competing microfabrication and packaging requirements, resulting in long time-cycles from design to a developed device. With the recent introduction of makerspace microfabrication technologies, additive microengineering in combination with suitable toolbox technologies can present rapid, customized and novel solutions for the "Organ-on-a-chip" and cellular disease modeling fields. For these biological applications, one such toolbox, metal microfabrication, remains an underexplored technology for fabrication of 3D MEAs. Selective Laser Sintering (SLS) and Electron Discharge Machining (EDM) have been utilized recently to develop 3D MEAs, however brittleness (former) and the necessary complex, non-repeatable packaging steps (latter) remain disadvantages of these approaches. Other technologies involve either metal coatings on polymer composites (example: SU8) to achieve high aspect-ratio conductive 3D structures, or complex manipulation (such as Dielectrophoresis) of liquid metals such as Eutectic GalliumIndium (EGaIn) to achieve 2.5D electrodes that are not suitable for arbitrary 3D cell culture architectures. Additionally, both of these techniques cannot achieve conductivity approaching bulk metal.

As discussed above, many of the metal microfabrication techniques such as SLS and EDM, while still underexplored, are coupled with disadvantages that cannot be overlooked. SLS involves the creation of a structure by sintering of a bed of material. Brittleness aside, SLS with metals leads to a rough and uneven surface, and with polymers, leads to shrinkage, or thermal distortion of the materials. EDM has issues in resolving sharp features and is a very time-consuming process. For better makerspace enabled microfabrication, neither of these metal microfabrication techniques are ideal, as rapid prototyping and simpler post-processing steps are preferred. Disclosed herein an improved metal microfabrication method that involves multimodal selective laser micromachining used in combination with SLA and DLP 3D printing, electrodeposition, and a custom 2D to 3D transitionary fabrication method (see Examples section infra), to fabricate a novel makerspace-enabled 3D MEA culturing platform to interrogate electrogenic cell cultures. One of the big benefits imparted from this work, is the ability to have rapid iterative prototypes. These iterations evolved over successive designs to an intricate, repeatable, modular 3D MEA design, which is completely makerspace enabled.

Description of Exemplary Embodiments

According to one embodiment, provided is a method of fabricating micromilled microneedles from a planar substrate. The method involves micromilling a plurality of cut-outs onto the planar substrate; and transitioning material at the plurality of cut-outs such that the material extends orthogonal to the planar sheet. Micromilling is typically conducted with a laser, though necessarily. The planar substrate is typically metal such as stainless steel. In specific embodiments, the microneedles are transitioned out of plane with the planar substrate such that they form at least a 60, 70 or 80 degree angle respective to the planar substrate.

In a specific embodiment, the transitioning step involves aligning an array of transition-effecting structures with the planar substrate such that individual transition-effecting structures are oriented with the plurality of cut-outs; and inserting the array of transition-effecting structures through the planar substrate to transition material at the cut-outs to be out of plane with the planar substrate. The transition-effecting structures typically comprise elongated bodies such as hypodermic needles or dispensing needles. Another embodiment comprises a substrate comprising a plurality of microneedles produced by the methods described herein.

According to another embodiment, disclosed is a hollow needle array that includes a base; and a plurality of hollow needles secured to the base and extending orthogonally from the base.

In a further embodiment, disclosed is a system that includes the hollow needle array described above, wherein the base comprises one or more apertures; and a 3D printed release press comprising one or more elongated bodies configured for insertion into the one or more apertures, wherein insertion of the one or more elongated bodies assists with release of hollow needle array from a microneedle structure.

In yet another embodiment, provided is a 3D MEA platform that includes a 3D printed substrate; one or more conductive traces deposited on the 3D printed substrate; one or more microneedles disposed suprajacent to the one or more traces; an insulation layer disposed on to the microneedles; and a culture well disposed suprajacent to the insulation layer, wherein the microneedles protrude through the insulation layer into the culture well. In a specific example, the substrate is comprised of a resin such as, but limited to, 3DP. In a more specific embodiment, the one or more microneedles are aligned on top of the one or more traces. The microneedles are typically comprised of metal such as stainless steel. In another more specific example, the substrate layer of the 3D MEA platform comprises one or more recesses into which traces of the trace layer are deposited. In a specific example, the microneedles are produced by providing cut-outs in a planar sheet and transitioning material at the cut-outs such that the material extends orthogonal to the planar sheet.

In another embodiment, provided is a 3D MEA platform that includes a first plurality of conductive traces; a 3D printed substrate disposed suprajacent to the first plurality of traces; a second plurality of conductive traces deposited on the 3D printed substrate, a plurality of conductive connectors connecting the first plurality of traces to the second plurality of traces through the 3D printed substrate; a plurality of microneedles disposed suprajacent to the second plurality of traces; an insulation layer disposed on to the microneedles; and a culture well disposed suprajacent to the insulation layer, wherein the microneedles protrude through the insulation layer into the culture well. The substrate may be comprised of a material that can be cured such as a resin. The substrate layer may include one or more recesses into which the conductive traces of the second plurality of conductive traces are deposited. The microneedles may be produced by providing cut-outs in a planar sheet and transitioning material at the cut-outs such that the material extends orthogonal to the planar sheet. The connectors may be produced by forming a plurality of vias in the 3D printed substrate and filling the vias with a conductive material. One non-limiting example of a conductive material includes silver.

According to other embodiments, a modular MEA system is provided. The modular system comprises a first base including an array of micro-pillars having a conductive material associated therewith; a second base defining a culture well and comprising a plurality of apertures within the well for receiving the array of micro-pillars; and a plurality of microneedles aligned with the plurality of apertures; wherein as the first base and second base are brought together, the plurality of microneedles and micro-pillars extend through the plurality of apertures. In a specific example, the micro-pillars comprise a via with an opening at a bottom end of the micro-pillars and an opening at a side wall of the micro-pillars and a conductive material disposed within the via. The plurality of microneedles may be arranged such that they conductively interact with the conductive material at the opening in the side wall. The first base may define a recess into which the second base sits. The modular system may further comprising a third base positioned between the first base and second base, wherein the third base comprises a window through which the micro-pillars extend and one or more attachment components for attaching to the first base and second base or both.

The present disclosure is also related to U.S. patent application Ser. No. 16/104,752 (App No. '752, published as U.S. Pat Pub. US20190082615), which is incorporated herein. Those skilled in the art will appreciate that the micromilled microneedles and arrays disclosed herein can be substituted for the those disclosed in App No. '752.

The present disclosure is also related to U.S. patent application Ser. No. 15/887,556 (App No. '556) which is incorporated herein. Those skilled in the art will appreciate that the MEA and MNN described herein could be substituted for the MEA and MNN described in App No. '556.

EXAMPLES

Example 1: SLA 3D Printed, CNC Micromilled MEA

Substrate, Design, Fabrication, and Preparation

Iteration 1 10 of the in vitro culturing 3D MEA platform was designed to be a highly simplistic, and effective assembly technique (FIG. 1). The SLA 3D printed base 12 was designed to house an attachable culture well 14 which could be attached with a biocompatible, and adhesive elastomer such as Polydimethylsiloxane (PDMS). The stainless-steel electrodes 11 were fabricated through CNC micromilling, which typically is used for the bulk material definition, but for this purpose was able to precisely mill 2D electrodes that were then transitioned manually to 3D. The schematics in FIG. 1 (*a-d*), demonstrate the proposed design and assembly for this iteration 1. Positioned between the base 12 and the electrodes (microneedles) 11 is layer 13 with conductive traces 16 disposed thereon. The microneedles 11 and the traces 16 conductively connect upon assembly of the platform 10. FIG. 1B shows a close up of one of the microneedles 11 extending through the insulation layer 17 and into the well 14.

A 3D printed packaging substrate was designed on Solidworks 3D CAD software (Dassault Systems, 2016) and 3D printed (substrate dimensions: 20 mm width; 20 mm length; 1 mm thick) using commercially available clear (FLGPCL04) resin on the Formlabs Form 2 Micro-stereolithography (µSLA) 3D printer (Formlabs, USA), with a laser wavelength of 405 nm (FIG. 2*a*). A 3×3 matrix of attachment wells, 3 mm wide, 3 mm long, and 500 µm deep, with a 2 mm pitch were designed into the base of the substrate for placement of the microelectrodes. The substrate was subsequently rinsed twice with isopropyl alcohol (IPA) (SigmaAldrich, USA) for 10 minutes each and air dried.

Figure 2:
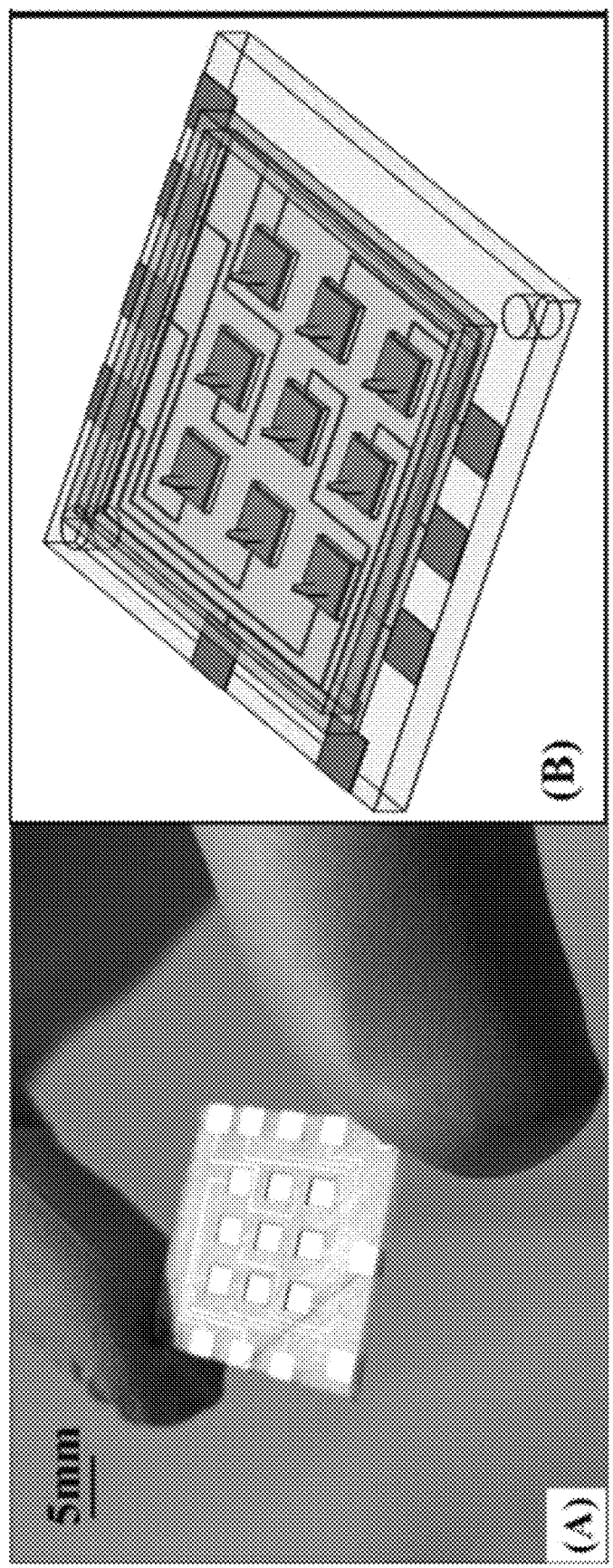
FIG. 2: (A) Optical image of the 3D printed substrate with deposited traces. (B) Additional overview of the schematic, highlighting the individual components in the completed assembly.

Included in this design was a custom attachable culture well ring 15 (15 mm×15 mm×500 µm) which was also printed and washed along with the base substrate (FIG. 2b). A deposition stencil mask was micromilled from 50 µm thick 316L stainless steel (Trinity Brand Industries, USA), using the T Tech Quick Circuit Prototyping System J5 (T Tech, USA). A metallization layer consisting of 20 nm Gold/Palladium (Au/Pd) was deposited through a trace pattern in the stencil mask on to the top side of the substrate using the Quorum Q150T Plus sputter coater (Quorum Technologies LTD., UK), at 20 mV with a 12 nm/min deposition rate (FIG. 2). The purpose of the layer was to route conductive tracings from the microneedle electrodes themselves, to outside the culturing area for measurement contacts.

Metal Micro Fabrication and Insulation

Figure 3:
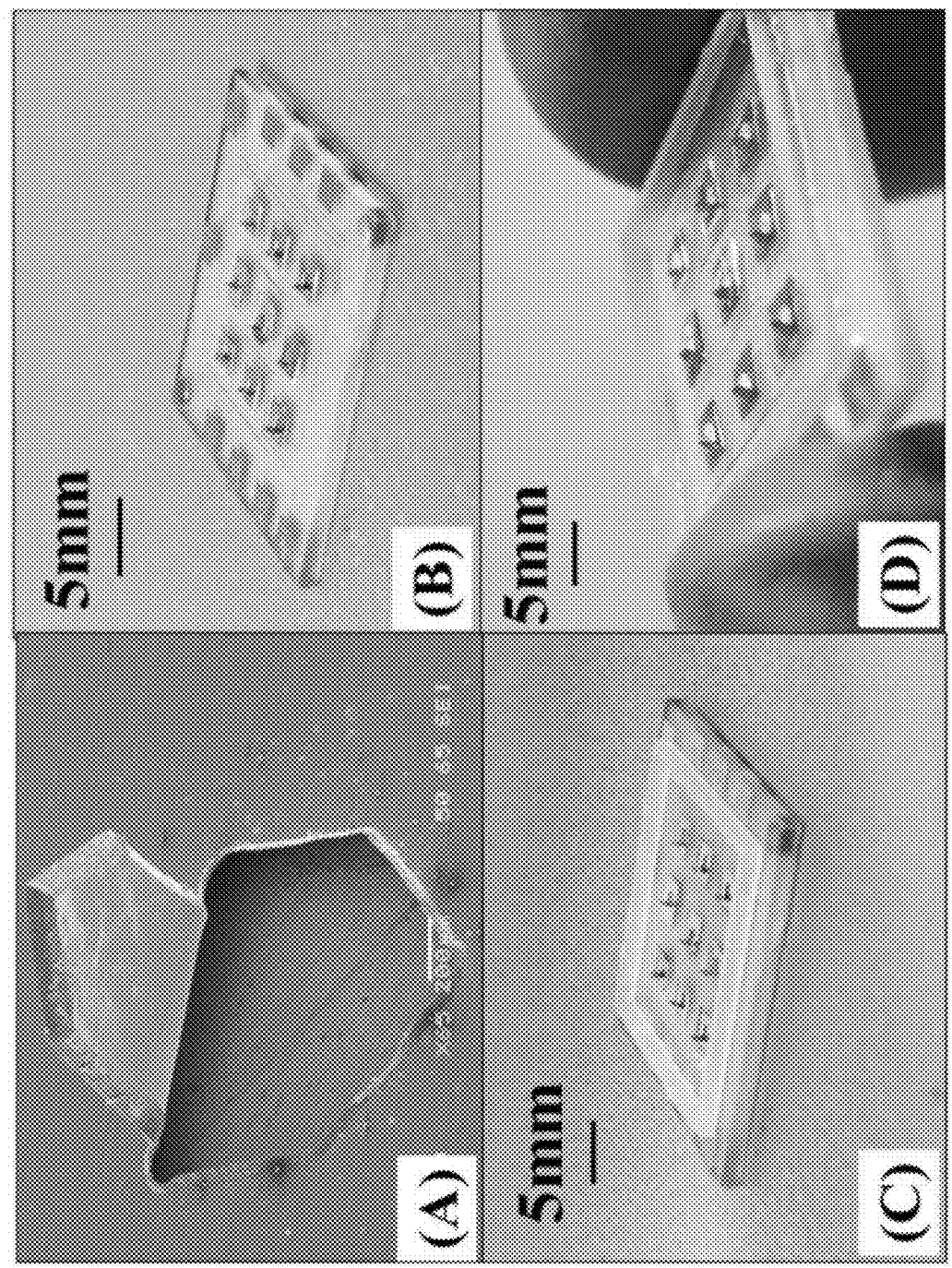
FIG. 3: (A) SEM image of the micromilled electrodes before insulation. (B) Optical image of the electrodes placed in their respective wells on the deposited traces. (C) Optical image of the assembled device before insulation with the culture well. (D) Completed device assembly, after PDMS insulation.

A 316L stainless steel sheet 50 µm thick (Trinity Brand Industries, USA), was micromilled using the T Tech Quick Circuit Prototyping System J5 (T Tech, USA) into individual 2D microneedle electrodes (FIG. 3a). Each microneedle electrode was milled from a demarcated 2.8 mm by 2.8 mm section of the steel sheet. The individual microelectrode needles are transitioned manually to 3D, resulting in a height of 500 µm and a width of 500 µm. The overall base from which each microneedle electrode is transitioned measured approximately 2.5 mm by 2.5 mm. The base structures along with its respective needles were placed in to the 3 mm by 3 mm cut outs in the 3D printed base substrate, on top of the Au/Pd deposited packaging traces (FIG. 3b). PDMS was mixed in the standard 10:1 ratio [162] (PDMS polymer: thermal cross-linker) and was cast over the substrate to an approximate thickness of 300 µm to act as the insulation layer for the device. The culture well was attached in a similar manner, and the assembly was placed into an oven to cure for 24 hours at 45° C. (FIG. 3 (c & d)).

Characterization

Figure 4:
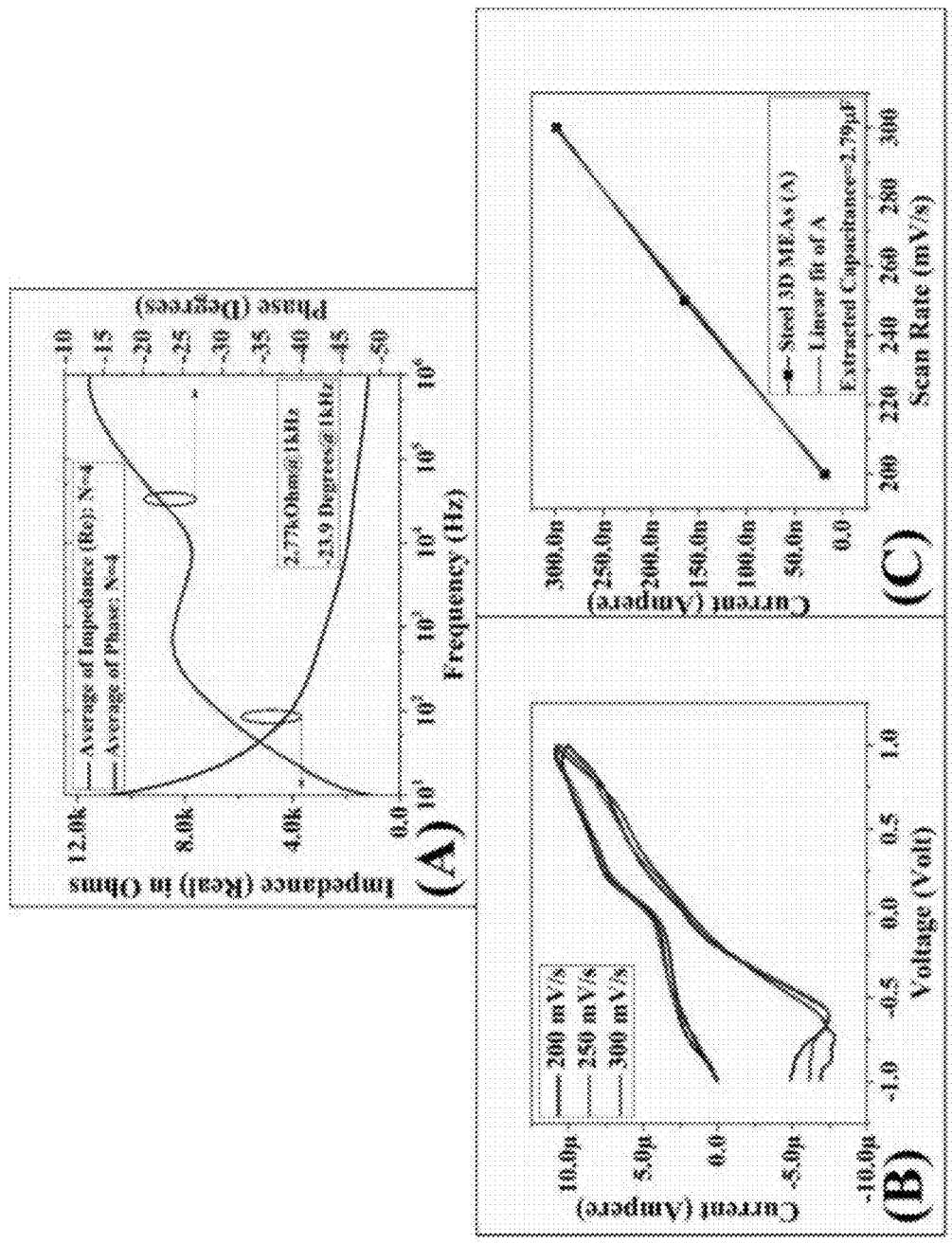
FIG. 4: (A) Full spectrum impedance and phase of the MEA, demonstrating 2.77 kΩ and 23.9° at 1 kHz respectively. (B) Cyclic Voltammogram of the MEA device at 200, 250 and 300 mV/s. (D) Graph of extracted capacitance from (C), showing a 2.79 μF value.

The iteration 1 device demonstrated an impedance and phase signature consistent with microelectrodes of similar sizes [68]. The average impedance was measured to be 2.77 kΩ at 1 kHz (FIG. 4a). SEM imaging of the MEA recording tips, was able to corroborate this observation, by demonstrating an electrode size of approximately 200 µm. The phase of the electrode at 1 kHz was measured to be −23.9°. Cyclic Voltammetry scans were performed at 200 mV, 250 mV, and 300 mV from which the capacitance value of the MEA was extracted. A higher value of capacitance was extracted and calculated to be 2.79 µF, indicating this device is suitable for electrophysiological measurements [143] (FIG. 4 (b & c)).

Example 2: SLA 3D Printed, CNC Micromilled MEA

Substrate, Design, Fabrication, and Preparation

Figure 5:
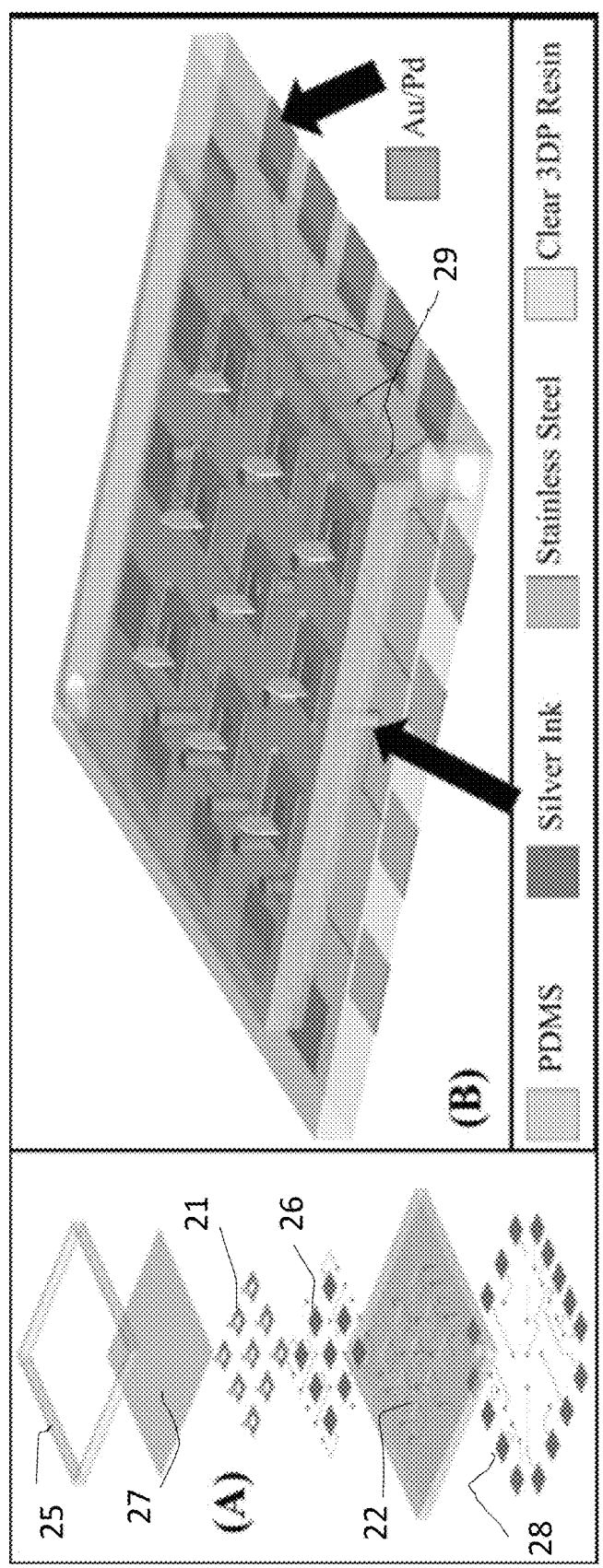
FIG. 5: Process flow for the development, assembly and characterization of the iteration 2 in vitro MEA platform. (A) Exploded schematic of the device, showing the 3D printed substrate, traces, electrode needles, insulation and culture well. (B) Overview of the assembled schematic, highlighting the two sets of Au/Pd traces.

The schematics in FIG. 5 (a & b) depict the second iteration 20 of an MEA platform. Iteration 20 includes a substrate base 22, traces 26, microneedles 21, an insulation layer 27 and well ring 25. Also included are a bottom array of conductive traces 28 under the base 22. Vias 29 are provided in the base 22 which are able to transition the top traces 26 to the bottomside traces 28 of the substrate 22. Vias transitioning the 3D microelectrodes to the bottomside of substrate base, which are necessary for several electronics amplifiers that the devices interface with which transmit signals from the cells through the microelectrode to the electronics system. The 3D MEA structure was fabricated using a similar method to the one described in Example 1. Silver-ink (Epo-Tech, USA) was used to fill the vias, and secure the MEA needles in place, and a similar PDMS-based attachment and insulation were used to isolate the individual electrodes and secure the culture well. Pulsed nanomaterial electrodeposition (detailed below) was introduced for this design as well, to better functionalize the electrodes by increasing the functional surface area of a micro-scale electrode recording site.

Figure 6:
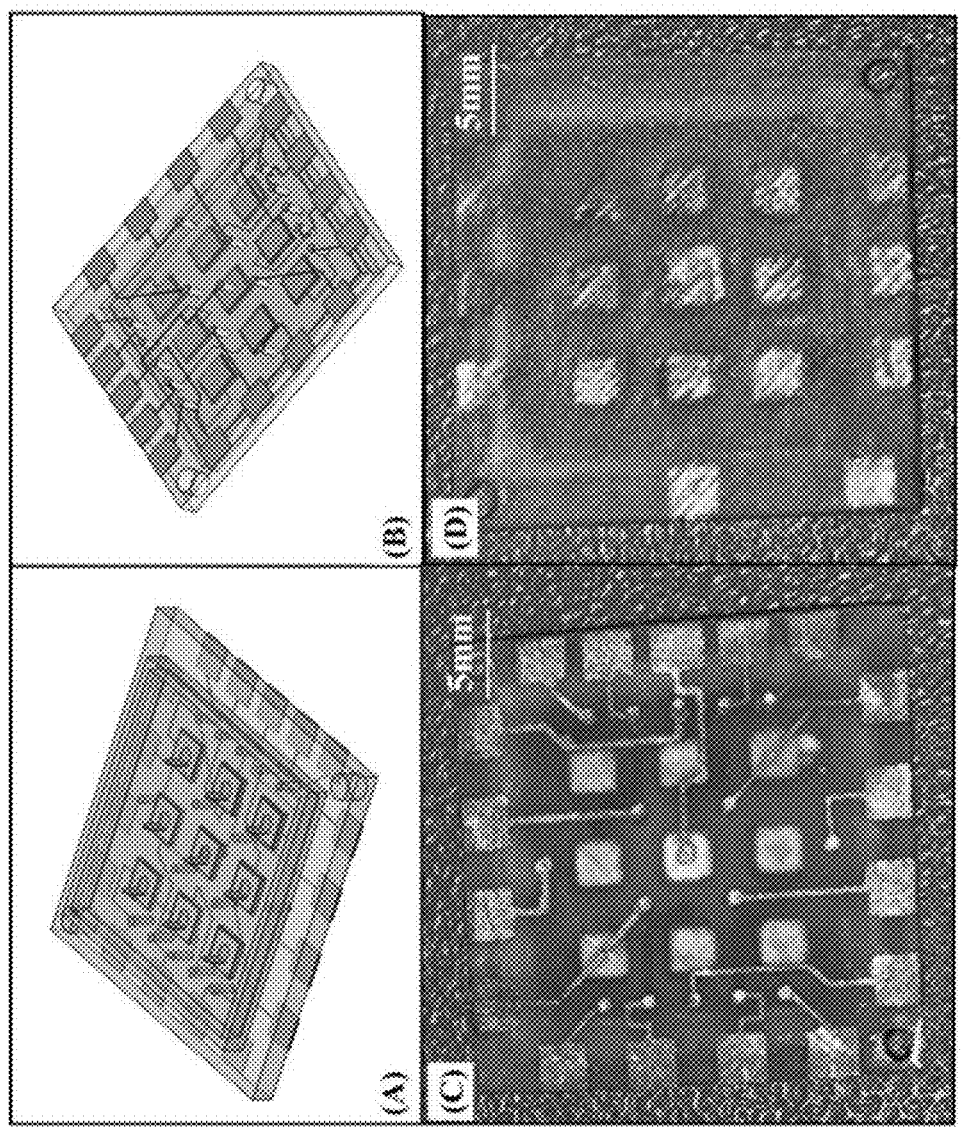
FIG. 6: (A) Schematic of the assembled device, highlighting the individual components, including the transition to back-side traces with vias. (B) Similar schematic to (A), showing the device from the back to highlight the new design with deposited traces on the back for connection. (C) Optical image of the iteration 2 device, to highlight the via transitions. (D) Optical image of the iteration 1 device to demonstrate the fabrication differences in trace design from the iteration 2 trace pattern from (C).

A 3D printed packaging substrate was designed on Solidworks 3D CAD software (Dassault Systems, 2016) and 3D printed (substrate dimensions: 20 mm width; 20 mm length; 1 mm thick) using commercially available clear (FLGPCL04) resin on the Formlabs Form 2 Micro-stereolithography (µSLA) 3D printer (Formlabs, USA), with a laser wavelength of 405 nm (FIG. 6 (a & b)). 3 mm wide, 3 m long, and 500 µm deep, and 2 mm pitch wells were designed into the base in a 3×3 matrix for attachment of the microelectrode needles. The substrate was subsequently rinsed twice with isopropyl alcohol (IPA) (Sigma-Aldrich, USA) for 10 minutes each and air dried. Iteration 2 also included a custom attachable culture well ring (15 mm×15 mm) which was also printed and washed.

Vias of dimension 400 µm diameter vias to transition routing traces to the bottom of the chip, were integrated in this iteration (FIG. 6c). The vias were defined by casting Epo-tek® EJ2189 silver-ink (Epo-Tech, USA), into the cutouts and the ink was allowed to cure for 36 hours at 45° C., to minimize warpage of the resin. After curing, the excess ink was removed using isopropyl alcohol, leaving behind only the ink in the vias. A deposition stencil mask for both the top and bottom of the device was micromilled from 50 µm thick 316L stainless steel (Trinity Brand Industries, USA), using the T Tech Quick Circuit Prototyping System J5 (T Tech, USA). A metallization layer consisting of 20 nm Gold/Palladium (Au/Pd) was deposited through a trace pattern in the stencil mask on to the top side of the substrate using the Quorum Q150T Plus sputter coater (Quorum Technologies LTD., UK), at 20 mV with a 12 nm/min deposition rate (FIG. 6c). The purpose of the layer was to route conductive tracings from the microneedle electrodes themselves, to the via connects, which would then transition the packaging traces to the bottom of the chip for measurement contacts. A comparison of this approach including the vias, with the iteration 1 top-side approach can be seen in FIG. 6(c & d).

Metal Micro Fabrication and Insulation

Figure 7:
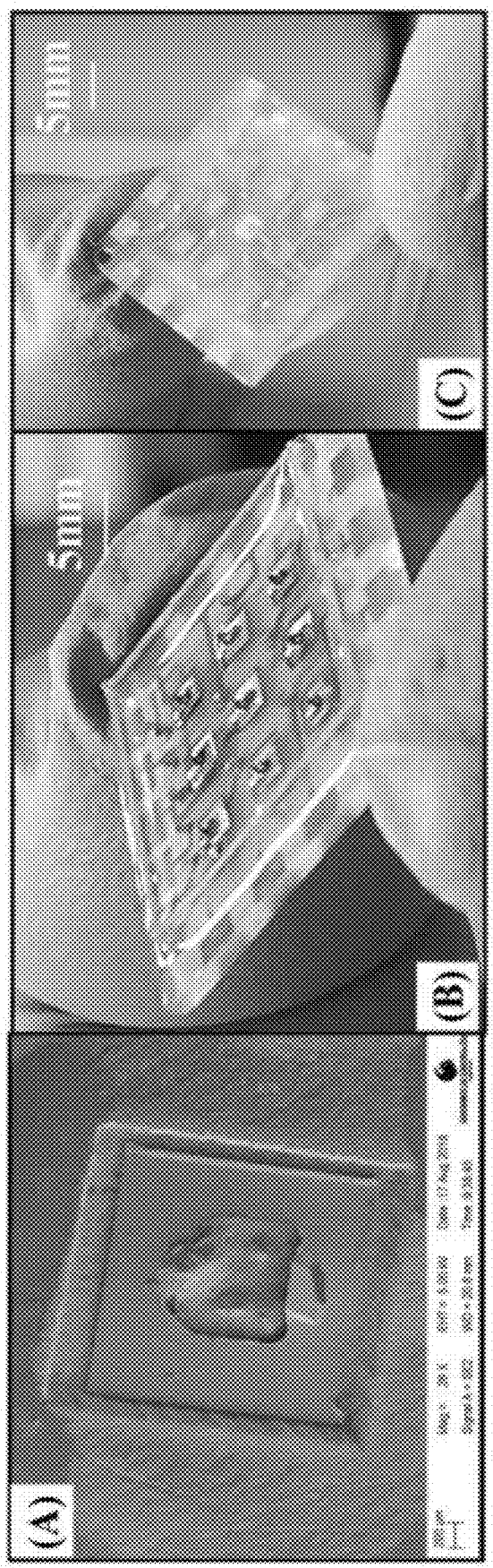
FIG. 7: (A) Optical image of the completed iteration 2 device after PDMS insulation. (B) Optical image of the device from the back to show the new trace deposition. (C) SEM image of the bulk electrode needle assembled on the 3D printed resin atop silver in-cast attachment sites, before PDMS insulation.

A 316L stainless steel sheet 50 µm thick (Trinity Brand Industries, USA), was micromilled using the T Tech Quick Circuit Prototyping System J5 (T Tech, USA) into individual 2D microneedle electrodes. Each microneedle electrode was milled from a demarcated 2.8 mm by 2.8 mm section of the steel sheet. The individual microelectrode needles are transitioned manually to 3D, resulting in a height of 500 µm and a width of 500 µm. The overall base from which each microneedle electrode is transitioned measured approximately 2.5 mm by 2.5 mm. The base structures along with its respective needles were placed in to the 3 mm by 3 mm cut outs in the 3D printed base substrate, on top of the Au/Pd deposited packaging traces (FIG. 7a). PDMS was mixed in the standard 10:1 ratio (PDMS polymer: thermal cross-linker) and was cast over the substrate to an approximate thickness of 300 µm to act as the insulation layer for the device. The culture well was attached in a similar manner, and the assembly was placed into an oven to cure for 24 hours at 45° C. (FIG. 7 (*b* & *c*)).

Pulsed electroplating was performed. An electroplating solution for the deposition of nano-porous platinum (N-P Pt) (plating solution: 3.75 mL ~8% chloroplatinic acid, 0.2 mL of 0.005 wt % lead acetate, 4.065 mL of 1.23M HCl (all from Sigma-Aldrich) and 2.085 mL of DI water) [34] was added into the culture well and a platinum wire, used as the counter electrode, was inserted into the solution. The platinum electroplating solution was pre-heated to 80° C. in a glass beaker prior to being transferred to the culture well. The current and voltage control that is required to perform electroplating was implemented using a programmable Keithley 2400 Source Meter (Keithley Instruments, USA) with two probes. One of the probes is connected to the cathode which is attached to a piece of copper tape (Tapes Master, USA) shorting all of the contact pads of the device together and the other probe is connected to the anode to complete the circuit. This process involved using an instrument driver and programming an example interface that can serve to input the electroplating parameters. An executable LabVIEW program (LabVIEW NXG 2.1; National Instruments, USA), was used for adjustment of process parameters such as duty cycle, source amplitude, pulse time, number of pulses, compliance amplitude, and waveform type (pulsed or constant) [143]. A square wave pulse having a duty cycle of 50% was used with a current density of 1 A/cm2. The current was set to 10 mA per electrode, for 20/40 sec (single/double plating). The voltage compliance amplitude was set at 10 V and the electroplating was performed for 60 seconds. After the desired electroplating time, the plating solution was removed, and the culture well was rinsed with DI water and IPA. In an attempt to ascertain the best plating procedures for the N-P Pt, optimization conditions were tested. Through experimentation, it was found that by either electroplating before, or after PDMS insulation, varying levels of success in control of the plating procedure could be achieved. Ultimately it was ascertained that the "optimized" plating conditions were found when electroplating before insulation, and these optimizations were further explored by single and double coatings, and their differences were recorded as well.

Characterization

Figure 8:
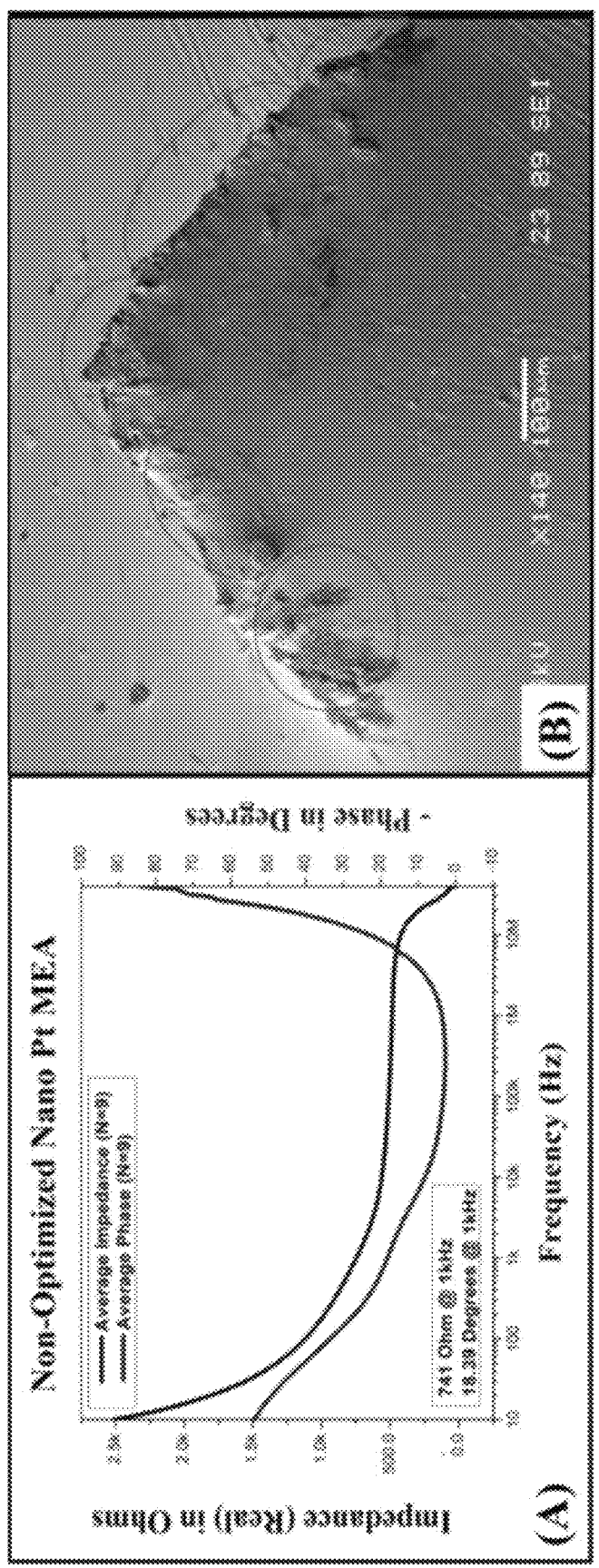
FIG. 8: (A) Full spectrum impedance and phase of the non-optimized platinum from after insulation, demonstrating 741 Ωs and −18.39° at 1 kHz, signifying a much larger electrode surface area than desired. (B) SEM image of the non-optimized platinum, where the outcroppings are denoted in the red circles.

Non-optimized N-P Pt electroplating resulted in very large irregular coatings (FIG. 8). As the PDMS was cast, it left additional outcroppings of N-P Pt exposed outside of the electrode recording site. Full spectrum impedance and phase measurements were taken for the non-optimized plating. The impedance at 1 kHz was found to be 741 Ω (N=9), which as previously mentioned, indicated a very large electrode surface area (FIG. 8*a*). This is supported by the SEM images, showing the large effective surface area of the N-P Pt electrode (FIG. 8*b*). The phase values obtained from the full spectrum frequency sweep, also support this assertion with a value of −18.39° at 1 kHz. The optimization of the electroplating was obtained by through reversing the order of insulation and electroplating steps.

Figure 9:
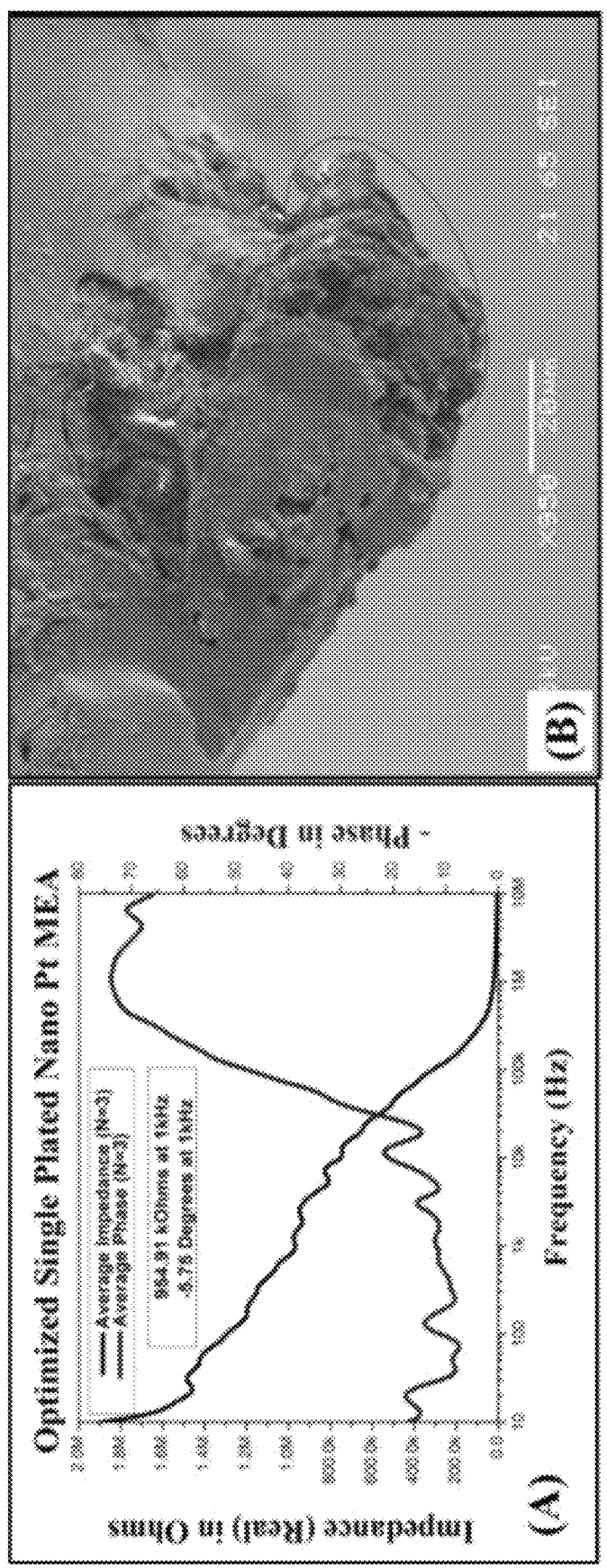
FIG. 9: (A) Full spectrum impedance and phase of the MEA with a more optimized, before insulation platinum electroplating, demonstrating 954.91 kΩ and −5.75° at 1 kHz. (B) SEM image of the single plating of optimized platinum, with the exposed outcroppings, highlighted in the red circles.
Figure 10:
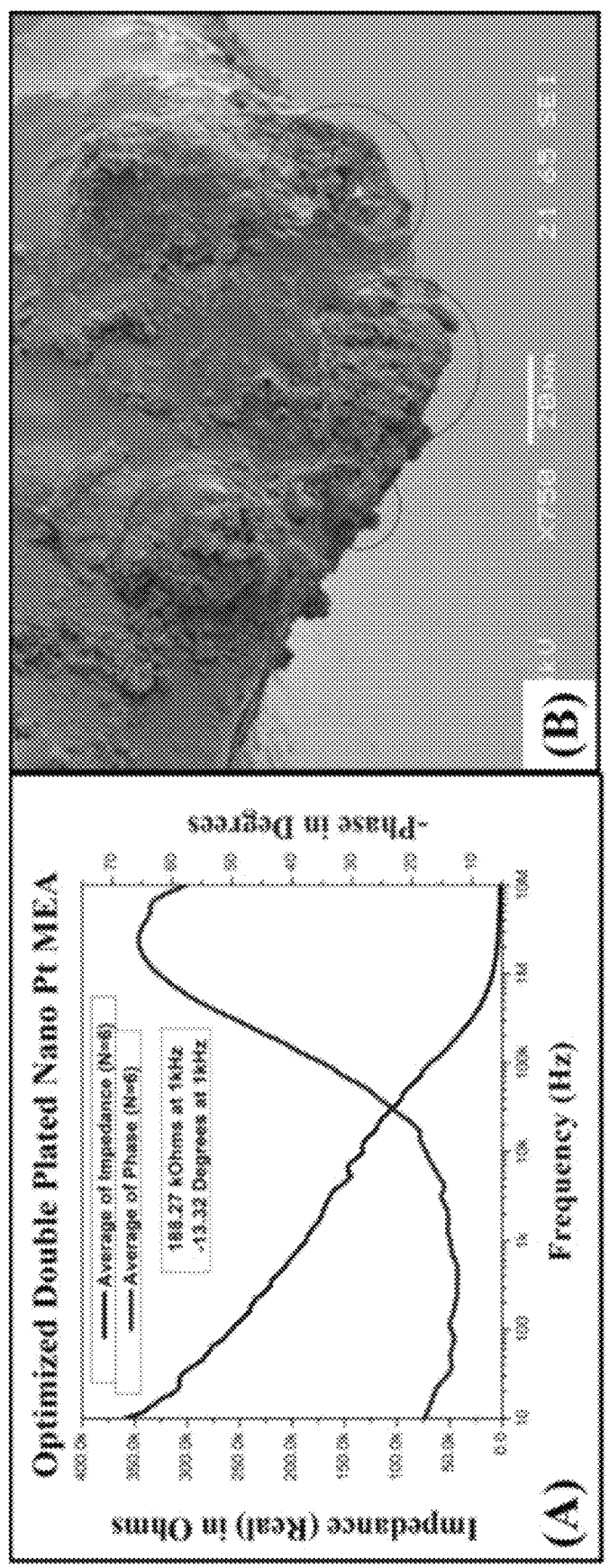
FIG. 10: (A) Full spectrum impedance an phase of the double coated, more optimized platinum MEA, demonstrating 188.27 kΩ and −13.32° at 1 kHz respectively. (B) SEM of the optimized double coated platinum electroplated electrode, with the red circles highlighting the nanomaterial recording site.

The single plated optimized electrodes provided much more reasonable microelectrode performance; converting the bulk mesoscale steel electrode (~700 μm diameter), into the optimized, single plated electrode (after electroplating and then insulation) with an impedance of 954.91 kΩ (N=9) at 1 kHz, with an approximate defined recording site radius of ~30 μm (FIG. 9 (*a* & *b*)). The phase of this electrode was found to be −5.75° at 1 kHz. A double electroplating protocol was then attempted (same protocol as above; 40 s total plating time), since the measured impedance was observed to be larger than usually reported values for N-P Pt [165]. The more optimized, double plated, microelectrode, was similarly defined from the bulk mesoscale stainless steel microneedle electrode material, and then electroplated twice with the parameters described in Section 4.3.2. The values measured for such a process were 188.27 kΩ (N=9) at 1 kHz, and the phase was measured at and −13.32° at 1 kHz (FIG. 10*a*). This impedance value is in the desired range for electrophysiological measurements, as it not only provides sufficient surface adhesion sites for cellular growth, but the 1 kHz impedance value lends itself to electrodes with the ability to pick up small cellular signatures with excellent Signal to Noise Ratios (SNRs). After insulation definition, the radius of curvature of the recording sites was ~50 μm, which was expected, and a more intricately rough nature of the N-P Pt was seen (FIG. 10*b*).

Figure 11:
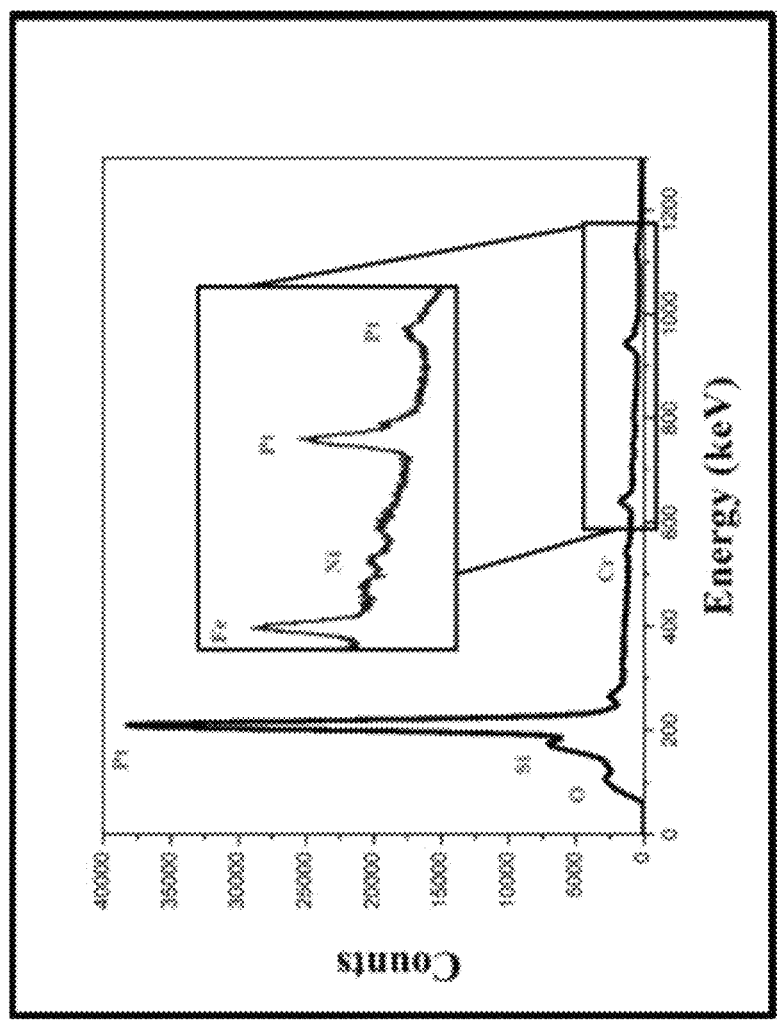
FIG. 11: EDS spectrum of the optimized double coated platinum nanomaterial, confirming the presence of near pure platinum at the recording site.

While the first step of nanomaterial electroplating increased the surface area of the tip, a double coating increased the surface area further. Energy Dispersive X-ray Spectroscopy (EDS) was performed to confirm the presence of the N-P Pt and ensure uniform coverage atop the stainless-steel microneedle structure (FIG. 11). The resulting data demonstrated a ~90% pure Pt composition on the electrodes, with only minor traces of silicon and oxygen (present potential from the PDMS insulation). This iteration demonstrates that pulsed electroplating is a reliable method for nanomaterial definition atop of micromilled stainless steel microelectrodes.

Example 3: SLA 3D Printed, Laser Micromachined MEA

Substrate, Design, Fabrication, and Preparation

Figure 12:
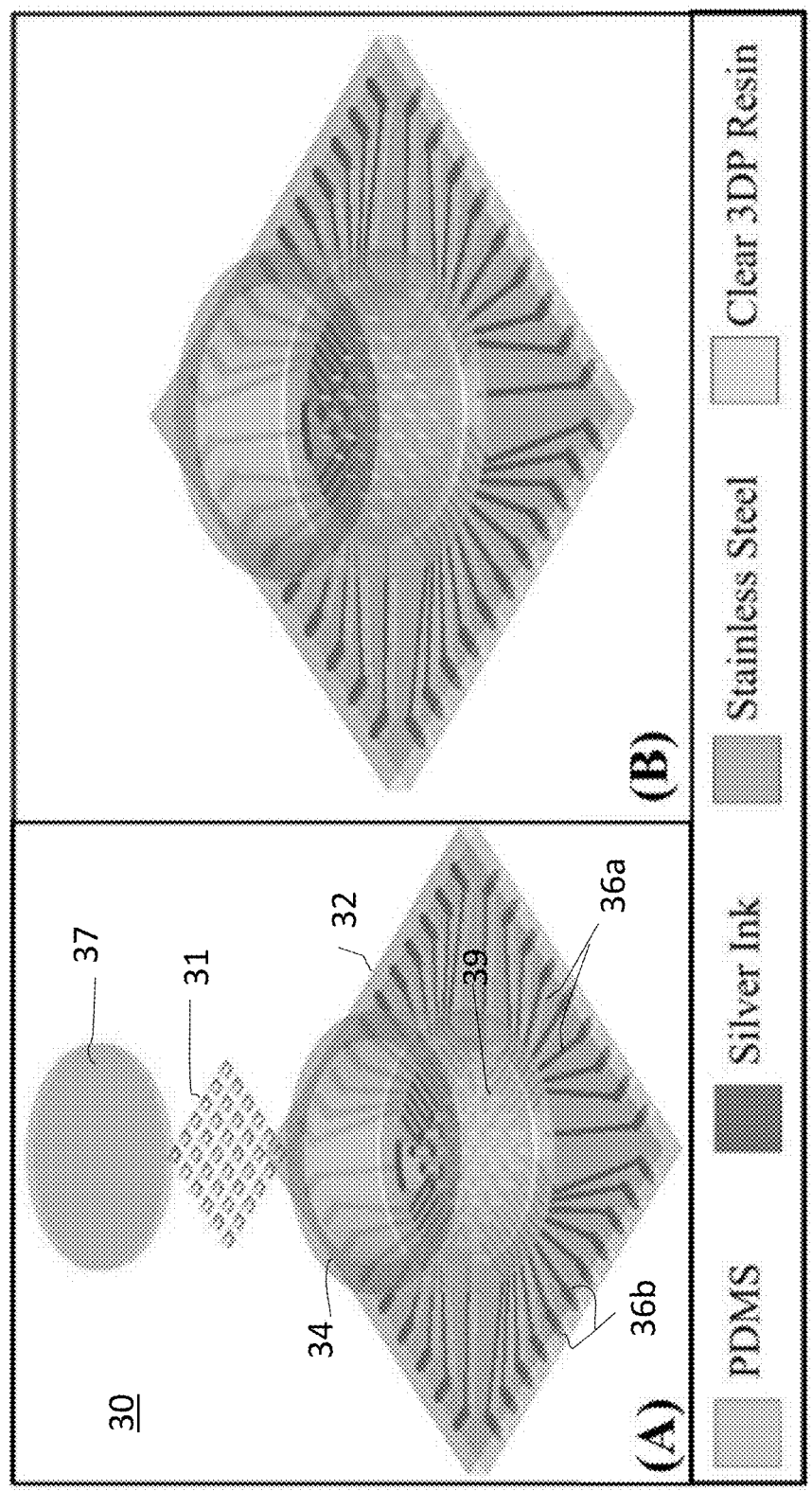
FIG. 12: Process flow for the design and fabrication of the iteration 3 in vitro MEA. (A) Exploded schematic of the device, showing the 3D printed substrate, silver-ink traces, electrode needles, insulation and culture well. (B) Overview of the assembled schematic, after the casting of the silver-ink into the traces.

The third iteration was the first major departure from the original design in order to integrate additional features and improvements. The SLA printed base was designed to have not only an integrated culture well, but also integrated vias and traces on the bottom of the chip. The integration of these structural features ensured a monolithic design concept for the 3D MEA. The micromachined electrode array, the silver ink used to define in the traces and the insulation layer were separately integrated. Array grid densities up to 8×8 and potentially even beyond are possible with this approach. Laser micromachining was introduced to both machine and isolate the individual electrodes. In lieu of pulsed nanomaterial electrodeposition step for this iteration, an acid pickling. protocol was implemented, which removed oxide impurities, and eliminated some of the surface roughness that are a result of the laser micromachining process. FIG. 12 illustrates this third iteration 30 and shows a base 32, a well 34, a plurality of microneedle electrodes 31 positioned within the well 34 and an insulation layer 37 in the well on top of the microneedle electrodes 31. The substrate 32 comprises a number of conductive connectors 36*a* and traces 36*b* that conductively interact with the electrodes 31. Vias 39 are defined in the substrate base 32 and include through conductive material that connect the microneedle electrodes 31 to the conductive connectors/traces 36*a,b*.

Figure 13:
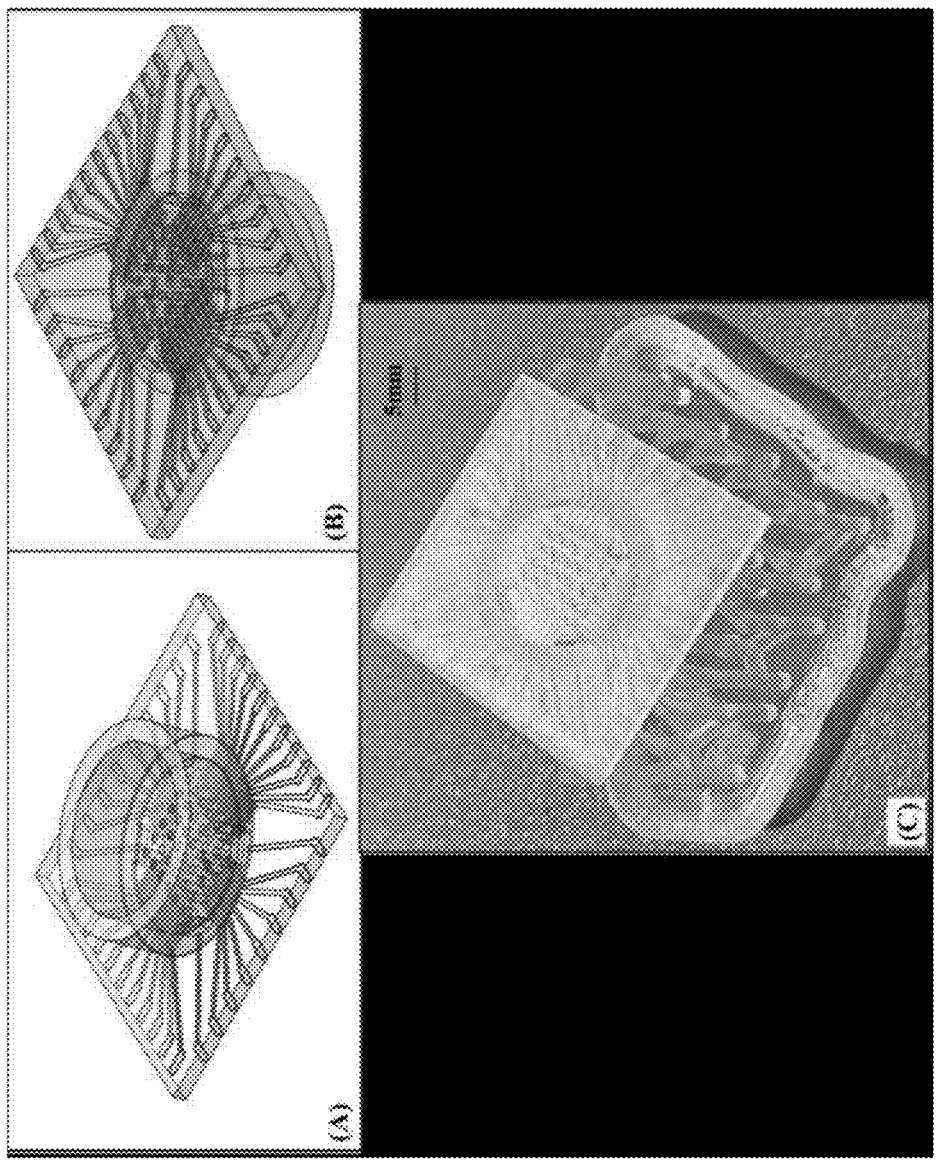
FIG. 13: Process flow for the design and fabrication of the iteration 3 in vitro MEA. (A) Schematic of the 3D printed base for this design, showing the monolithically integrated culture well on top. (B) Schematic of the same design from (A), showing the integrated ink-casting traces on the bottom-side. (C) Optical image of the 3D printed design from (A & B) still attached to its printing supports.
Figure 14:
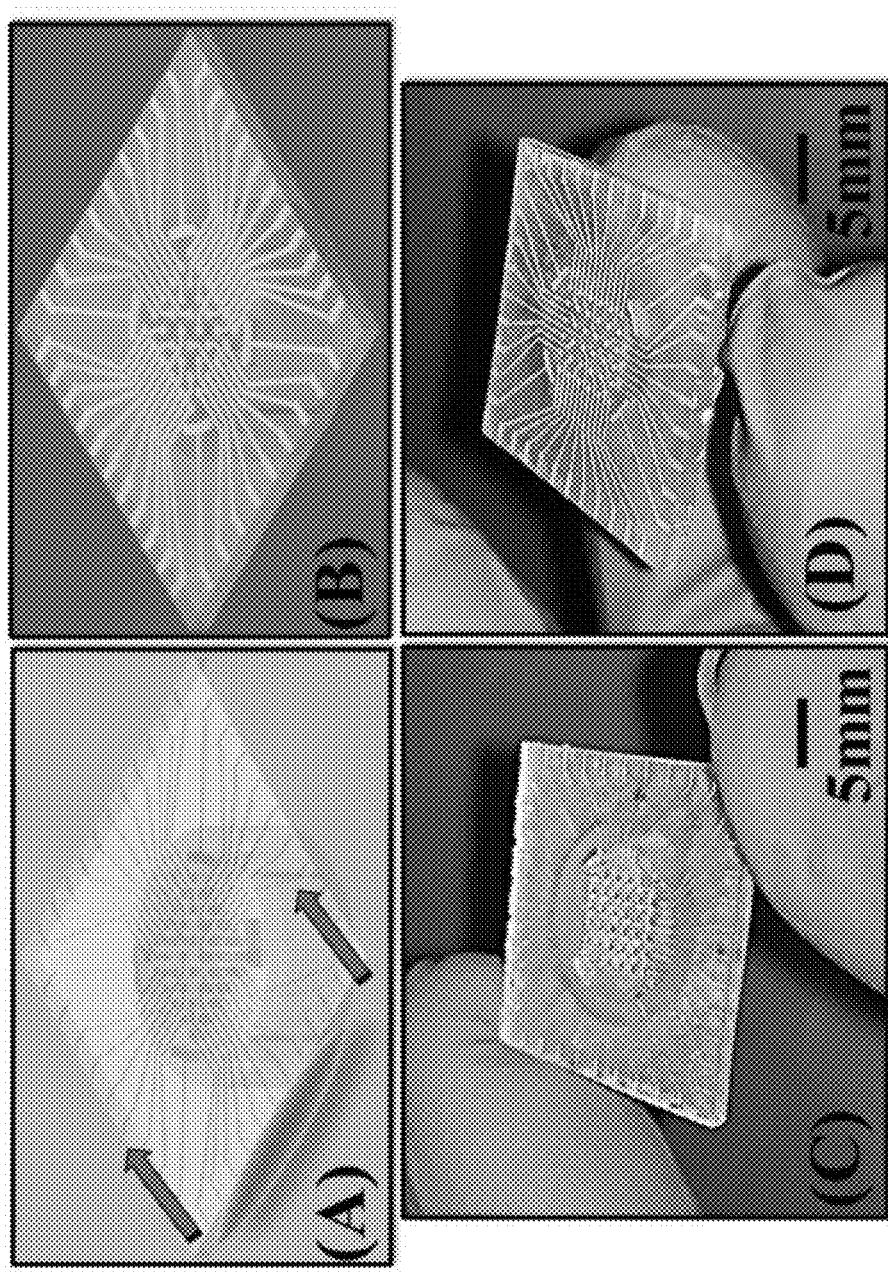
FIG. 14: (A) Schematic of the MEA design before ink-casting of the traces. (B) Schematic of the design after ink-casting and subsequent washing of the excess ink, revealing only the conductive traces. (C) Optical image of the device from (A) before ink-casting. (D) Optical image of the device from (B) after ink-casting and washing.

The 3D printed packaging substrate was designed on Solidworks 3D CAD software (Dassault Systems, 2016) and 3D printed (substrate dimensions: 20 mm width; 20 mm length; 1 mm thick) using commercially available clear (FLGPCL04) resin on the Formlabs Form 2 Micro-stereolithography (μSLA) 3D printer (Formlabs, USA), with a laser wavelength of 405 nm (FIG. 12 (*a* & *b*), and FIG. 13). The substrate was subsequently rinsed twice with isopropyl alcohol (IPA) (SigmaAldrich, USA) for 10 minutes each and air dried. Iteration 3 included 400 µm diameter vias to transition traces to the bottom of the chip as well as bottomside traces 150 µm wide, and a monolithically integrated culture well on the topside of the chip. The traces and vias were defined by casting Epo-tek® EJ2189 silver-ink (Epo-Tech, USA), into the trace and via cutouts in the printed structure and the ink was allowed to cure for 36 hours at 45° C., to minimize warpage of the resin [34] (FIG. 14).

After curing, the excess ink was removed by gently wiping with isopropyl alcohol, leaving behind only the ink in the traces (fully isolated), and vias.

Metal Micro Fabrication and Insulation

Figure 15:
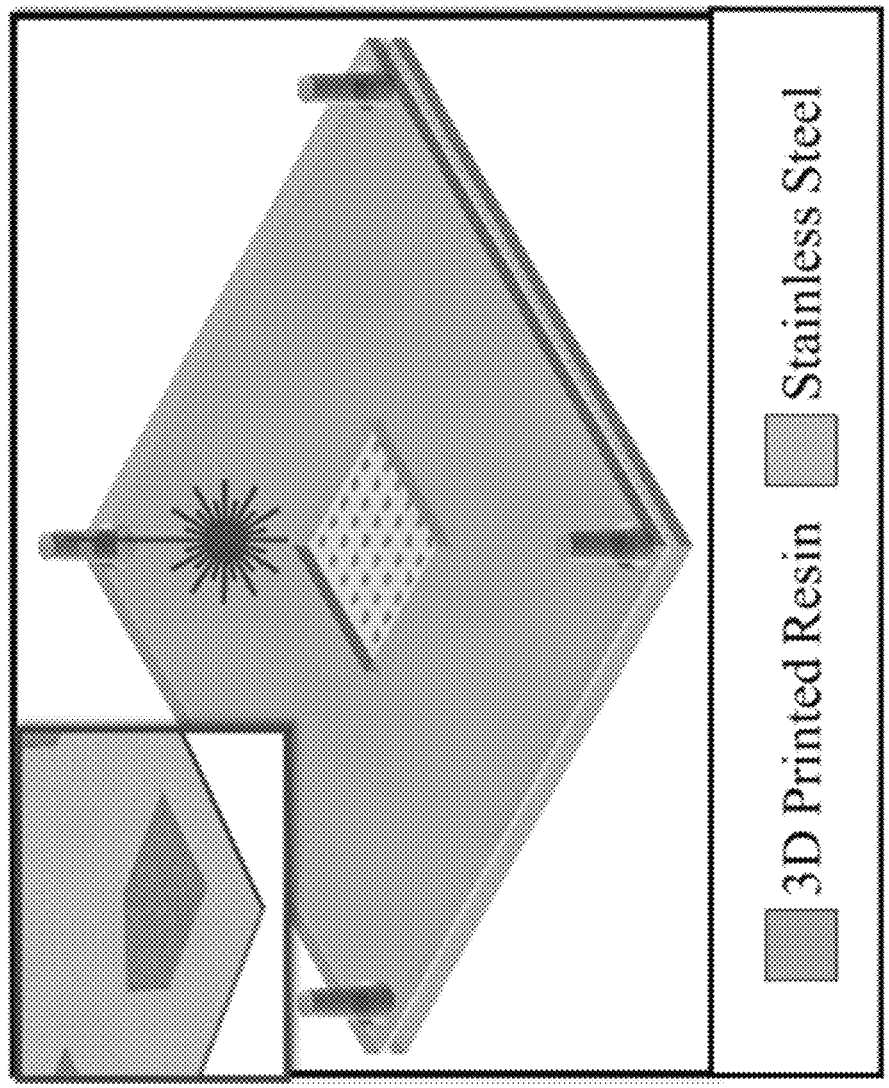
FIG. 15: Schematic of the first step in the Hypo-Rig assembly process, demonstrating the laser micromachining of the steel sheet into an array while pressed in the array holding assembly.
Figure 16:
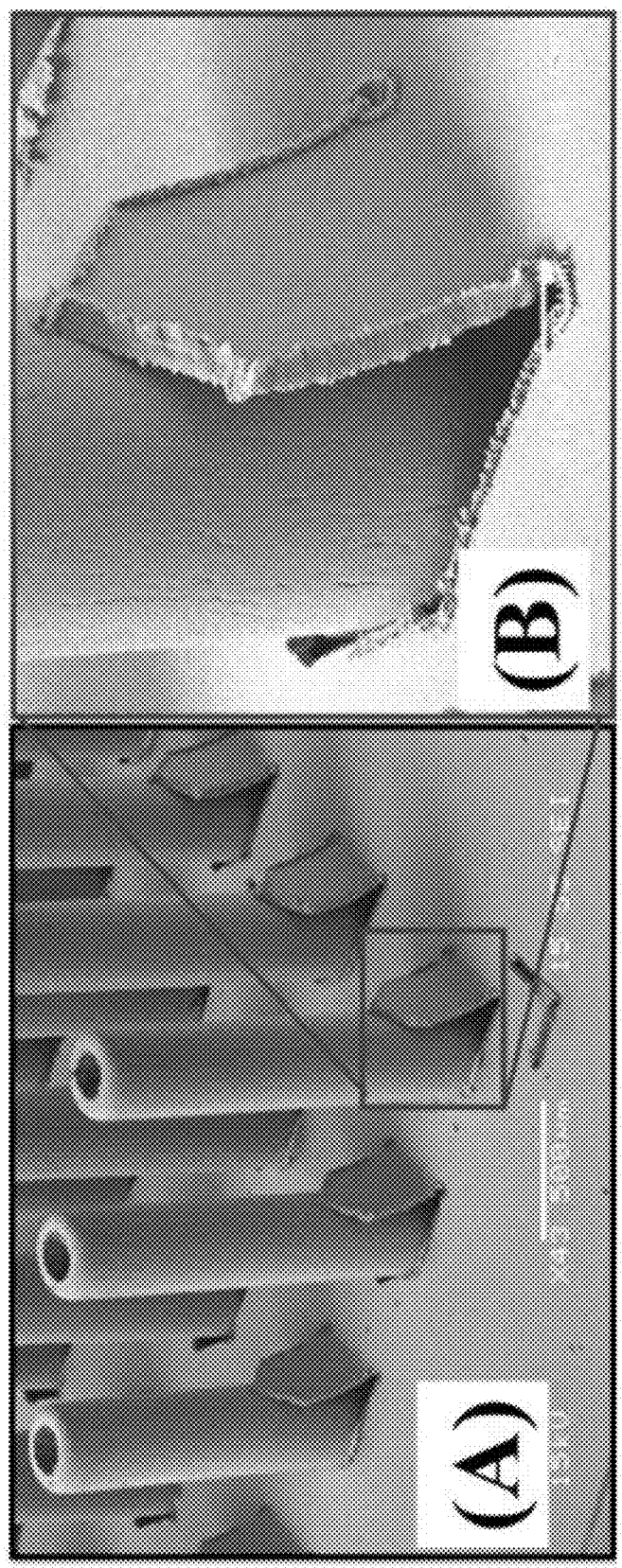
FIG. 16: (A) SEM image of the Hypo-Rig during the transition process, using dispensing needles. (B) Close up SEM of (A) showing the precision of the Rig in transitioning a bulk electrode.
Figure 17:
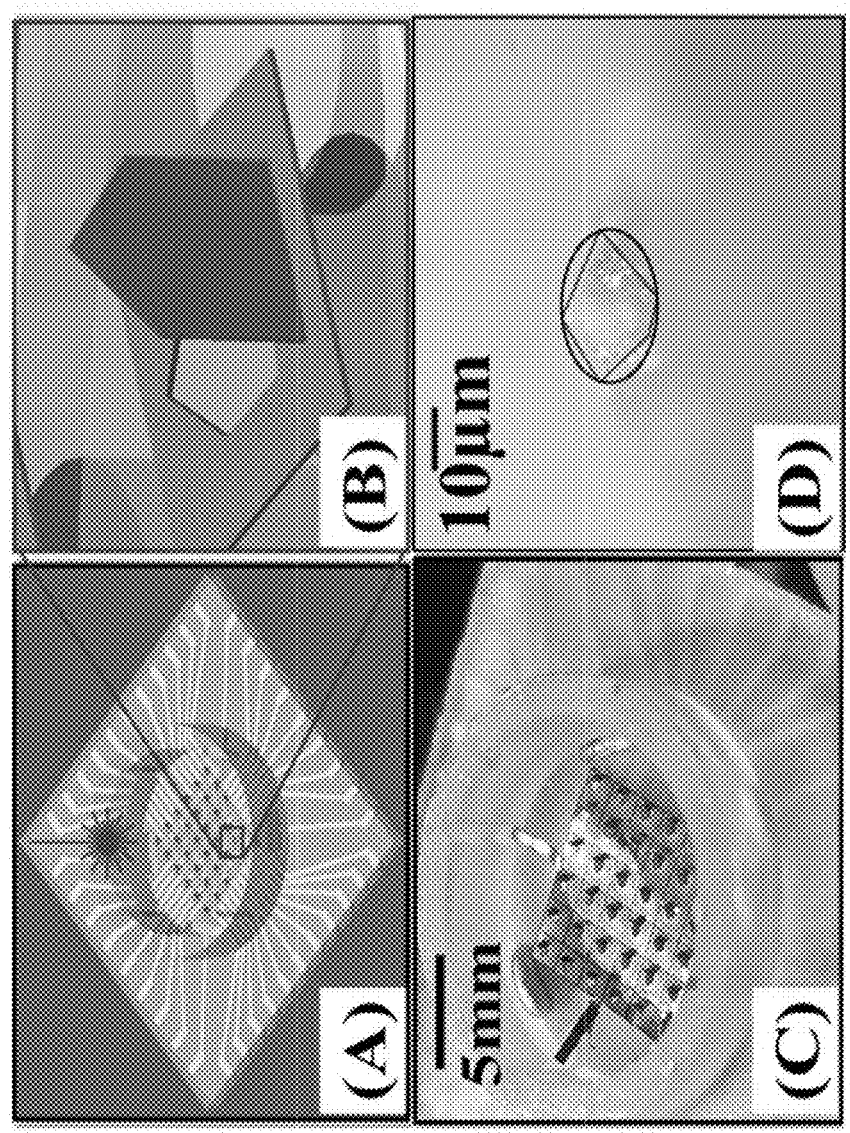
FIG. 17: (A) Schematic of the array being placed on the ink-cast device, and singulated into individual needles. (B) Schematic of an individual needle after Polystyrene insulation and subsequent laser micromachining to expose the recording site. (C) Optical image of the transitioned Steel array on the 3D printed, ink-cast substrate, after singulation and before insulation. (D) Optical image of the in-situ ablation of the steel electrode recording site.

The 3D metal microelectrodes were machined from 12.5 µm thick 316L stainless steel (Trinity Brand Industries, USA) using the QuikLaze 50 ST2 laser micromachining system (Eolite Lasers, USA) to define a 6×6 grid of planar (2D) microelectrodes (electrode dimensions: 300 µm width; 350 µm height; 1 mm pitch) with 1064 nm wavelength IR light (6 mJ power, and 50 Hz repetition rate) (FIG. 15). The planar electrodes were subsequently acid pickled in a solution of DI Water (80 wt %), 70% HNO3 (11 wt %), 49% HF (9 wt %) at 50° C. for 1.5 minutes with sonication, to remove oxide impurities, and to reduce the roughness of the electrode surface. The steel was then rinsed in DI water briefly. The electrodes were transitioned from 2D to 3D by using the custom fabricated Hypo-Rig, to ensure a precise and controlled angular spread across the array (details provided in Example 5 infra) (FIG. 16). The array was singulated into individual microelectrodes using the same laser micromachining parameters described above (FIG. 17 (a & c)).

A 4.5 µm thick, 10% polystyrene in Tetrahydrofuran (THF) (w/v) (Sigma Aldrich, USA) layer was spin-coated (5000 rpm for 30 seconds) over both designs to define a 3D insulation layer. The key to achieving conformal coatings on 3D structures having moderate to high aspect ratios is to engineer a balance between the viscosity of the solution and its evaporation rate. An optimum viscosity will allow for mobility to coat 3D geometries, whereas the optimum solvent evaporation rate would prevent any unwanted accumulation of the material being spin coated. Controlled burst ablation laser micromachining at an UV wavelength of 355 nm (0.4 mJ power, and 4 singular bursts per electrode), was used to selectively ablate the microelectrodes and define the 70 µm microelectrode recording sites (FIG. 17(b & d)).

Characterization

Figure 18:
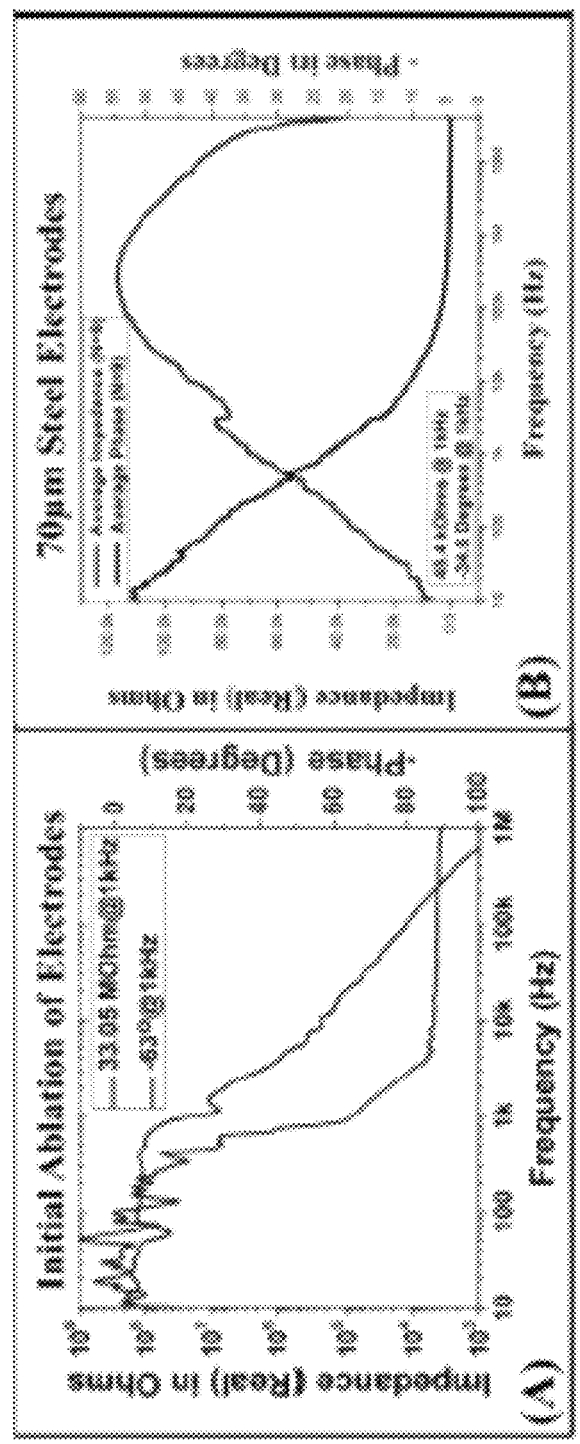
FIG. 18: (A) Full spectrum impedance and phase of the initial ablation of the MEA recording site, demonstrating 33.05 M$\Omega$ and $-63°$ phase at 1 kHz respectively. (B) Full spectrum impedance and phase of the MEA recording site after controlled burst ablation to a size of 70 μm, resulting in 45.4 k$\Omega$ and $-34.6°$ at 1 kHz respectively.

Full spectrum impedance and phase were measured using a BODE 100 Impedance Analyzer (Omicron Labs, Austria) with a Platinum (Pt) anode in Phosphate Buffer Solution (PBS), during the laser ablation process to define the microelectrodes (FIG. 18). The values measured clearly delineate between a fully insulated state (open), at the beginning of ablation (33.05 MΩ and −63° at 1 kHz), and the definition of 70 µm microelectrodes (N=9; 45.4 kΩ, and −34.6° at 1 kHz) (FIG. 18(a & b)). The 70 µm microelectrode was well characterized for residual oxide and impurity removal. The full spectrum impedance and phase data for the partially and fully ablated microelectrodes (highlighting 1 kHz values) are shown in FIG. 19. The fully insulated steel MEA provided data in high MΩ, demonstrating a conformal polystyrene insulation coating.

The beginning of ablation resulted in reduced impedance signatures and fully ablated microelectrodes demonstrated characteristics similar to literature reported values [166]. This impedance analysis technique during the microfabrication of iteration 3 represents pseudo-in situ laser characterization, demonstrating a powerful methodology for studying microfabrication processes.

Example 4: DLP 3D Printed, Laser Micromachined Modular MEA

Substrate, Design, Fabrication, and Preparation

Iteration 4 was the culmination of the collective iterative technique that was developed as part of the demonstrated work in the above Examples. Iteration 3 had challenges with respect to the adhesion of the steel to the 3D printed substrate, as stainless steel tends to bow in a convex manner (with respect to the steel-substrate interaction) post-laser micromachining. This goal of the fourth iteration of the 3D MEAs was a "Modular" design. It was comprised of a custom 3D printed series of interlocking parts which would help ensure maximum connectivity and stability by sandwiching the stainless steel between two structural features of 3D printed resin. FIGS. 20-27 illustrate the schematic design process flow for the three individual levels of the modular design, beginning with the "cross-connect vias", and ending with the two-part micro pillar connect, "Modular" design. The design and process development were performed on a 3×3 microneedle electrode array though the concepts demonstrated can scale from 1×1 to 8×8 and higher densities of 3D electrodes.

Figure 20:
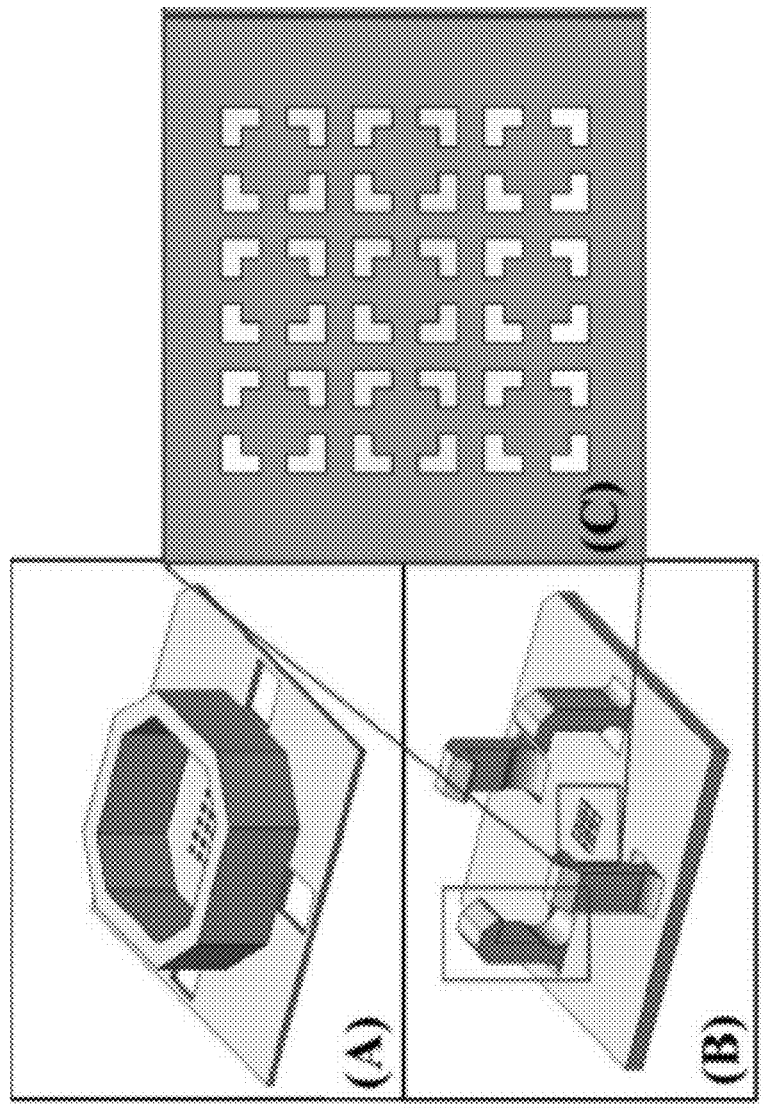
FIG. 20: Schematic of the first Modular MEA iterations. (A) The initial culture well design had four clipping slots to be integrated with the base (B). (B) The first base substrate had four clipping posts to integrate with (A) and plus-shaped via connects for ink casting. (C) Enlarged Schematic showing the plus-vias, which create a stable base for the laser micromachined electrodes, while enabling silver-ink connections to transition current to the bottom of the chip.
Figure 21:
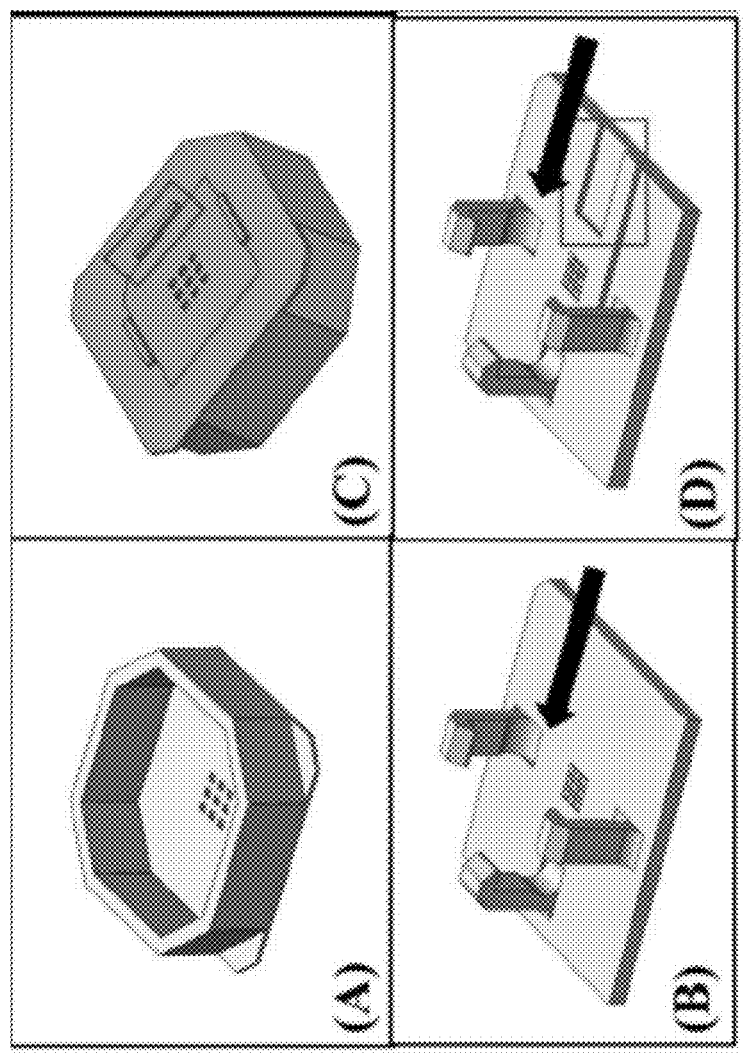
FIG. 21: Schematic of the first Modular MEA iterations. (A) The next culture well design, which lessened the footprint of the culture well considerably, and revised its integration to a slide mechanism for the substrate (B). The culture well is inserted in the direction of the arrow. (B) This substrate was very similar to the initial design, however it removed one of the clipping posts in favor of allowing the culture well to slide into place. (C) The next iteration of the culture well integrated raised partitions (highlighted in red) to better align with the new substrate in (D). (D) The next substrate included the plus-vias, but also included matching slots (highlighted in red) to fit the raised partitions on the culture well.
Figure 22:
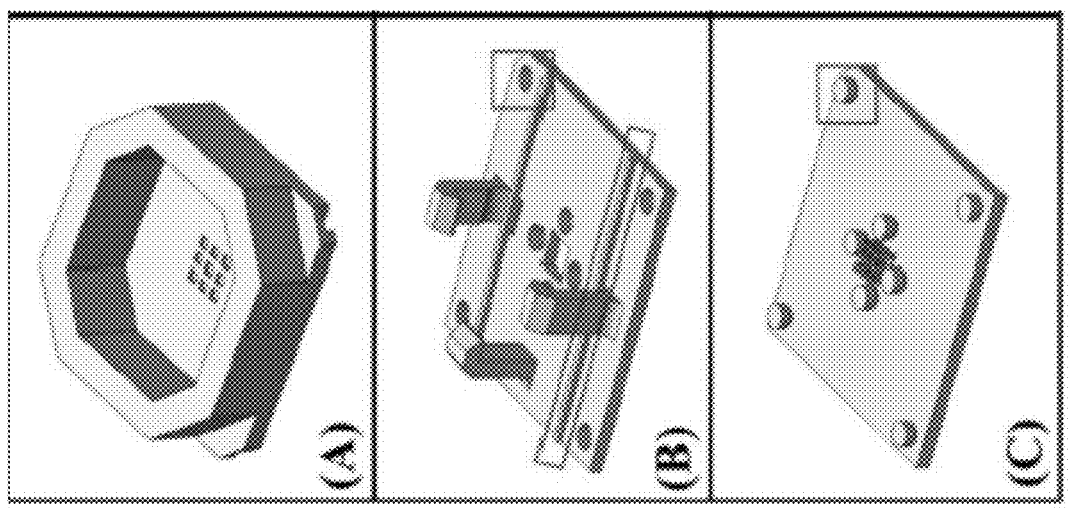
FIG. 22: Continuation of the Modular MEA schematic design iteration process. (A) The next iteration of the culture well, which thickened the sidewalls, and removed the raised partitions in favor of slide rail guides, to aid in the printing process. (B & C) The next middle and bottom micro pillar connect substrates added snap connector fittings and tabs respectively (highlighted in red) to aid in the flush connection of the two layers. The middle substrate in (B) also included the guide rails (highlighted in red) to accommodate the culture well in (A).

The fourth iteration needed to be 24 mm by 24 mm and at least 2 mm thick in order to match the design parameters of a custom in-house recording system. The initial design had two parts: four clipping posts on a substrate with "plus" shaped vias for connection to bottom-side traces, and a top chip with cut-outs for microneedle alignment and placement, and clip connect threading channels (FIG. 20). This design needed too much inherent flexibility for assembly (resulting in cracks and permanent bowing of the stainless steel material), and thus was modified to facilitate an assembly process flow that reduced these occurrences. The next design removed one of the clipping posts, and reduced the footprint of the culture well substantially by removing the extra material around the base of the culture well, and resizing it to 16 mm by 16 mm overall. The "plus" connect vias remained. This design introduced a sliding mechanism that would carry forward through many successive iterations of the Modular MEA design (FIG. 21(a & b)). The next iteration added slots in the base substrate and raised features on the bottom of the culture well, to ensure proper alignment of the assembly when interlocked (FIG. 21(c & d)). The "plus" shaped vias were then removed and replaced by simply a 3 mm by 3 mm cut out, to accommodate the "micro pillar via connect" feature. The pillar connects ensured verticality in the transitioned needles (aided in part by the Hypodermic Needle Array (Hypo-Rig) discussed later in section 4.6), and also ensured connectivity due to the inclusion of conductive ink coated vias inside of the micro pillars (FIG. 22).

Figure 23:
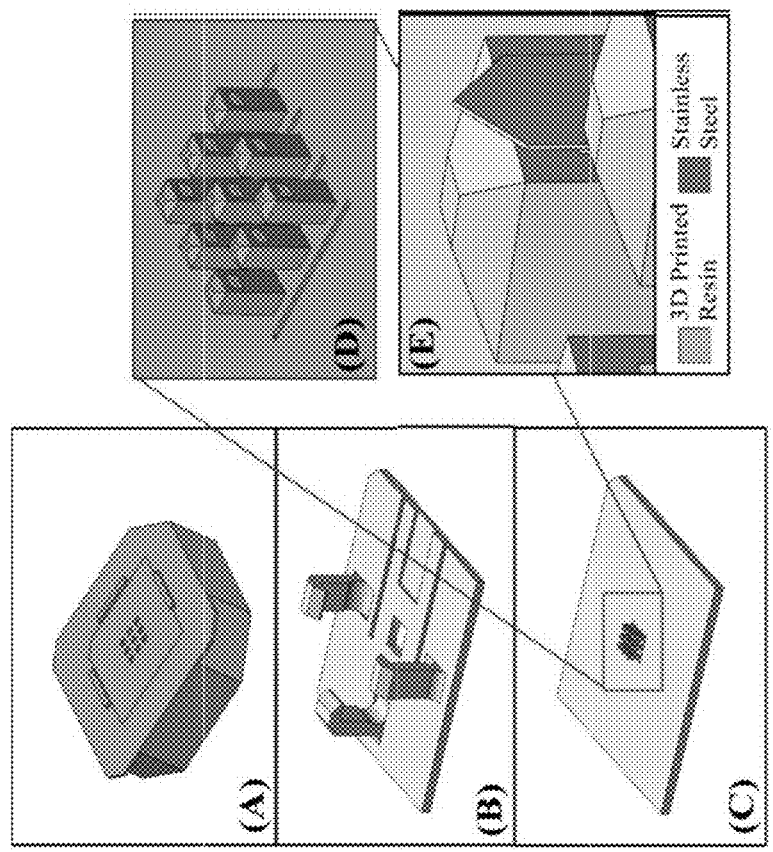
FIG. 23: Continuation of the Modular MEA schematic design iteration process. (A) The previous culture well, which was carried forward into the new three-part modular design. (B) The previous base substrate was transitioned to a middle layer substrate, and the plus-vias were removed in favor of a fitting slot for pillar connects on the bottom substrate. (C) First version of the micro pillar connect substrate, which transitioned the electrical contacts with silver-ink vias. (D) Enlarged schematic of the micro pillared substrate from (C). (E) Schematic representation of the desired connection between the steel and the silver-ink cast micro pillars.

Immediately after printing, the micro pillars were too soft to assemble, and so postcuring under a broad-spectrum UV lamp became necessary. The challenge with this step was that thicknesses of chips lower than 1.5 mm would warp due to the contraction of the internal polymer structures during UV post-curing. This would mean that the assemblies would no longer fit together properly. To solve this issue, snap connectors were introduced in the next iteration (FIG. 23). The rationale for the inclusion of this feature was to ensure an intimate connection of the pillar substrate to the culture well clipping substrate.

Figure 24:
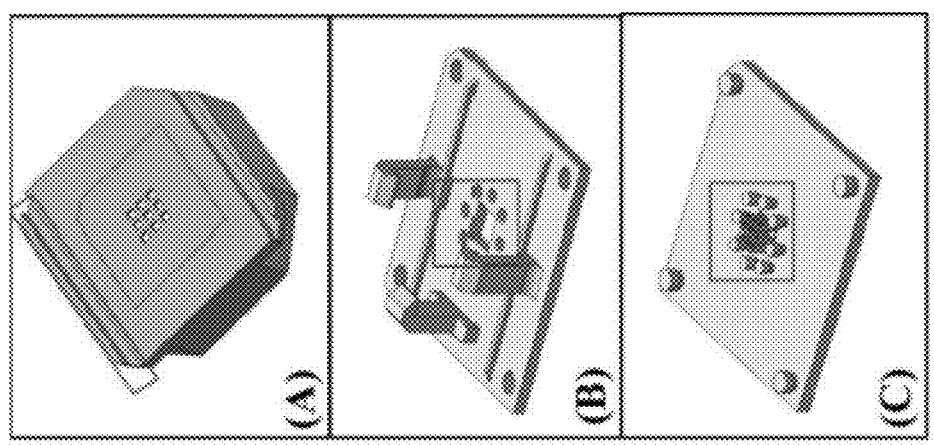
FIG. 24: Continuation of the Modular MEA schematic design iteration process. (A) Underside of the slide rail culture well design, highlighting the design choice of rail guides. (B & C) The next iterations of the middle and micro pillar connect substrates. The only change made here, was the addition of more snap connectors and fittings around the pillar connects to create an enhanced flush connection, which are highlighted.

When some of these newer designs were 3D printed and assembled for testing, other printing challenges arose, where the positive structures in the slide alignment chip prevented proper printing of the culture well. Recessed cut-outs were subsequently introduced in the culture well to facilitate better print resolutions, and the positive rails for the slide mechanism were moved to the clipping substrate (FIGS. 23B and 24A). Unfortunately, intimate connection of the three components was not observed after these changes were introduced to the 3D printed substrates, and so additional snap connectors were added to strengthen the connection (FIG. 24(*b* & *c*) and FIG. 25).

Figure 26:
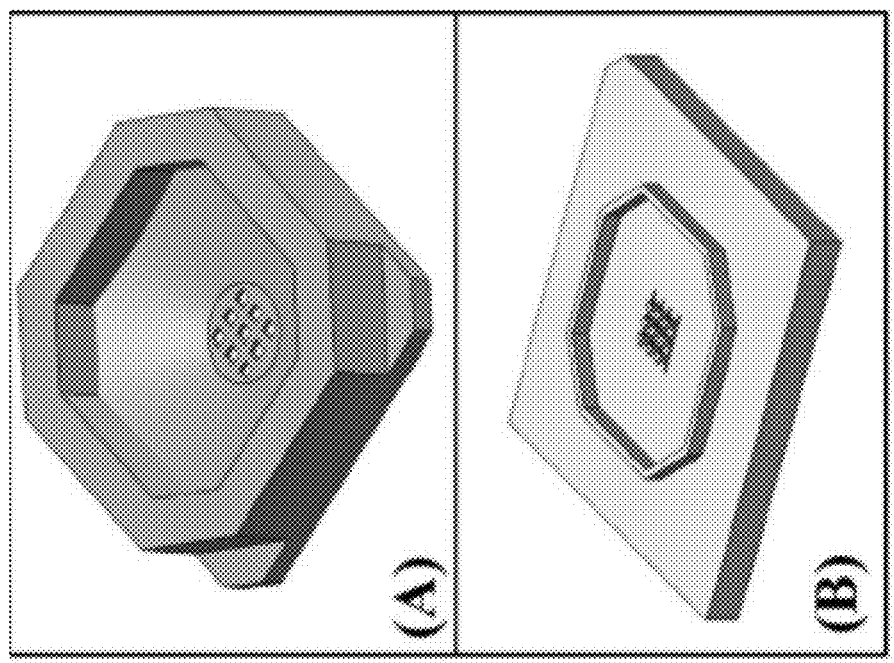
FIG. 26: Continuation of the schematic design iterations for the Modular MEA. (A) The culture well, which removed the rail guides, and replaced them with a slot for the raised alignment ring in (B). (B) The final iterations of the modular MEA, included just one base substrate with the micro pillar connect vias integrated and a raise clipping ring integrated. The fitting groove was mirrored on a version of the sloped culture well from (A).
Figure 27:
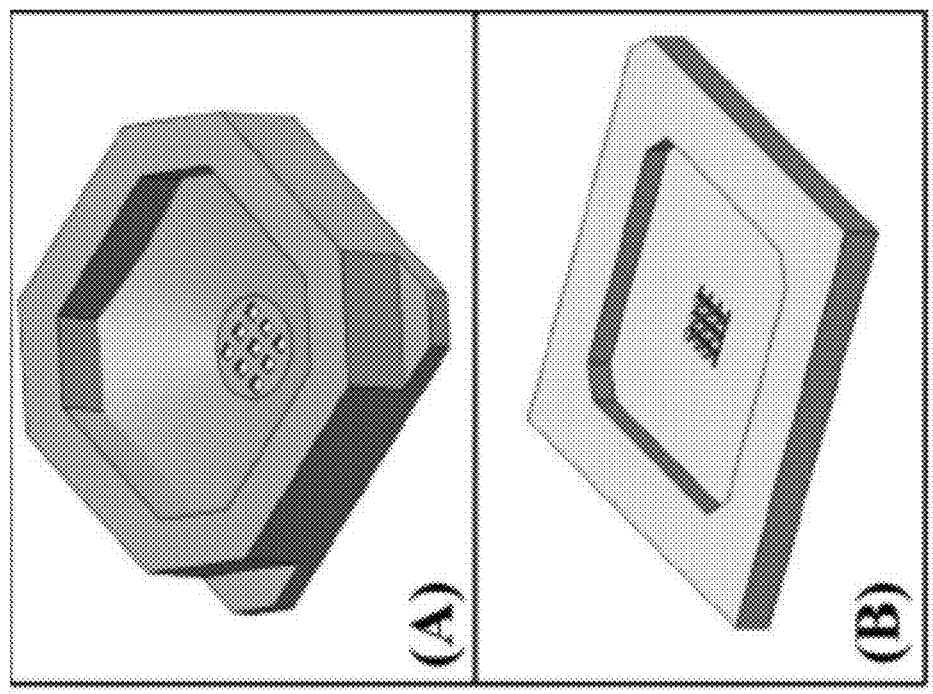
FIG. 27: Continuation of the schematic design iterations for the Modular MEA (A) The final iteration of the culture well, which removed the fitting roove or rail guides, and was fitted to a recessed substrate shown in (B). (B) The final micro pillar connect substrate, which included the recessed portion for a tight-fitting connection, and additionally contained laser micromachining guides for isolation of the microelectrode array after assembly.

Additionally at this point of the design evolution, the culture well was iterated to have a sloped basin feature (FIG. 25*a*). The rationale behind this change was to increase the stability of the final printed design, as well as to encourage potential cell populations, and organoids to diffuse toward the microelectrode recording sites. The Modular 3D MEA design was then reduced to two components: the sloped culture well, and the chip with micro pillars (FIG. 26). The next iteration contained a raised snap locking mechanism, fitted for an inverse cut on the bottom of the sloped culture well (FIG. 26(*a* & *b*)). After 3D printing, it was assessed that the fit was not as efficient as would have been necessary to ensure proper connection between the micro pillars and the stainless steel microneedle electrodes. The final iteration for this design was subsequently created, by designing a cut-out feature (16 mm by 16 mm) which was large enough to accommodate the culture well structure (FIG. 27). This feature provided significant stability in the design for both the post-curing process step, and for ensuring the micro pillar vias would be able to press through the stainless steel microneedle electrodes.

Figure 28:
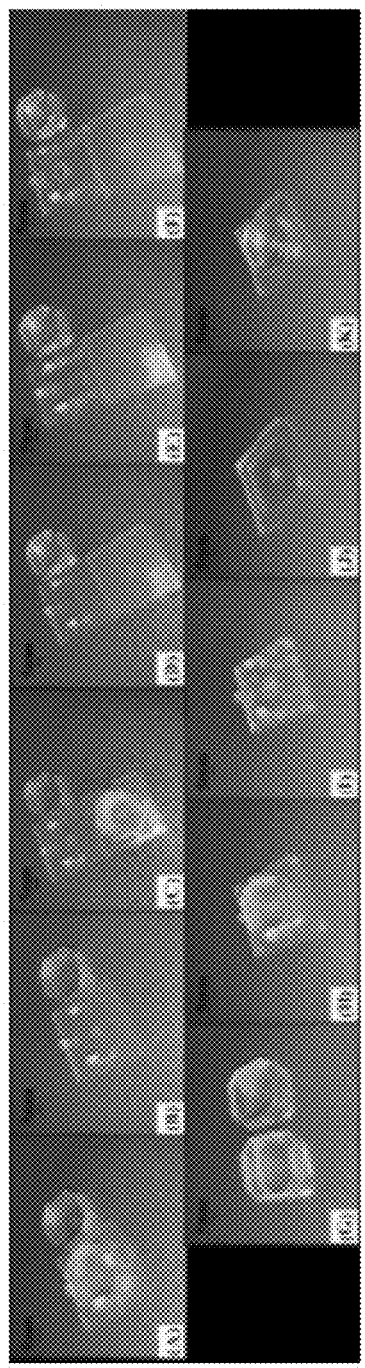
FIG. 28: Optical images of several of the design iterations. (A) The first iteration including the four pillar connects. (B) The next iteration with the plus-vias and a three pillar slide mechanism. (C) The iteration from (B) showing the full slide assembly. (D) The next iteration including the slide guides on the substrate and the including of the first pillar connect substrate. (E) The next iteration including the slide rails on the middle substrate. (F) The next iteration including the addition of the snap connectors for the substrates. (G) The change from a flat to a sloped culture well. (H) Image of the sloped culture well on the first snap connector iteration. (I) The next design change, including the addition of many more snap connectors. (J) The final pillar connect substrate, with the recessed fitting slot for the culture well. (K) The final modular MEA assembly design.
Figure 29:
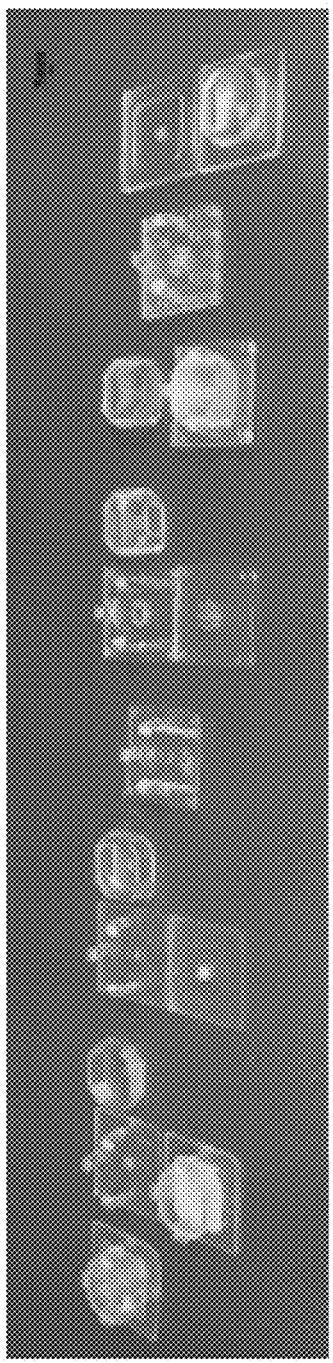
FIG. 29: Optical image of the representative progression of the printed device iterations shown in FIG. 46.

The printed versions of these schematic illustrations can be seen in FIG. 28, and the representative iterative progression over time can be seen in one combined image in FIG. 29.

Figure 30:
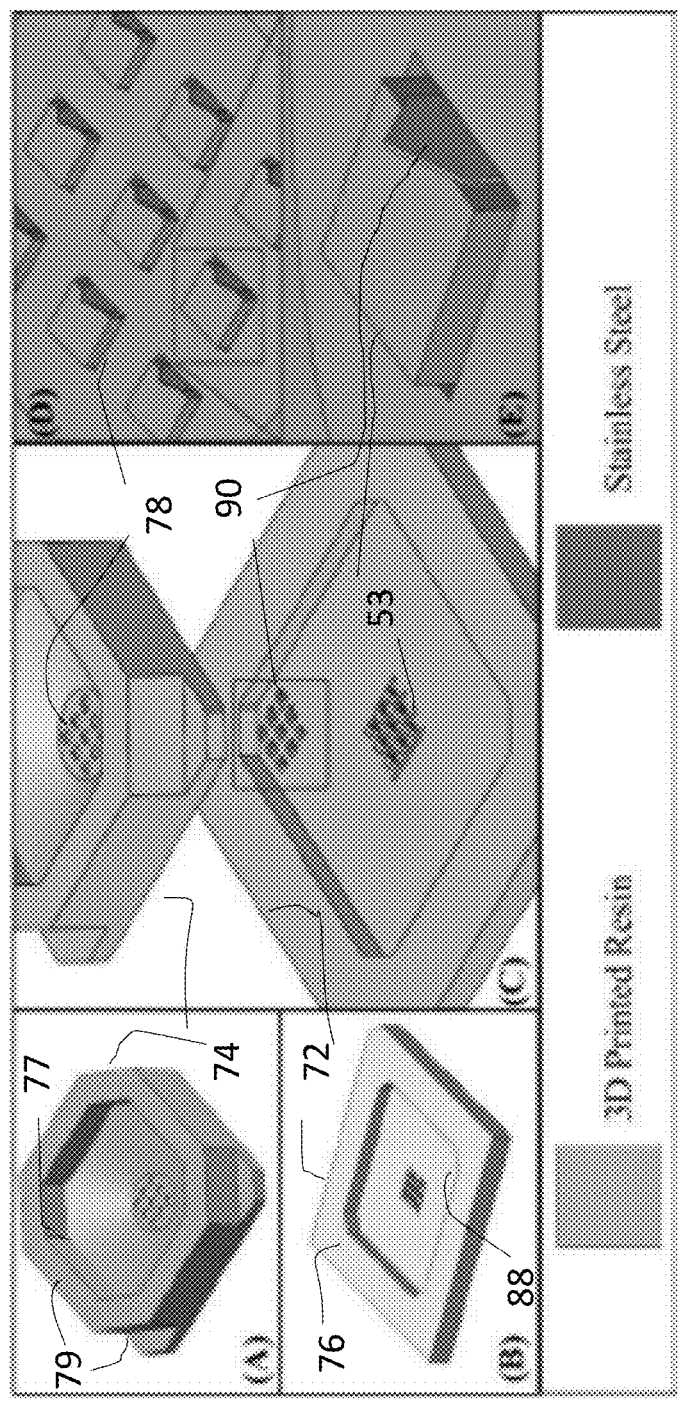
FIG. 30: Modular MEA process flow and characterization. (A) Final design of the sloped culture well. (B) Final design of the micro pillared substrate, with recessed cut for the culture well in (A). (C) Exploded schematic of the parts from (A & B), with the 3×3 array of steel microneedle electrodes highlighted between the layers. (D) Enlarged schematic of the assembled modular MEA, showing the steel microneedle electrodes emerging from the partitions in the culture well. (E) Further enlarged schematic of (D) which shows the flush connection of the electrodes with the micro pillars.

The final version of iteration 4 deviated the most from the other iterations as previously mentioned (FIG. 30). The 3D printed packaging substrate was designed still with Solidworks 3D CAD software (Dassault Systems, 2016), but was 3D printed using commercially available Pro3dure GR-1 clear resin (Pro3dure, Germany) on the Asiga MAX X UV27 DLP 3D printer (ASIGA, Australia), with a wavelength of 385 nm (FIG. 30(*a* & *b*)). The 3D printer was changed from the Formlabs SLA printer, due to the resolution demands of this new design. The 27 μm pixel size was far better suited to resolving the finer features than the μSLA 140 μm laser spot. The base substrate dimensions were: 24 mm width, 24 mm length, and 2 mm thickness. Cut-outs in the base substrate were: 16 mm width, 16 mm length and 1.3 mm depth.

The culture well was designed to be of the same dimensions as the cut-out in the base structure. The height of the culture well was 8 mm. Micro pillars (500 μm width, 500 μm length, and 400 μm height) were incorporated in the center of the cutouts on the base substrate, with a 300 μm width by 300 μm length channel defined through the micro pillars, 300 μm high.

These channels ended in an inverted "L" shape to create vias to connect with the stainless steel microneedle electrodes (FIG. 30(*d* & *e*)). Four laser-scribe vias (150 μm by 3 mm) were designed between the rows of micropillars, to allow full singulation of the 3×3 electrode array after assembly.

The culture well was designed, to be 16 mm in width by 16 mm in length, with a height of 5 mm, and a matrix of 550 μm by 550 μm holes centrally aligned (can be accommodated as per the design of the 3D MEA grid). The width of the culture well side walls was designed to be 2 mm thick.

The substrate and culture well were subsequently rinsed twice with isopropyl alcohol (IPA) (Sigma-Aldrich, USA) for 10 minutes each and air dried, after printing. The culture well and base substrates were post cured in a broad spectrum UV post-curing chamber (ASIGA, Australia) for 3 minutes to ensure the rigidity of the parts for assembly. The pillar via connects were cast with Epo-tek® EJ2189 silver-ink (Epo-Tech, USA), across a Kapton® mask and the ink was allowed to cure for 36 hours at 45° C., to minimize warpage of the resin. After curing, the excess ink was removed by simply peeling back the Kapton® stencil mask. 30 nm Gold (5N, 57 mm by 0.2 mm Au target; Ted Pella, INC., USA) traces to connect to the vias on the backside were defined by sputter metallization (Quorum Q150T Plus; Quorum Technologies LTD., UK), through a Kapton® stencil mask, under the following deposition conditions: 20 mV, and 13 nm/min deposition rate.

Figure 25:
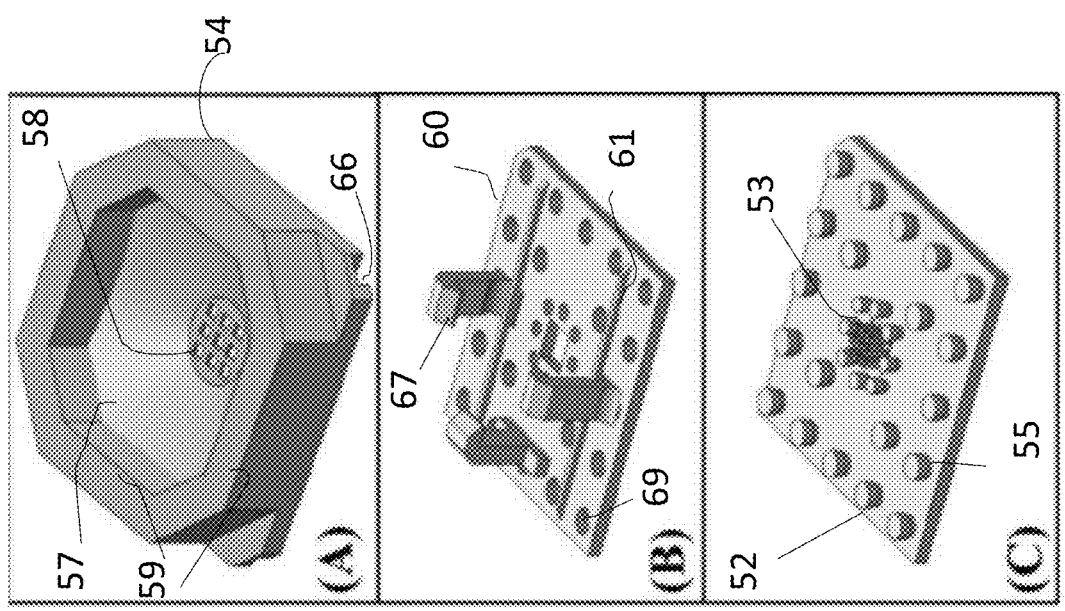
FIG. 25: Continuation of the schematic design iterations for the Modular MEA. (A) The next iteration of the culture well included the change to a sloped geometry to aid with the stability of the printed design, as well as to create a funneling effect for biological plating of cells. (B & C) The next iteration of both the middle and bottom micro pillar connect substrates added many more snap connectors and fittings in an effort to create a better fitting of the two pieces.

FIG. 25 is referenced to describe MEA platform system that has three modular components and implements micropillars. One skilled in the art will understand that the descriptions relating to FIG. 25 will illuminate the components and operation of the embodiments shown in FIGS. 22-25. Platform Iteration 50 shown in FIG. 25C includes a first base 52 that includes an array of micro-pillars 53. The first base 52 also also includes a number of snap-fit connectors 55. FIG. 25A shows a second base 54 that includes a plurality of apertures 58 and defines a culture well 57 with walls 59. FIG. 25B shows a third base 60 that has defined therein a plurality of holes 69 for receiving the snap-fit connectors 55. Third base 60 also include slide rails that 61 that upon which grooves 66 defined in the bottomside of the second base 54. Also, provided on the topside of the third base 60 are a plurality of clipping posts 67 for engaging the culture well walls 59 as the second base 54 slides onto the third base 60.

Figure 53:
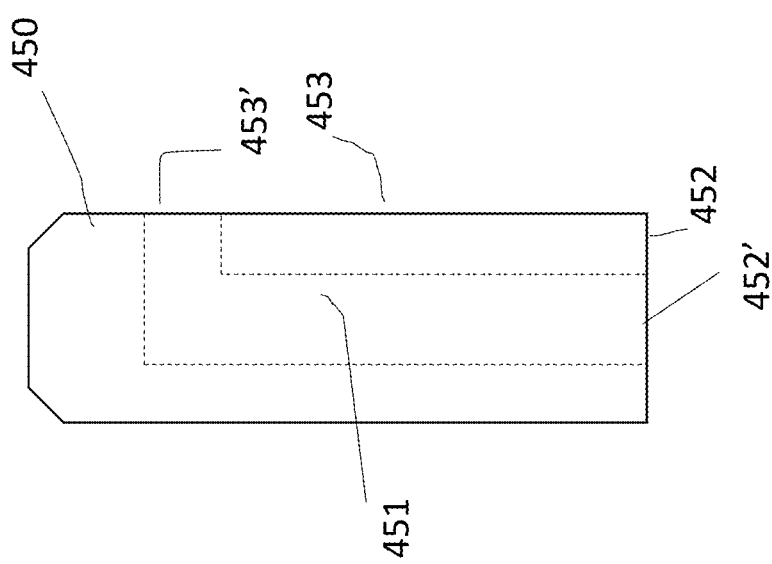
FIG. 53 shows a side view of a micro-pillar that illustrates a via disposed therein.

Provided in FIG. 53 is an illustrative example of a micro-pillar 450 such as the micro-pillars 53 shown in FIG. 25, and related micro-pillar structures shown in FIGS. 22-24 and 26-30. The micropillar 450 includes a via 451 with a bottom opening 452' at a bottom end 452 of the micro-pillar structure and a side opening 453' at the side wall 453 (see FIG. 53) As described above, a conductive material is disposed within the via such that a conductive connection can be made from a conductive structure at one level of a layered assembly to another level of layered assembly. As will described further below with reference to FIG. 30, the micropillars of a given base will conductively interact with a microneedle at the side opening and will conductively interact with traces, connections, pads, etc. (not shown) under the first base.

FIG. 30 shows another iteration 70 that has a first base 72 and second base 74. The first base 72 includes a plurality of micro-pillars 53 (see FIG. 53) defined thereon. Also defined on a top surface 76 of the first base 70 is a recess 88 for receiving the second base 74. The second base 74 includes a culture well 77 with walls 79 and a plurality of apertures 78 defined therein configured for receiving micro-pillars 53 and micro-needles 90. As shown in FIG. 30C, a plurality of microneedles are aligned with the apertures 78 and the second base 74 is positioned in the recess 88 whereby the apertures 78 individually receive both a micro-pillar 53 and microneedle 90 as is shown in FIGS. 30D and E.

Metal Micro Fabrication and Insulation

Figure 31:
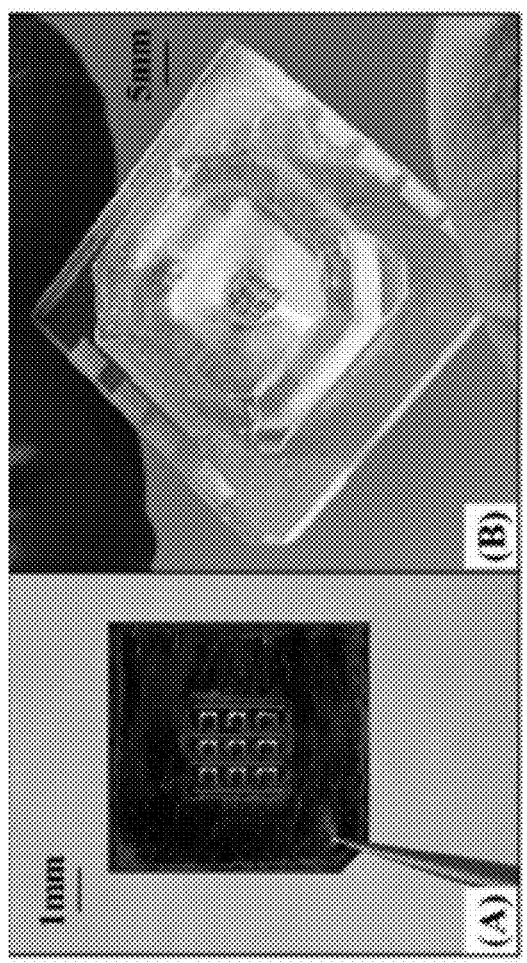
FIG. 31: (A) Optical image of the 5 mm×5 mm laser micromachined steel array. The 3×3 electrode pattern can be observed, with the first of the isolation lines between each electrode. (B) Optical image of the fully assembled Modular MEA. The deposited traces can be seen on the back of the device, along with the fibers showing the spin coated polystyrene insulation. The additional yellow which can be seen on the bottom of the culture well is Kapton® tape for aligning the steel array on the culture well, prior to assembly.

The 3D metal microelectrodes were machined from 12.5 µm thick 316L stainless steel (Trinity Brand Industries, USA) using the QuikLaze 50 ST2 laser micromachining system (Eolite Lasers, USA) to define a 3×3 (and later 8×8) grid of planar (2D) microelectrodes (electrode dimensions: 300 µm width; 350 µm height; 1 mm pitch) with 1064 nm wavelength IR light (6 mJ power, and 50 Hz repetition rate) (FIG. 31a). The planar electrodes were subsequently acid pickled in a solution of DI Water (80 wt %), 70% HNO3 (11 wt %), 49% HF (9 wt %) at 50° C. for 1.5 minutes with sonication, to remove oxide impurities, smooth, and prepare the electrode surface for nanomaterial deposition. The electrodes were transitioned from 2D to 3D by using the custom fabricated Hypo-Rig, to ensure a precise and controlled angular spread across the array (described in section 4.6). The array was singulated into individual microelectrodes using the same laser micromachining parameters described above, by cutting all horizontal scribe lines during the initial laser micromachining process, and fully isolating each electrode from the back using the included long vias as mentioned previously. This method was possible due to the multimodality of the laser. The 3D printed resin does not absorb the IR wavelength, and thus was not damaged.

A 4.5 µm thick, 10% polystyrene (PS) in Tetrahydrofuran (THF) (w/v) (Sigma Aldrich, USA) layer was spin-coated (5000 rpm, for 30 seconds) over the top of the electrode array to define a 3D insulation. Controlled burst ablation laser micromachining at an UV wavelength of 355 nm (0.4 mJ power, and 4 singular bursts per electrode), was used to selectively ablate the microelectrodes and define the microelectrode recording sites. The polystyrene coating applied using conformal 3D spin-coating, could additionally be replaced by deposition of Parylene-C, as it is not only biocompatible, but also provides strong mechanical adherence to most materials [168]. The PS insulation was selectively laser micromachined to reveal the electrode tips using 355 nm wavelength UV light (3.6 mJ power, and 50 Hz repetition rate). Pulsed electroplating was performed as described in Section 4.3.2. The fully assembled device can be seen in FIG. 31b, where the sheen on the culture well shows the presence of the conformal PS coating layer.

Characterization

Figure 32:
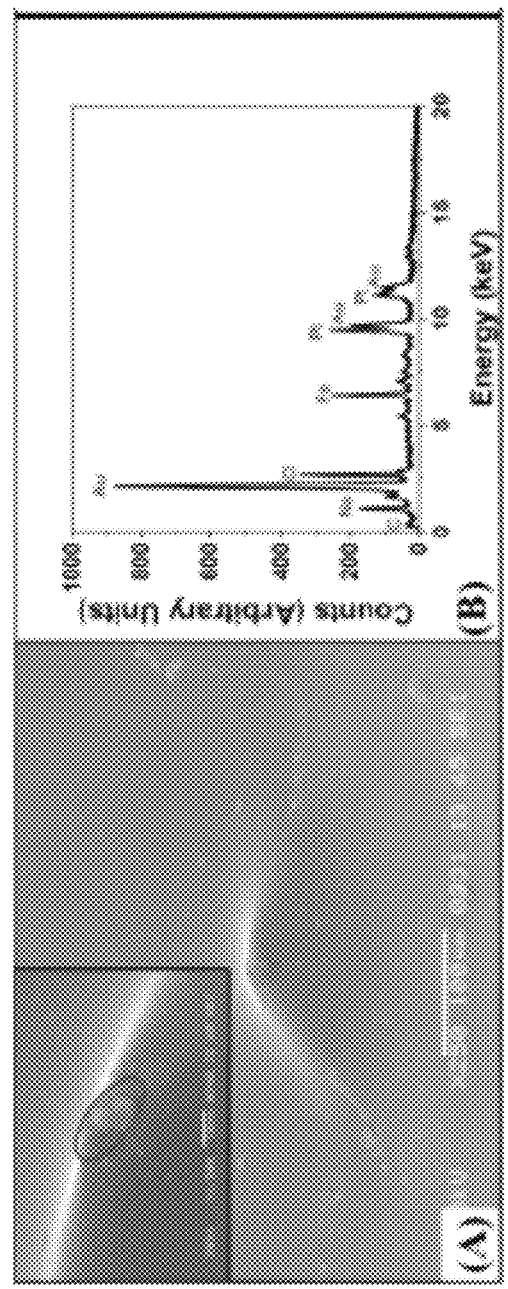
FIG. 32: (A) SEM image of the Nano-Porous Platinum plating. After initial controlled burst ablation of the electrode tip, to remove the insulation, the growth of the N-P Pt increases the total surface area of the microelectrode, without adding to the projected electrode area. The inset shows a closer view of the Pt electrode surface. (B) EDS spectrum of the electrode tip from (A). The high presence of Au is expected (due to the sputtering for sample preparation), and the expected peaks for Pt can be clearly observed, confirming the plating of the nano-porous material.
Figure 33:
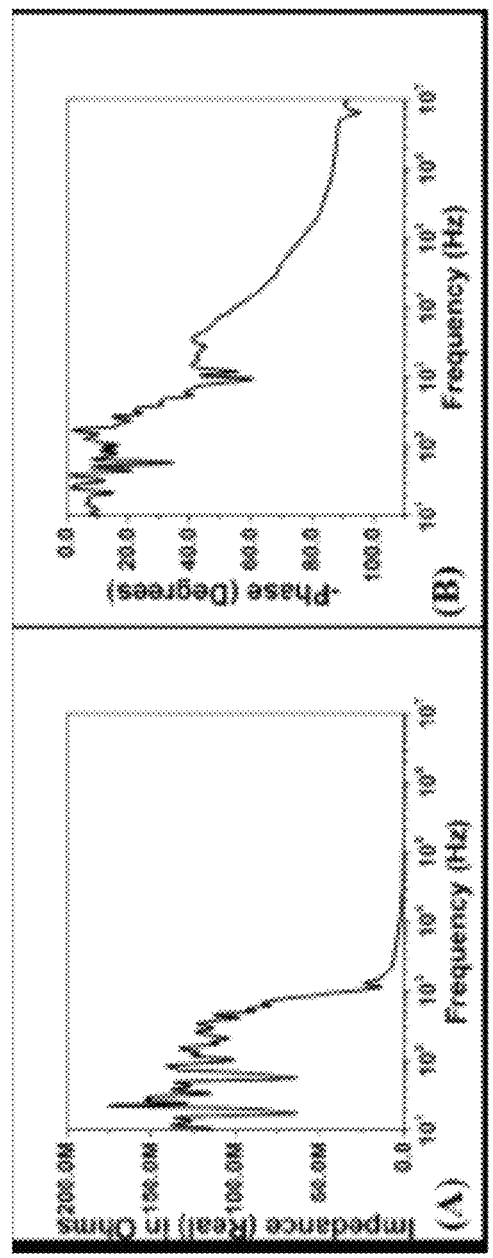
FIG. 33: Modular MEA in situ process characterization. (A) Full spectrum impedance of the initial ablation of the modular MEA electrode recording sites. (B) Full spectrum phase of the initial ablation of the modular MEA electrode recording sites. The 1 kHz impedance and phase values of 25 MΩ and −50° indicate a microelectrode profile, but one not suited for electrophysiological measurements.

FIG. 32a demonstrates the platinized electrode tip of the final Modular MEA design, which is confirmed by EDS in FIG. 32b. FIG. 33 contains the full spectrum impedance (a) and phase (b) of the initial ablated state of the steel electrode, before N-P Pt electroplating. The slight MEA signature indicated the opening of the electrode recording site beneath the insulation coating, but the noise which is evident in the lower frequency range, along with the sharp drop in impedance at the 1 kHz point of 25 MΩ, and the phase value of −50°, indicate this is not yet suitable for electrophysiological measurements.

Figure 34:
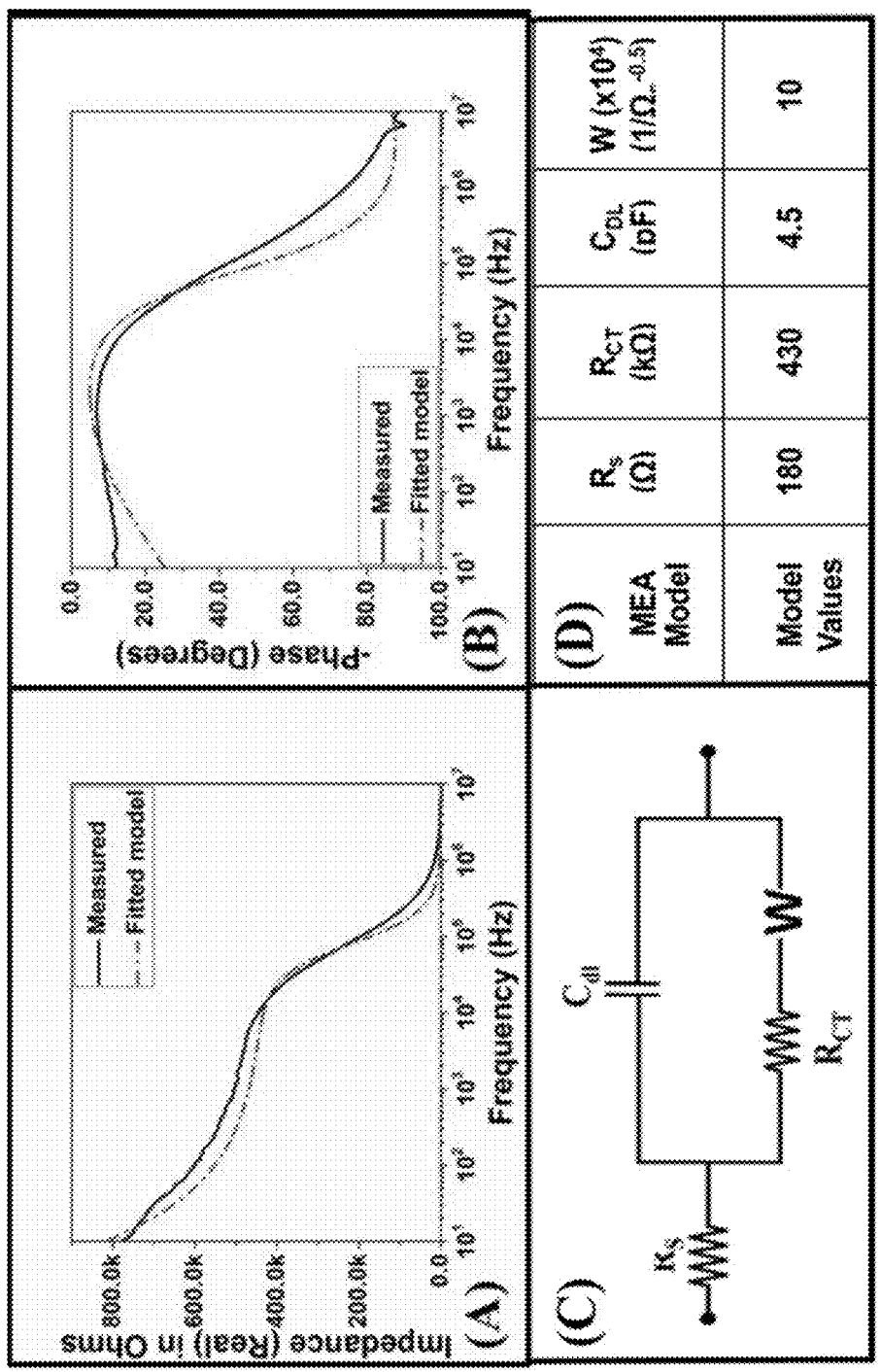
FIG. 34: Modular MEA in situ process characterization. (A) Full spectrum impedance of the platinized modular MEA electrode recording sites. The red line shows the fitted model for the impedance spectrum of the electrodes. (B) Full spectrum phase of the platinized modular MEA electrode recording sites. A fitting for the Phase of the electrodes is shown here as well. The 1 kHz impedance and phase values of 500 kΩ and −9° indicate a much more suitable microelectrode for biological applications and demonstrates the ability of N-P Pt electroplating to enhance the fabrication of microelectrodes in this fashion. (C) Randels circuit equivalent model for the fitted models shown in FIG. 49. (D) Associated values with the Randels equivalent circuit for the fitted model.

The data in FIG. 34 represents the full spectrum impedance and phase of the N-P Pt electrode recording site (shown in FIG. 32a). The drastic change in impedance, with a 1 kHz value of 500 kΩ, is due to the increased surface area which stems from the convoluted surface geometry of nanomaterials such as Pt. The phase also indicates this electrode to be better suited to electrophysiological measurements, with a 1 kHz value of −9°, and both contain a much better SNR than the bare steel recording site alone. FIG. 34c once again contains the Randels equivalent circuit for the fitted models in FIG. 34 (a & b), and (d) contains the relevant extracted circuit parameters previously discussed in chapter 3.

Example 5: Hypodermic Needle Array (Hypo-Rig)

Figure 35:
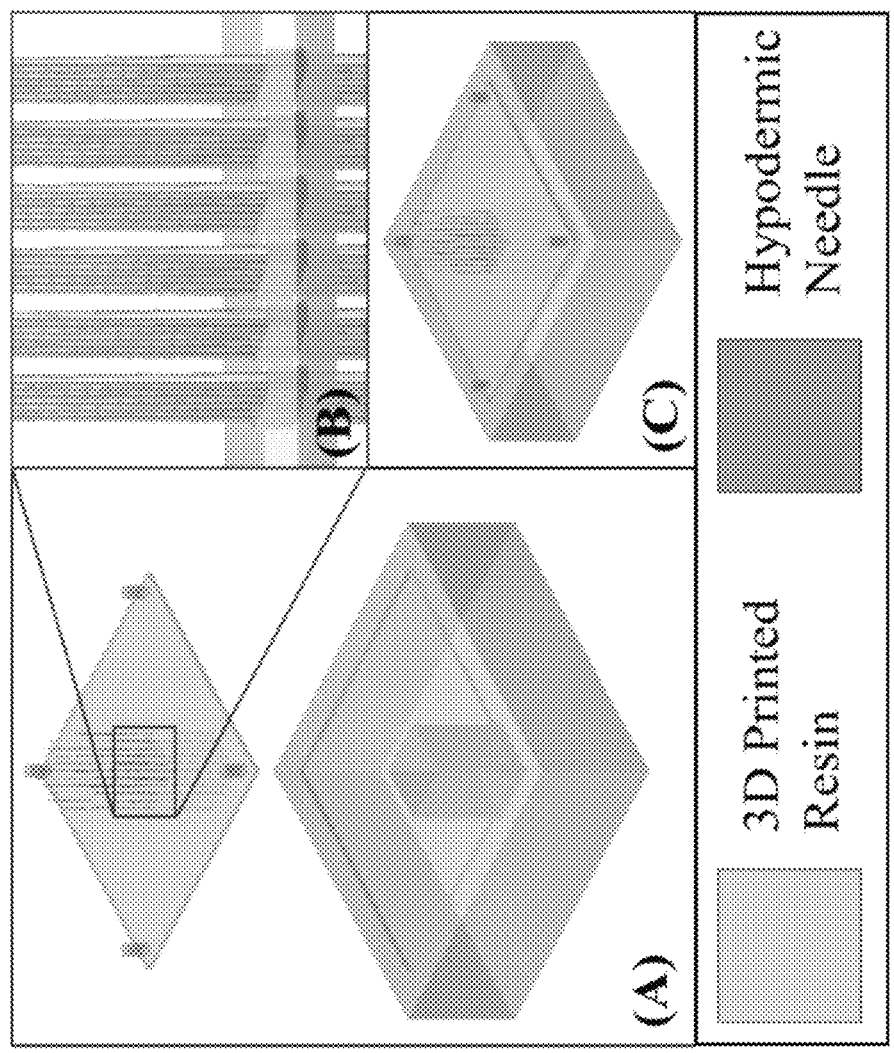
FIG. 35: Schematic of the assembly of the Version 1 and 2 Hypo-Rig base. (A) A 3D printed base with grooves for fitting the hypodermic needle holding array. (B) Enlarged schematic of the hypodermic needle array showing the alignment of the needles in the 3D printed array. (C) Schematic of the fully assembled base, with alignment pegs for pressing the steel.

The Hypodermic Needle Array (Hypo-Rig) was designed to better facilitate the transition of micromilled or laser micromachined 2D electrodes to 3D. The intent of the engineered design was to have a more consistent electrode angular spread (defined as the angle between the 3D transitioned microneedle and the base of the stainless-steel remaining), and to have this spread as close to 90° as possible. To accomplish this, an initial Hypo-Rig base structure (200 mm by 20 mm, and 10 mm thick) was designed using Solidworks 3D CAD software, and 3D printed using the commercial clear resin on the Formlabs Form 2 µSLA printer (FIG. 35a). The base was designed thicker in order to provide a more stable structure for application of transitionary forces.

The base also contained a 5 mm by 5 mm and 5 mm deep reservoir for inserting the needle array holding tray (FIG. 35a). This part was designed similarly, but was 20 mm by 20 mm and 1.5 mm thick, with a centrally aligned 6×6 array of 310 µm diameter holes for inserting the needles (FIG. 35b). The full schematic of the fabricated base can be found in FIG. 35c.

Figure 36:
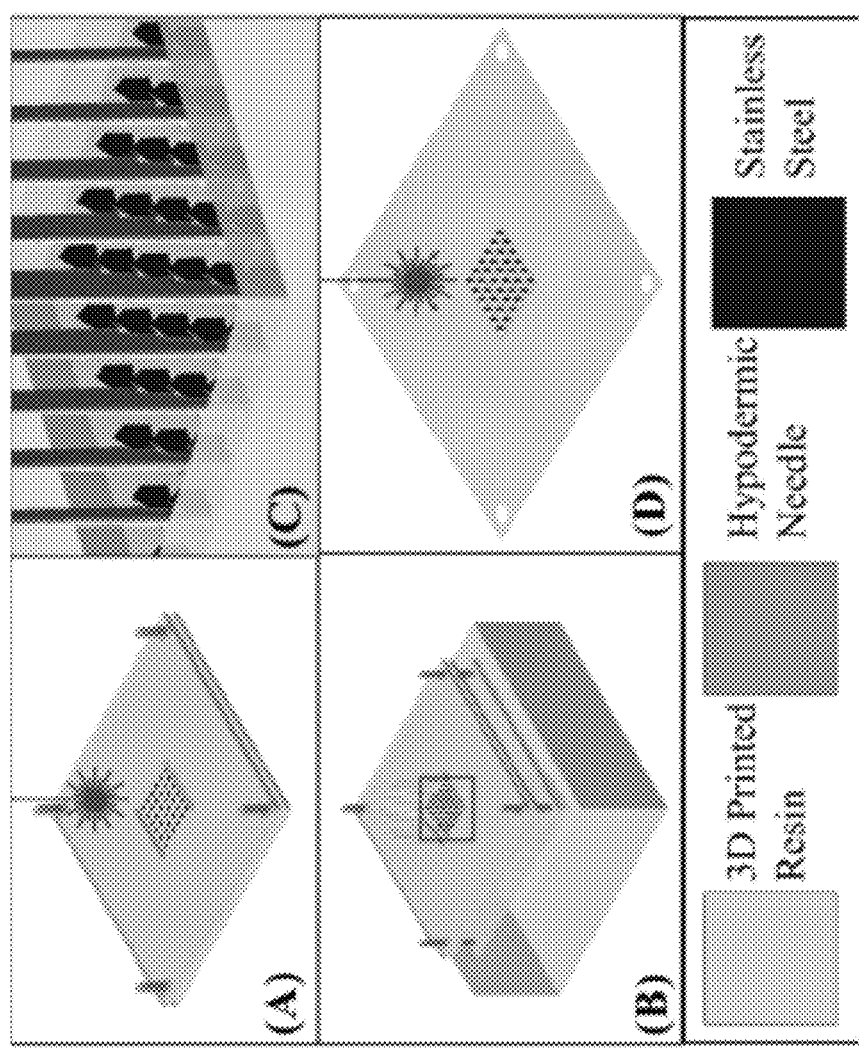
FIG. 36: Schematics of the preparation of the steel sheet for transitioning. (A) Schematic of the steel array sheet holder. IR laser micromachining is used to define the planar array of microneedle electrodes. (B) Schematic of the placement of the array holder and steel from (A) on to the Hyporig base substrate. (C) Enlarged schematic of the highlighted portion of (B), showing the needles transitioning the electrodes to their final 3D conformation. (D) Schematic of the released steel sheet, with transitioned electrodes, which are subsequently released from the overall steel sheet by further IR laser micromachining.

In iteration 1 and 2, the hypodermic and dispensing needles respectively, were fitted into integrated, 3D printed alignment slots in the base. The needles were trimmed and secured with 353ND two-part epoxy (Epo-Tech, USA). The epoxy was cured at 60° C. for 24 hours. The second part of the design was a sandwiched holder for the stainless steel sheet with the 2D microneedle electrode cut-outs (FIG. 36a). The full steel array was placed precisely with the aid of alignment structures in the sandwich press, and this step lessened the probability that the needles or the bulk stainless steel would break when pressed on the rig (FIG. 36 (b & c)).

Figure 37:
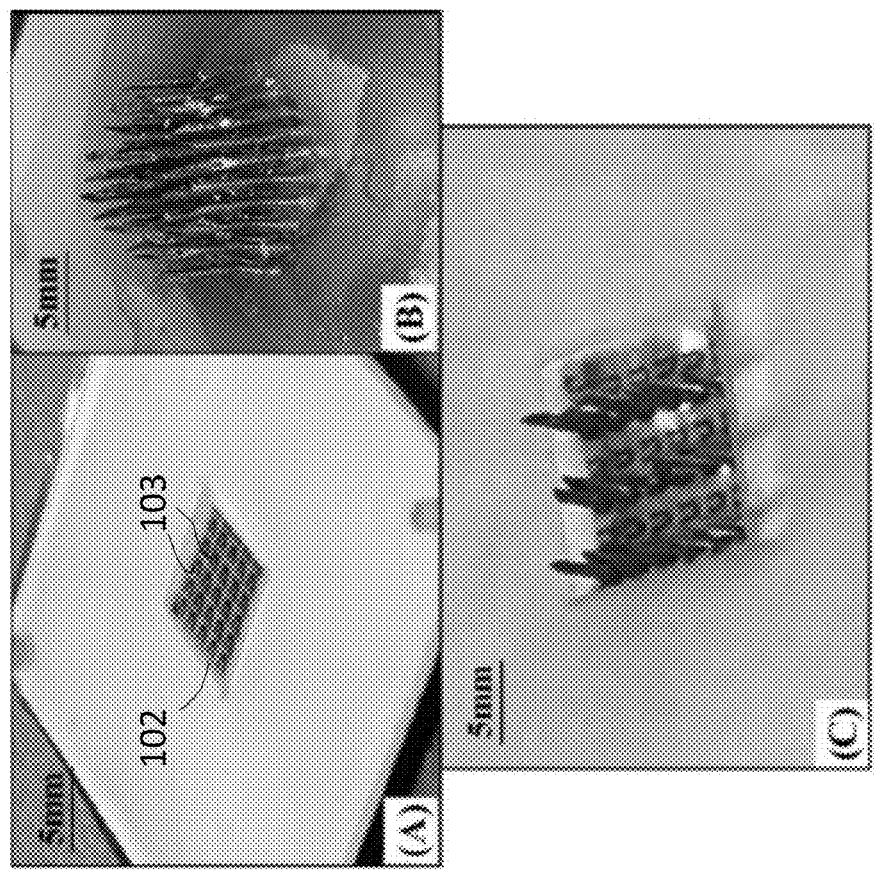
FIG. 37: Optical images of the Version 1 Hypo-Rig. (A) Optical image of the laser micromachined steel array on the assembly, before transitioning on the Hypo-Rig. (B) Optical image of the version 1 Hypo-Rig. The hypodermic needles were attached with epoxy into the 3D printed base, however it was difficult to orient all of the needles similarly, and the Epoxy was not uniform. (C) Optical image of a half-array iteration of the Version 1 Hypo-Rig during the transitioning process.
Figure 38:
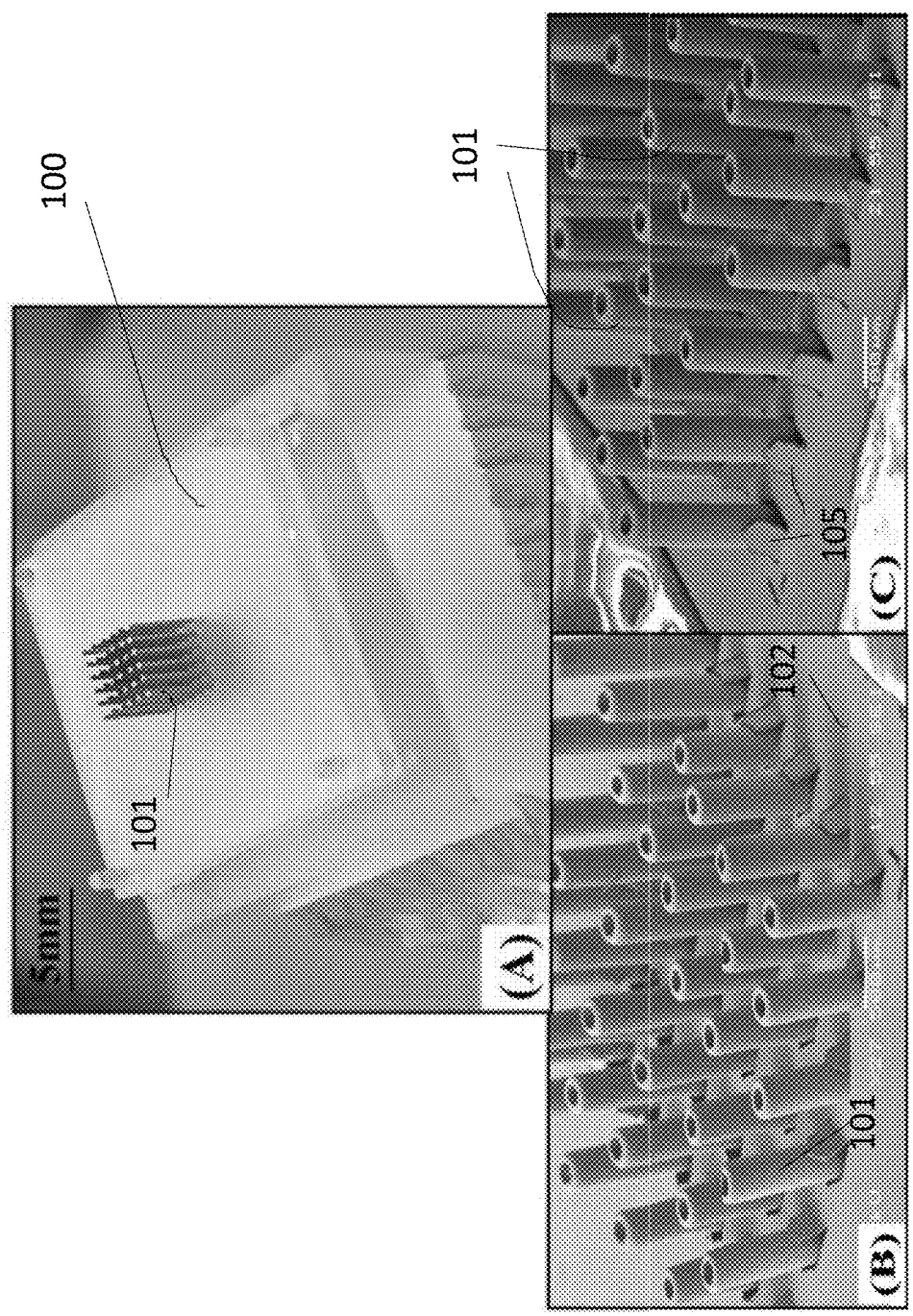
FIG. 38: Version 2 Hypo-Rig with dispensing needles. (A) Optical image of the Version 2 HypoRig, with the new array of dispensing needles. (B) SEM image of the Version 2 Hypo-Rig during the transitioning process. (C) Alternate angle of (B) highlighting the precision nature of the technique.

The hypodermic needles in the iteration one design were standard 30G hypodermic needles (310 µm outer diameter, and 150 µm inner diameter) (EXEL Int., USA), and the goal was to use the sharp tips of the needles as the smallest possible point of distributed force application to transition the needles without minimal stress applied to the MN structures (FIG. 37). These were later replaced with 30G dispensing needles (310 µm outer diameter, and 150 µm inner diameter) (BSTEAN™, USA), because it was observed that a flatter surface for the application of force, provided less resistance to the removal of the rig upon release of the needle arrays (FIG. 38). The other rationale for the change in hypodermic needles, was because it was difficult to orient all of the hypodermic needles in the same way during the fabrication process.

Figure 39:
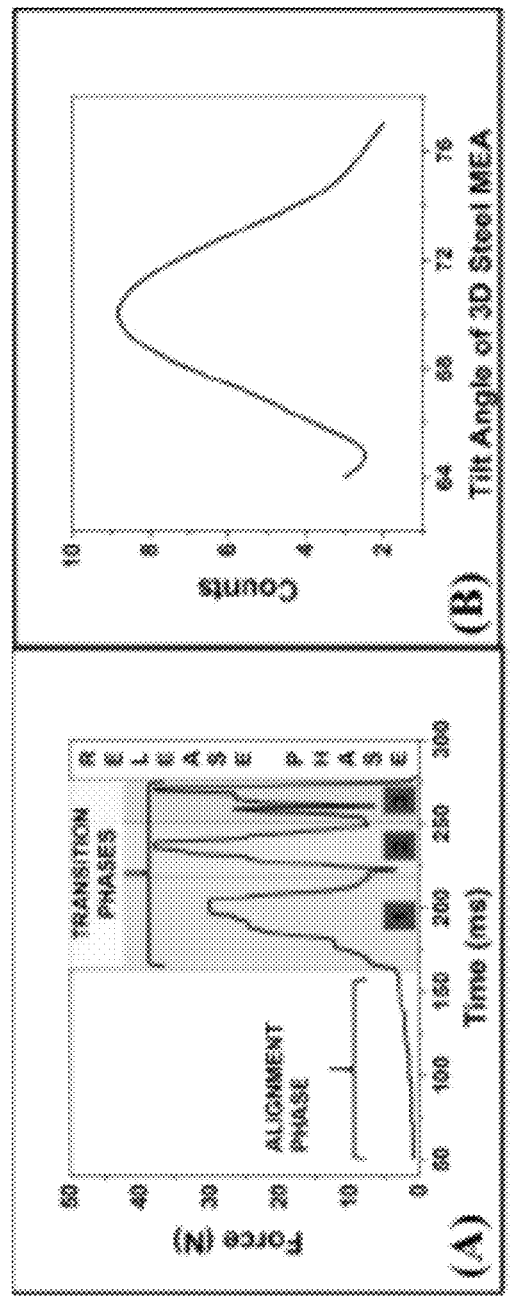
FIG. 39: Quantification of the Version 2 Hypo-Rig performance data. (A) Force vs. Time graph showing the various phases and associated results when using the Hypo-Rig. The force data was generated from a Force Sensitive Resistor. Each of "Transition" phases (1-3) demonstrates the force required to transition the full array into the final MEA conformation. Three press cycles were completed so that all needles were pressed to optimized tilt angles depicted in (B). The release phase shows the abrupt drop in force as the MEA is released from the Hypo-Rig. (B) The tilt angle data was collated from SEM data taken of N=36, showing a tight Gaussian distribution of electrode angles centered at 70°.

FIG. 39 shows the quantitative characterization of the assembly process during application of the second iteration of the Hypo-Rig. FIG. 39a represents alignment, transition, and release phases of utilization of the Hypo-Rig to transition the 36 microneedle electrodes from 2D to 3D. The maximum force required to transition the steel was 40N, and three separate press cycles were performed to ensure maximum conversion efficiency. The final Gaussian distribution of the transitioned 3D MEA needles centered around 70°, after the alignment and transition processes with the Hypo-Rig (FIG. 39b). Even though the goal was achieving perpendicularity with the transition, ~70° transitioned 3D microneedle electrodes are useful for electrophysiological measurements in 3D cellular constructs, as an alternative to traditional silicon manufactured microneedle microelectrodes. Beam theory calculations and COMSOL Finite Element Analysis techniques are necessary to fully characterize this process in the future. As a whole, the Hypo-Rig leads to customization and scalability of micromachined 3D MEA designs, resulting in arbitrary heights of the 3D structures; a major advantage over methods such as bulk electrodeposited "cauliflower" microelectrodes.

Figure 40:
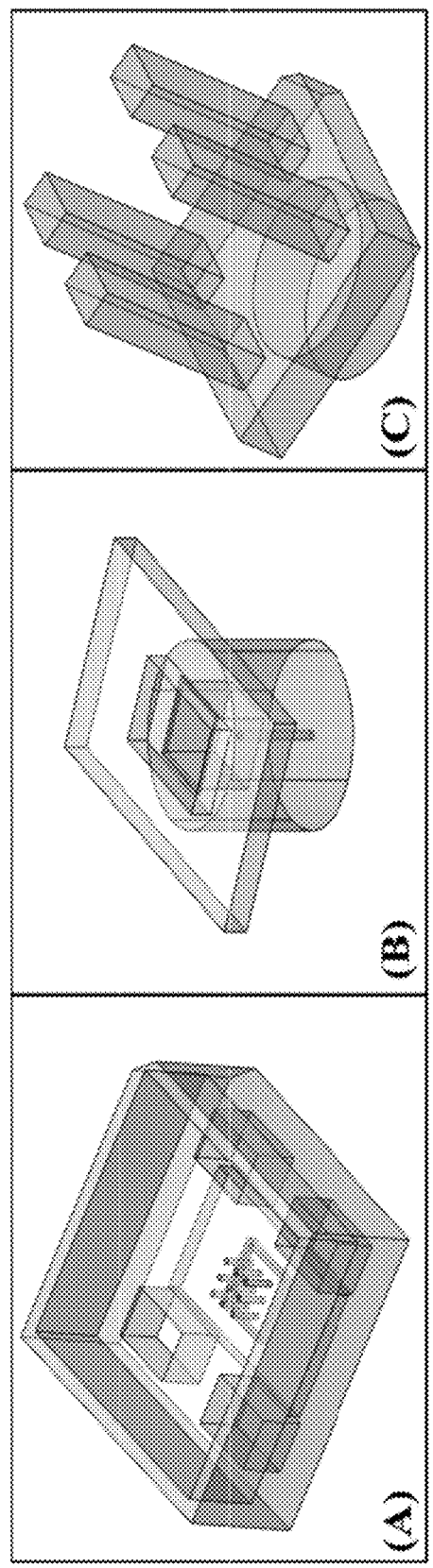
FIG. 40: Process flow for the Version 3 Hypo-Rig. (A) Schematic of the new base for the rig. The new design was developed to fit 16 mm×16 mm culture wells with metal microfabricated needles needing transitioning to 3D. Integrated slots allow for quick and even release of the transitioned array. (B) Schematic for the back cap to the Version 3 rig. The cap covers any exposed needles, and provides a flat surface for an even force distribution during the transitionary process. (C) Schematic for the release press.

The third iteration of the Hypo-Rig assembly was designed and developed using the Asiga DLP 3D printer (Asiga Ltd., Australia). Again, the switch was made to this DLP printing method for the higher fidelity structure printing capability of the platform. The design schematics of the fabrication and assembly are shown in FIG. 40. The higher resolution of this printer as compared to the μSLA printer, allowed a more compact design to be implemented. A smaller 16 mm by 16 mm rig was designed in Solidworks 3D CAD software (Dassault Systems, 2016), and printed using Pro3dure GR-1 clear resin (Pro3dure, Germany) on the Asiga MAX X UV27 DLP 3D printer (ASIGA, Australia), with a wavelength of 385 nm (FIG. 40($a$ & $b$)). A "release press feature" was similarly designed to aid with the removal of the electrode array after a fully pressing the MN array (FIG. 40$c$).

Figure 41:
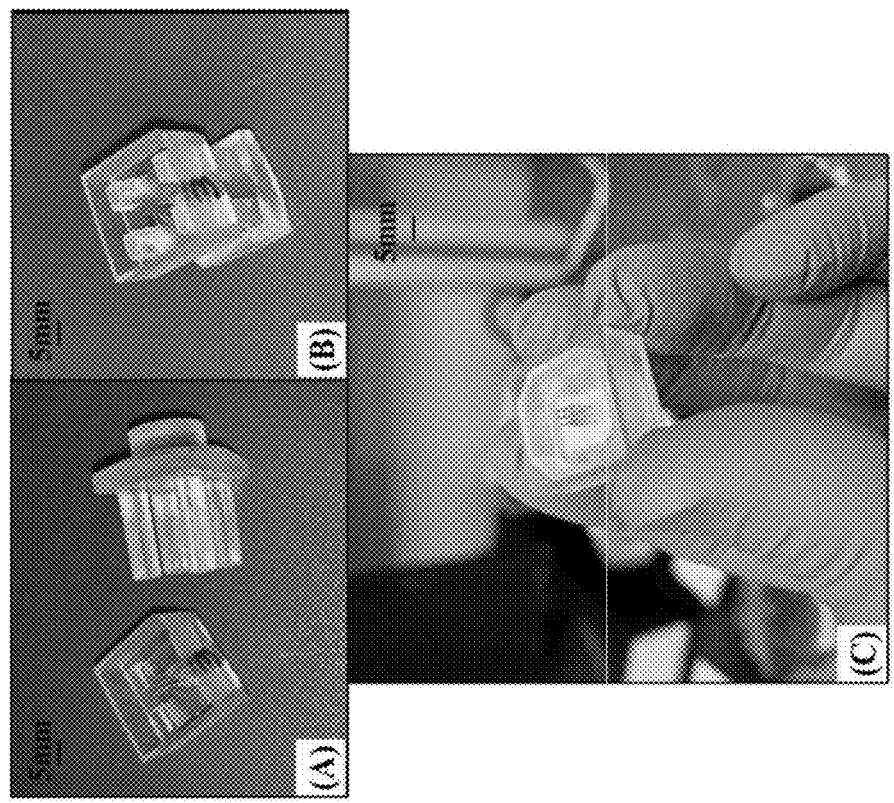
FIG. 41: Version 3 Hypo-Rig. (A) Optical image of the rig, complete with dispensing needles, and a printed release press. (B) Optical image of the full Version 3 Hypo-Rig assembly. (C) Optical image of the rig with a fitted culture well inserted.
Figure 42:
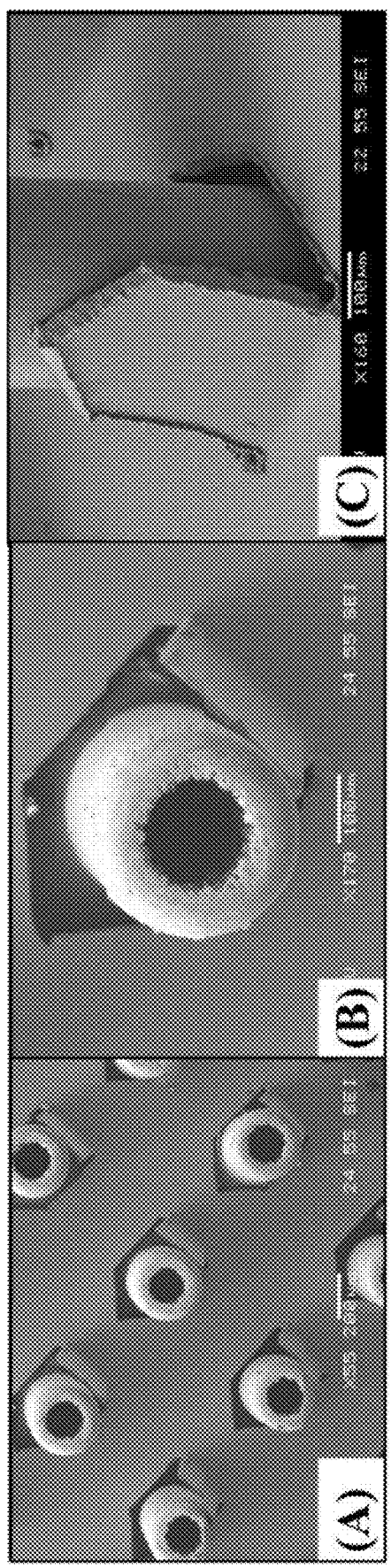
FIG. 42: SEM images of the Version 3 Hypo-Rig. (A) SEM image of the array during transition, demonstrating the same precise alignment as in previous versions. (B) SEM image close-up of one needle from (A). (C) SEM image of an alternate view of the needle from (B).

FIG. 41 demonstrates the fully printed and assembled version 3 Hypo-rig in a 3×3 conformation to work with the Modular MEA described in Example 4. Additional SEM images of the 2D to 3D transition process using this new Hypo-rig can be seen in FIG. 42.

The general concepts of this Example 5 will be further explained in reference to FIGS. 37 and 38. FIG. 38 shows a base support 100 that has secured therein an array of elongated bodies 101. The array of elongated bodies 101 (e.g. hypo-dermic needles, dispensing needles, or similar elongated structures having sufficient resilience to transition metal) is applied to a 2D planar metal substrate 102 into which cut-outs 103 have been made (FIG. 37) such that the material of the metal cut-outs 103 transition out of plane (orthogonal) to the 2D planar structure to form individual microneedles 105 as is shown in FIGS. 38B and C. After transitioning the metal cut-outs to form the microneedles 105, the array of elongated bodies 101 is removed from the planar substrate 102.

Example 6: Optical/Electrical Probe

Figure 43:
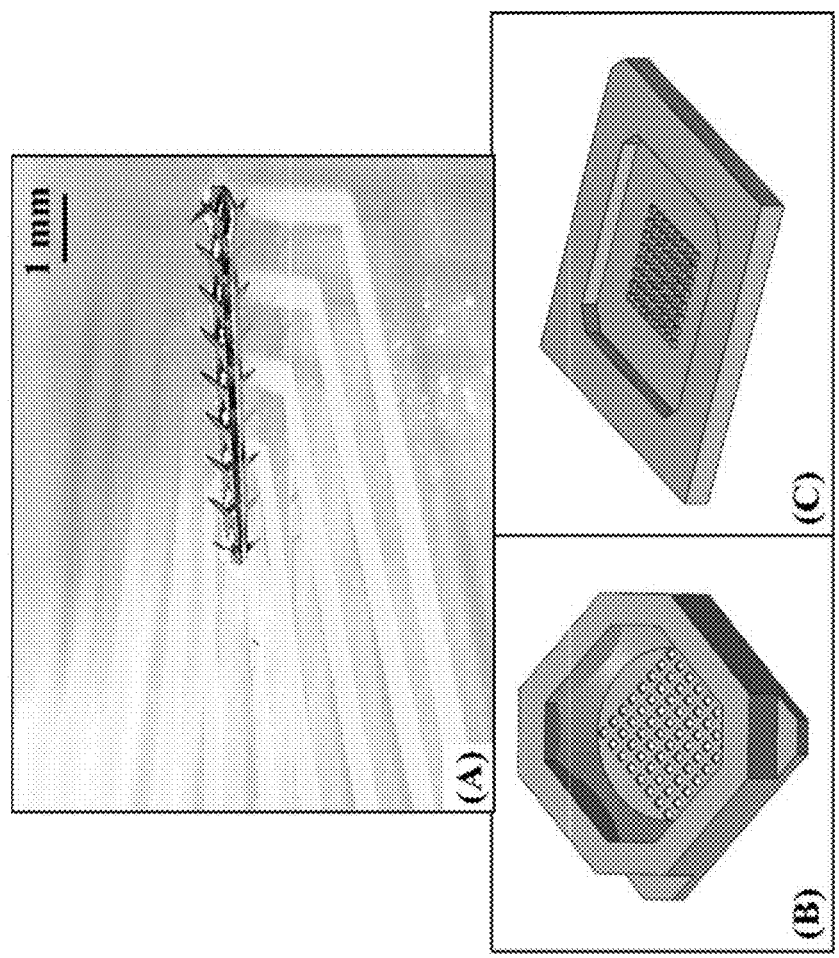
FIG. 43: Additional in vitro MEA process results. (A) Schematic design of the 8×8 Modular MEA culture well. (B) Schematic design for the 8×8 micro pillar substrate. The ease of scalability in this design is due to the use of DLP 3D printing. (C) Optical image of a 2D to 3D transitioned set of microneedle electrodes, arranged in a Nerve-on-a-chip compatible design. The strength of this approach is demonstrated through the substrate-agnostic nature of its fabrication.
Figure 44:
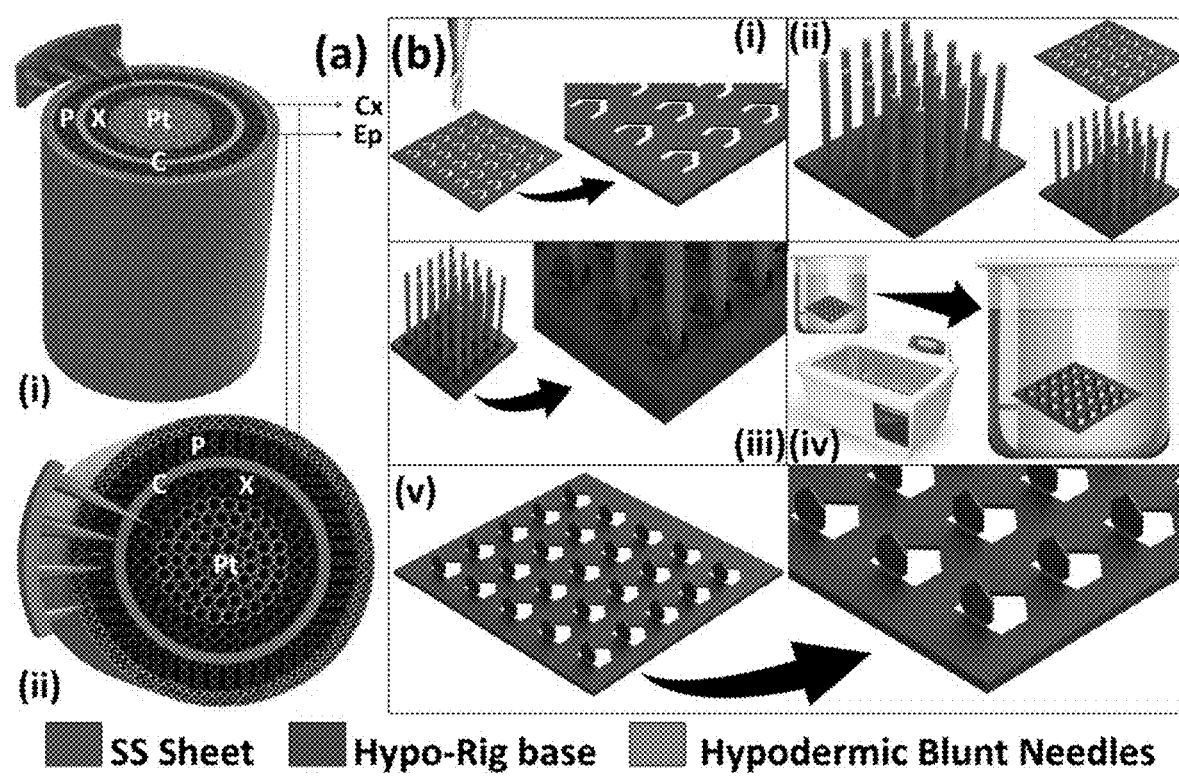
FIG. 44 (a) Concept schematic on the usage of μMMNs for controlled penetration in plant stem tissue. (i) Isometric view and (ii) Top view. (b) Fabrication technique used to realize the μMMNs using 'Makerspace Microfabrication'. (i) Micromilling onto planar stainless steel substrate (SS); (ii) Aligning the SS substrate with the Hypo-Rig; (iii) Transitioning the μMMNs out of plane; (iv) Acid pickling with sonication to remove debris from micromilling and (v) Final μMMNs ready for testing.

To demonstrate the substrate and design independence of this MEA fabrication approach, a "nerve-on-a-chip" [25] optical/electrical probing compatible design was developed (FIG. 43$a$). The development of such a device entails glass packaging substrates of similar dimensions as above (24 mm width by 24 mm length, and 1 mm thick). The glass substrate was washed in an alkaline bath (10% KOH (wt %), and 90% DI water (wt %)) for 1 hour prior to metal deposition. To define the metal layer atop this glass substrate, titanium (Ti; 4N5 purity pellets) and gold (Au; 5N purity pellets) (Kurt J. Lesker, USA) were deposited by electron-beam (Ebeam) evaporation (Thermionics Laboratory Inc., USA) through a micromilled stencil mask on the glass substrate. The Ti and Au layers were deposited at a vacuum of 5.0×10-6 Torr, with layer thicknesses of 30 nm (Ti) and 150 nm (Au). Deposition rates for this process were 2.0 nm/s (Ti) and 5.0 nm/s (Au) respectively. The metal 3D microelectrodes were fabricated using laser micromachining as described in Section 4.5.2 and attached atop the metal landing pads of the glass chip using the conductive silver epoxy.

An 8×8 3D printed modular design was fabricated and assembled using the same microfabrication and packaging strategy as was discussed in Example 4. FIG. 43 ($b$ & $c$) contain the schematic of the modified culture well and substrate for this design.

A powerful combination of additive 3D printing, metal microfabrication and an in situ characterization technique can be applied to the creation of custom in vitro MEA platforms. The benefit that makerspace environments impart to this fabrication process flow is the ability to rapidly prototype and iterate, as demonstrated with the Examples provided above. Even within the final Modular MEA design, the many successive sub-iterations would not have been an accessible method of engineering the design in a traditional fabrication environment. The scalability of the laser micromachining, metal microfabrication technique employed is also impactful in the further creation of a higher density 8×8 design. Further, the in situ characterization during device fabrication allows for precise control over the final electrode recording site size, even after N-P Pt electroplating.

Example 7: Precision Vascular Delivery of Agrochemicals with Micromilled Microneedles (μMMNs)

Introduction

Food production is one of the main challenges to be overcome in the future. By 2050, world population is expected to reach 9 billion inhabitants and food production must be doubled in the next 30 years[1]. Efficient delivery of agrochemicals, such as fertilizers and pesticides, is one of the key elements for improved food productivity and security. Current developments in this area include fertigation, in-field sensors for automatized sprays based on plant demand, use of drones, etc.[2]. Nevertheless, smart agriculture technologies are expensive and require large investments. Another challenge on efficient delivery of agrochemicals is related to systemic delivery throughout the plant. Foliar spray[3] and soil drench[4] are the standard methods to apply agrochemicals such as pesticides and fertilizers. However, these application methods have some negative environmental implications such agrochemical run-off and adverse effect on the soil microbiome. Furthermore only a small percentage of applied agrochemical is actually up taken by the plants[5].

Scientific reports suggest that plants are capable of sensing their environment in some way similar to humans and other animals[6]. Recent discoveries indicate that the very root apex of a plant has the capacity to detect twenty (20) different physical and chemical parameters including gravity, light, magnetic field, pathogens and more6. Therefore, devices and mechanisms used to treat infections and diseases in humans can potentially be translated for treatment of plants as well. Microneedle (MN) based treatment of plants infected with pathogens is one such overlapping application arena. MNs were first envisioned as painless drug delivery devices decades ago, but with the accelerated evolution of microfabrication techniques, MNs have transitioned from academic laboratories to pharmaceutical companies as commercially available, off-the-shelf products[7,8]. Hollow and solid microneedle technologies are commonly used in drug delivery systems[7]. MNs offer patient-friendly delivery solutions for vaccines or difficult-to-deliver biologics particularly for hypodermic needle-phobic patients[8]. Such transdermal MNs work by creating micron sized pores in the skin to enhance delivery of the drug across the skin without stimulating the pain nerves demonstrating the immense degree of control that can be obtained with dermal penetration utilizing properly designed MNs. Such controlled penetration to specific depths is of special importance for agricultural applications as systemic pathogens in plants reside in hard to reach areas of the plant tissue9. As examples, bacterium such as Candidatus Liberibacter asiaticus, responsible for Huanglongbing (HLB, also known as citrus greening)[10] reside in the phloem tissue of the plant while Xylella fastidiosa, responsible for citrus variegated chlorosis reside in the xylem tissue[11]. As a result, custom fabricated MNs would allow for disease and site-specific vascular treatment of plants using agrochemicals. Additionally, they can address concerns relating to the systemic delivery of agrochemicals while conserving the loss of the applied agrochemical with increased rainfastness.

Figure 45:
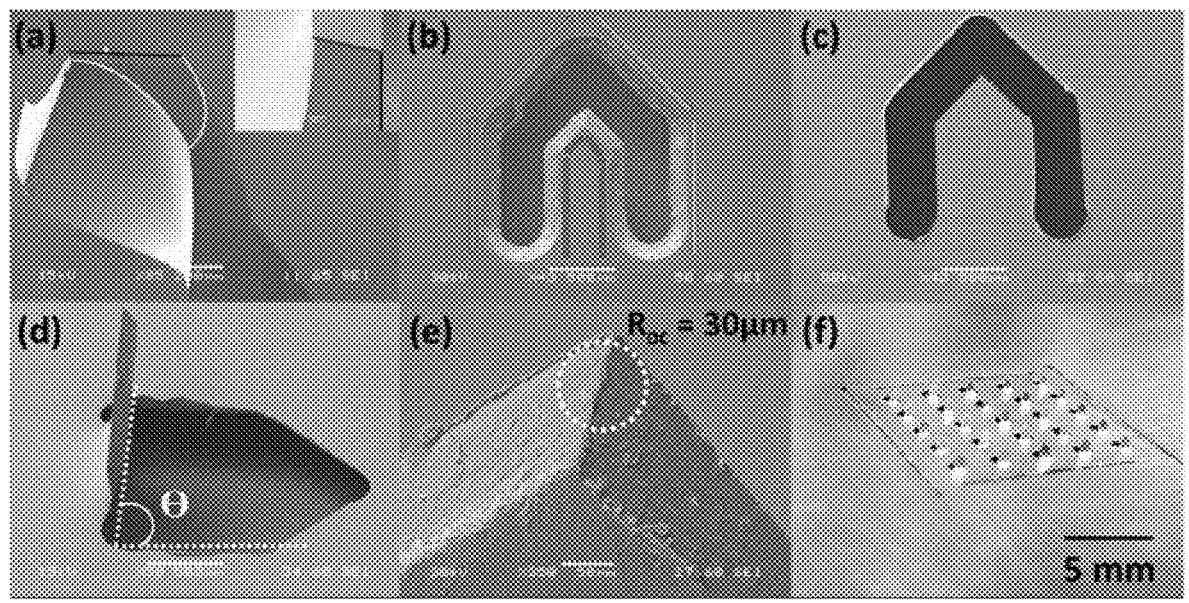
FIG. 45 (a) SEM image of the micromilling pointed tool; (b) top side of the SS sheet after micromilling; (c) bottom side of the micromilled SS sheet; (d) SEM of the near perpendicular alignment of a single μMMN to the horizontal; (e) Tip of a single μMMN depicting a radius of curvature of 30 μm and (f) Photomicrograph of the 5×5 array of μMMNs.

In recent years there has been a gradual transformation in the micromachining of biological microdevices such as MNs[12]. Traditional cleanroom-based microfabrication approaches are being replaced by non-conventional techniques outside the cleanroom which allows for the use of a different tool-set while offering a much larger material palette along with rapid fabrication timeframes, design modifications on-the-fly, cost effective, and scalable fabrication. The authors have previously introduced the concept of and demonstrated the use of 'Makerspace Microfabrication'[13,14] for fabricating MNs deployed in transdermal drug delivery applications. These MNs were fabricated using micro-stereo lithography (μSLA), an additive manufacturing technique. Such MNs are appropriate for penetrating soft tissue like skin having an Ultimate Tensile Strength (UTS) of ~40 MPa since commercially available 3D printed materials can have an UTS only as high as 65 MPa[15,16]. However, for penetrating trees, the UTS of the material used in MN fabrication needs to be an order of magnitude higher (~500 MPa[17]), making a material such as stainless steel (SS) with similar tensile strengths (UTS of ~500 MPa[18]), a much better choice. SS based MNs can be fabricated using micromilling which is a subtractive manufacturing method[19,20] that creates microscale features utilizing microscale cutting tools to remove unwanted bulk material to define the desired geometry. The microscale cutting tools vary in diameter from 5 to 400 μm and have edge radius that varies from 1 to 10 μm[21].

In this Example, provided is the use of micromilled microneedles (μMMNs) for vascular delivery of agrochemicals to highly specific and targeted sites of the plant tissue. With optimized micromilling conditions, a μMMN array is fabricated in a 5×5 configuration on a planar stainless steel sheet having a thickness of ~100 μm in the traditional "Washington Monument" design. The microneedles are subsequently transitioned into the third dimension using a customized Hypo-Rig[22] to have the 3D μMMN array. The microneedles have a base width of ~500 μm and a height of ~500 μm. These minimally invasive stainless steel microneedles were used to create controlled and targeted punctures in the stem of citrus saplings and a model therapeutic cargo of a zinc-based antimicrobial called Zinkicide™23 was delivered and the study of the uptake mechanism into the leaves, stem and roots was performed. Atomic Absorption Spectroscopy (AAS) reveals that the saplings punctured with μMMNs and treated with the model therapeutic showed significant increase in the cargo uptake in the leaves (6×) and the stem (7.5×) when compared to the control sample. Scanning Electron Microscopy (SEM) imaging reveals that the μMMNs are capable of making targeted site-specific punctures to the xylem and the phloem regions. The micromilling process has been extended to demonstrate its ability to realize intricate geometries such as "Tridents" and "Triangular Tip" toward applications to fully grown trees. Both a 6×6 array of "trident" shaped mesoneedles having a height of 4 mm and a 19×20 array of "triangular tip" mesoneedles with similar dimensions are demonstrated in this work. Owing to the flexible nature of the ~100 μm SS substrate, this design was affixed on a roller and tested in field conditions to demonstrate scalability and real-world deployment of our methods. This precision transport of agrochemicals to specific target sites provides a low-cost alternative to delivery of agrochemicals through the stem, directly to the plant tissue, without impacting soil beneficial microorganisms and with no risk of rainfastness.

Schematic of the concept of μMMNs for controlled, site-specific penetration in plant stem tissue is shown in FIG. 44(*a*): (*i*) and (*ii*). It is proposed that tuning of the MN geometry for controlled puncture of specific target sapling/tree sites such as the xylem and phloem is possible. FIG. 44(*b*):(*i-v*)) depict the fabrication technique used to realize the μMMNs using 'Makerspace Microfabrication'. The micromilling tool is used to engrave the "Washington Monument" design onto a planar SS substrate [FIG. 44(*b:i*)]. The engraving entails selective removal of the SS material. A custom fabricated Hypo-Rig is used to transition the "Washington Monument" structures out-of-plane resulting in the formation of 3D μMMNs [FIG. 44(*b*):(*ii*) and (*iii*)]. Acid pickling[24] of the μMMNs allows for not only the removal of unwanted debris from the micromilling process but also potential sharpening of the μMMN tips [FIG. 44(*b*):(*iv*)] to construct final μMMNs ready for testing [FIG. 44(*b*):(*v*)].

Results and Discussion

FIG. 45(*a*) shows the SEM image of the micromilling pointed tool used to engrave patterns onto the SS substrate. As observed in the image, the micromilling tool has a web thickness (marked in red) of 40 μm[25]. The two (2) cutting lips (or flutes) of the tool and the landing of the tool are highlighted in blue and yellow respectively. The number of flutes is one of the governing factors while calculating the chip load on the tool. With a feed rate of 3 mm/s and a spindle frequency of 1000 Hz, the chip load on the tool is ~1.5 μm as Chip load=(Feed rate)/(Frequency×Number of flutes)[26]. The values of the spindle frequency and feed rate were chosen so that the chip load would remain under 10% of the minimum tool dimension (40 μm web thickness in this case). A close-up SEM of the pointed tip is also shown in the inset of the same figure. FIG. 45(*b*) depicts the top side of a micromilled SS sheet. It is observed that the micromilling tool indents a characteristic 45° slant face on the top side as the micromilling tool has a 90° pointed tip with respect to the SS surface. As the milling tool rotates in a clockwise direction and moves with respect to the substrate while etching the desired geometry, the edges of the entire needle (eventually the 3D geometry) are defined by the down-milling (highlighted in magenta in FIG. 45(*b*)) while the in-plane geometry is defined by up-milling (highlighted in green in FIG. 45(*b*))[27]. An optimized feed-rate of 3 mm/s allows for both the edges to be smooth as observed in the figure. Higher feed rates would translate to a greater chip load which leads to more wear and eventually breakage of the tool while lower feed rates would lead to poor device finish, inefficient cycle times, and premature tool wear due to increased tool indentation as a result of chip thinning[28]. Some debris from the micromilling process can adhere to the substrate as also shown in the figure but this material is removed by an acid pickling process[24]. FIG. 45(*c*) shows the bottom side of the micromilled SS sheet which only shows the cut-out of the "Washington Monument" design and not the milled features as this side was not exposed to the milling tool. FIG. 45(*d*) depicts the μMMN after the planar micromilled cut-out has been transitioned out of plane. The μMMN have a very tight angular distribution (θ) of 85.2° [FIG. S1(a)] with the horizontal which shows the efficiency of the Hypo-Rig for transitioning the μMMNs out-of-plane as observed in FIG. 45(d,f). The transition process proceeds from the bottom face of the SS sheet which naturally lends the μMMNs to have a sharp slicing tip as observed in FIG. 45(e). The radius of curvature (ROC) of the slicing tip is found to be ~30 μm. FIG. 45(f) shows the optical photomicrograph of the μMMNs fabricated in a 5×5 configuration. The microneedles were designed to have a base width of ~500 μm and a height of ~500 μm. It is observed that the μMMN dimension closely matches the design dimension. A box plot of N=25 μMMNs (one μMMN patch) showing variation in height and base width is shown in FIG. S1(b,c). A mean height and width of 550.6 μm and 466.8 μm is obtained for the μMMNs respectively. A standard deviation of 42.57 μm and 31.83 μm from the design values (both less than 10%) is obtained for the height and base width respectively due to the micromilling process.

Figure 46:
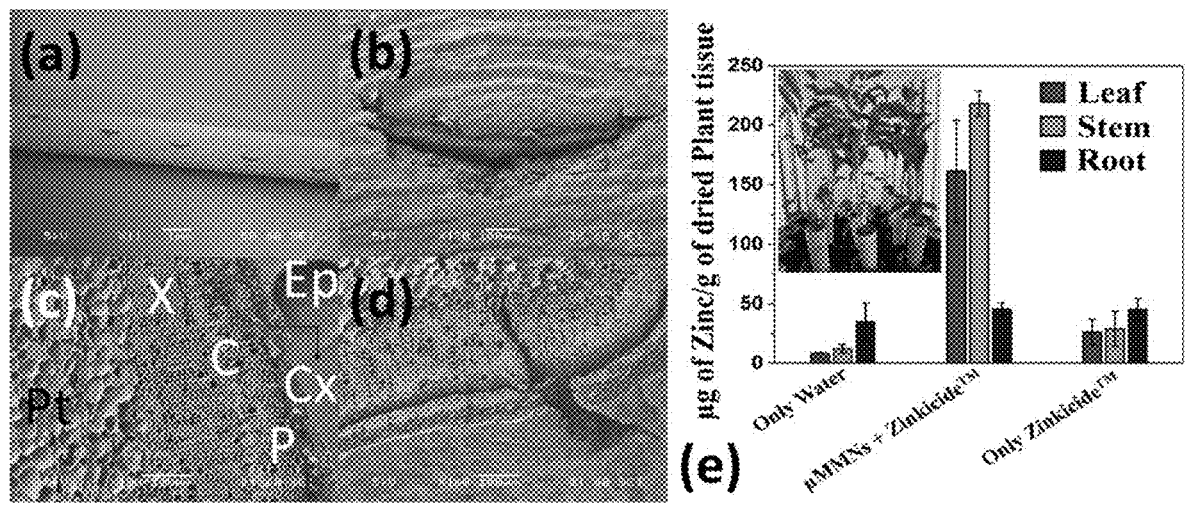
FIG. 46 (a) SEM image (5×1 penetrations) of the puncture caused by the μMMN onto the stem of a citrus seedlings with (b) showing a close-up SEM image of one puncture site; (c) SEM image showing the cross-section of the unpunctured stem with the epidermis (Ep), cortex (Cx), phloem (P), cambium (C), xylem (X) and the pith (Pt); (d) SEM image of the cross-section of a stem at one of the μMMN puncture sites; (e) Bar graph of the of the Zn concentration in the leaves, stem and roots after the application of the therapeutic cargo of Zinkicide™. Inset shows the plants in the growth chamber, after puncturing with the μMMN and sealing the plastic container containing the therapeutic cargo around the puncture site.

FIG. 46(a) shows a SEM image of the puncture caused by a μMMN onto the stem of the citrus seedlings. An array of one entire row is (5×1) is clearly observed in the image and two such punctures were made on either side of the stem for delivery of the therapeutic cargo. Having a μMMN patch in a 5×5 configuration allows it to be used with saplings in various stages of growth. As the sapling matures, the stem increases in diameter and the entire patch would conform onto the surface of the stem. In this work we used saplings that are 12 months-old and had a maximum stem diameter of 2.5 mm. Therefore, penetrations of two entire rows (5×1) on either side of the sapling stem (10 penetrations in total) was attempted to study the effect of the therapeutic cargo. The design featuring a patch in a 5×5 configuration provides for redundancy in case of puncture failures. A box plot of N=10 puncture sites showing variation in puncture width is depicted in FIG. 49(d). It is observed that the width of the puncture is 683 μm with a standard deviation of 35.22 μm. The larger width of the puncture site is attributed to the shear forces during the puncture of the stem with the μMMNs. FIG. 46(b) shows the close-up SEM image of one puncture site caused by a single μMMN. The sharpness of the μMMNs causes stem penetration with minimal damage to neighboring tissue. This would allow for the stem to heal rapidly post-treatment resulting in reduced secondary infections from the wounds caused by the μMMN.

Figure 49:
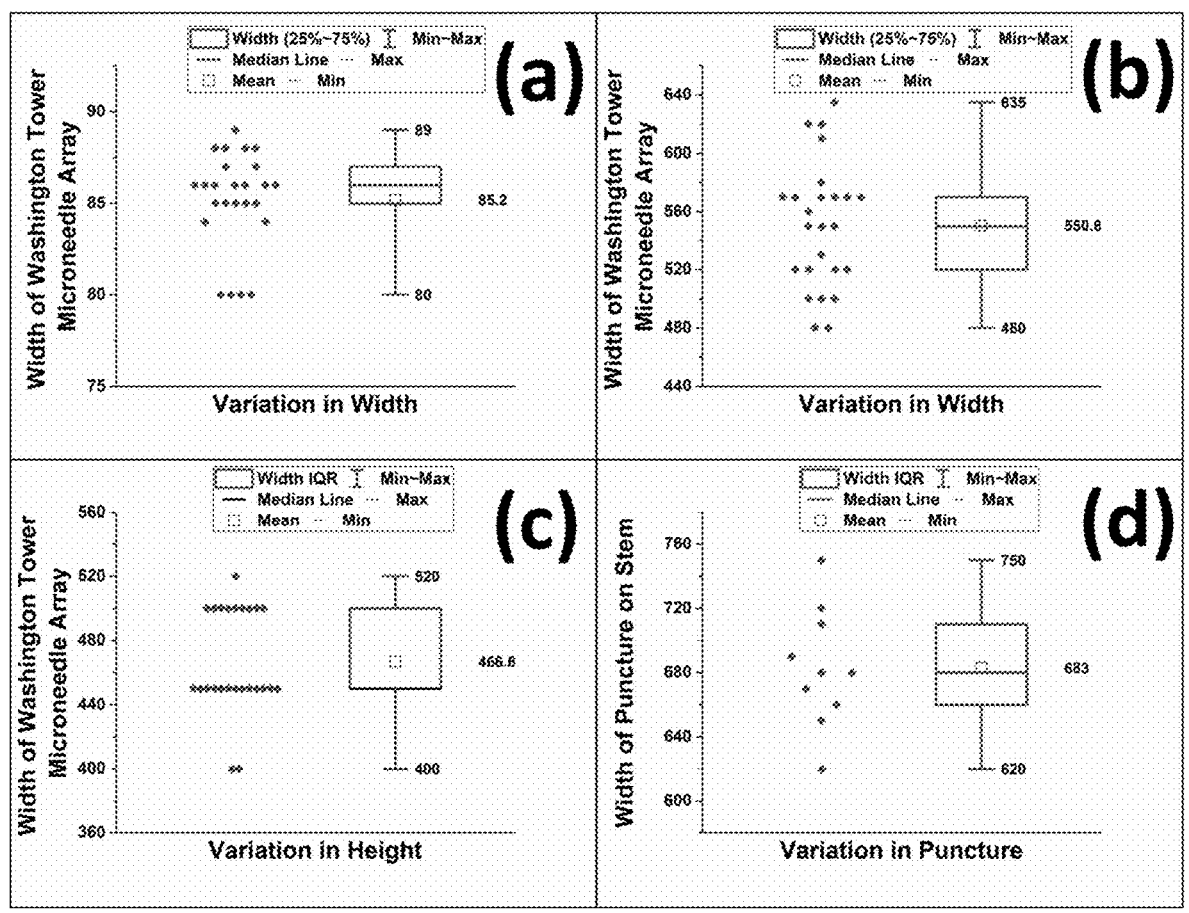
FIG. 49: (a) Tight angular distribution (θ) of 85.2° with the horizontal which shows the efficiency of the Hypo-Rig in transitioning the micro and mesoneedles out of plane. A box plot of N=25 μMMNs showing variation in base (b) width and (c) height after micromilling. (d) A box plot of N=10 puncture sites showing variation in puncture width.
Figure 50:
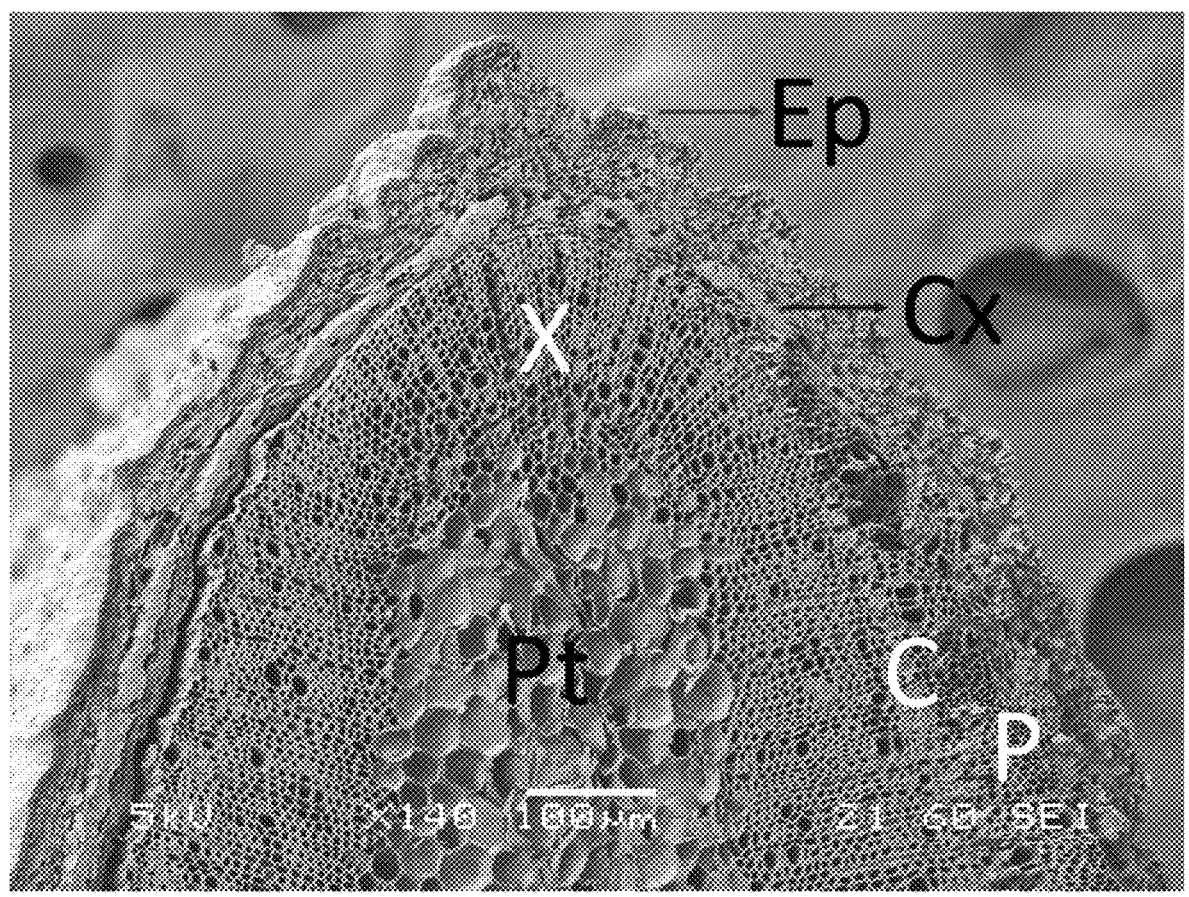
FIG. 50: SEM image showing the cross-section of the un-punctured stem with the epidermis (Ep), cortex (Cx), phloem (P), cambium (C), xylem (X) and the pith (Pt)

FIG. 46(c) shows the enlarged cross-section of the un-punctured stem with the epidermis (Ep), cortex (Cx), phloem (P), cambium (C), xylem (X) and the pith (Pt) highlighted. A lower magnification image of the cross-section of the un-punctured stem is shown in FIG. 49. The seedlings used in our experiments were 12 months old and the resulting the vascular tissue are in their developing stages and are therefore not very distinct but can clearly be differentiated under the SEM. FIG. 46(d) shows a cross-sectional SEM of the stem at one of the μMMN puncture sites. The μMMN is clearly observed to puncture the Ep and Cx layers and create a pathway through the vascular tissue. FIG. 46(e) depicts the bar graph of the AAS results quantifying the Zn concentration in the leaves, stem and roots after the application of the therapeutic cargo consisting of Zinkicide™. The inset shows the plants in the growth chamber, after puncturing with the μMMNs and sealing the plastic container containing the therapeutic cargo around the puncture site. The zinc content in stem and leaves after microneedle treatment is observed to have increased 7.5× and 6× respectively with respect to the control. These results suggest the transport of zinc through the xylem tissue. As the xylem allows for unidirectional transport (upward), the increase in zinc concentration in the leaves and stem and not the roots portrays μMMN penetration into the xylem region. This is also corroborated with the SEM images [FIG. 46(d)]. No significant increase of zinc content in the roots after treatment with Zinkicide™ indicates that the μMMN did not selectively penetrate the phloem tissue, which is multidirectional and would have allowed for zinc transport to the roots as well. However, with custom design of the μMMNs, accounting for the thickness of the stem and depth of the phloem tissue, micromilling-based rapid realization of MNs would make it possible to selectively deliver to the phloem region. This would be of significant importance as it would be an effective means of treating Huanglongbing (HLB, also known as citrus greening) which is a systemic bacterial disease caused by Candidatus Liberibacter asiaticus (CLas) which requires bactericides (including currently used antibiotics) to be delivered directly to the phloem of the plants.

Figure 47:
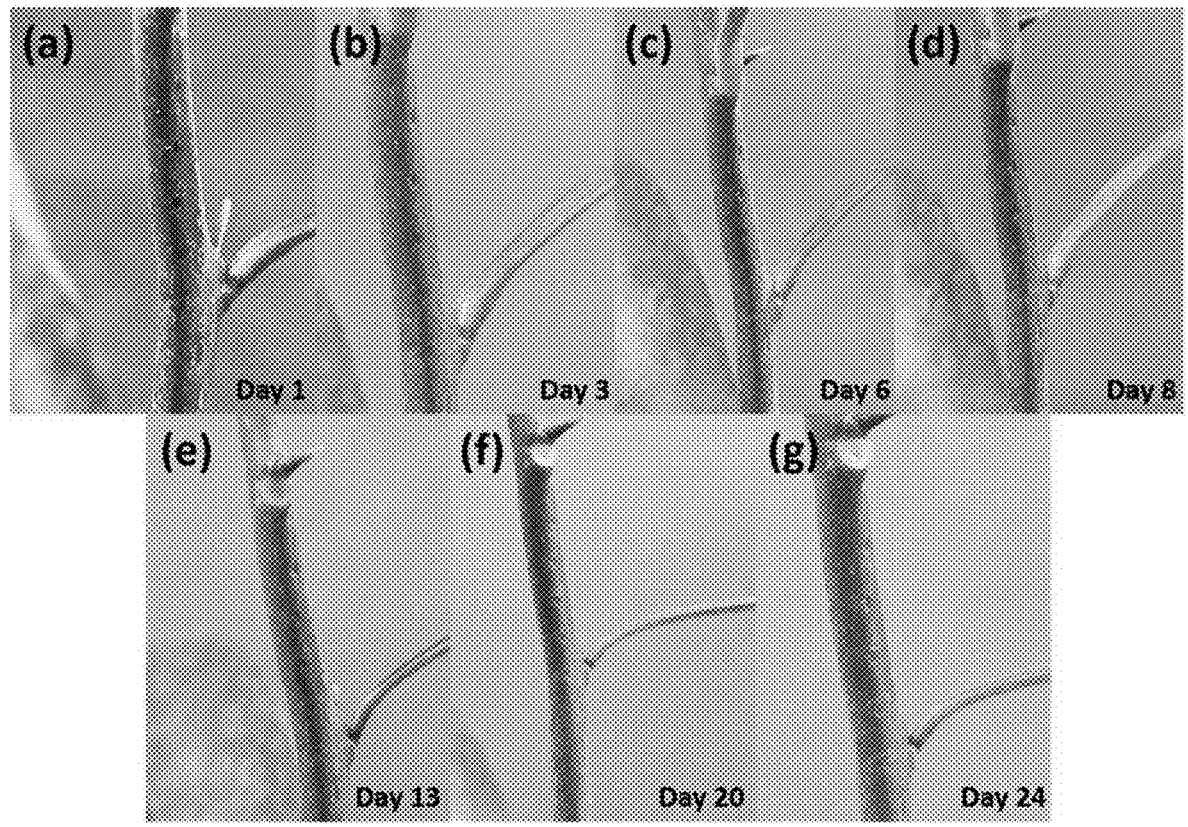
FIG. 47 (a-g) Self-healing of the puncture sites caused by the μMMNs from Day 1 (day of puncture), Day 3 (healing of wound) and Day 24 (scar healing).
Figure 51:
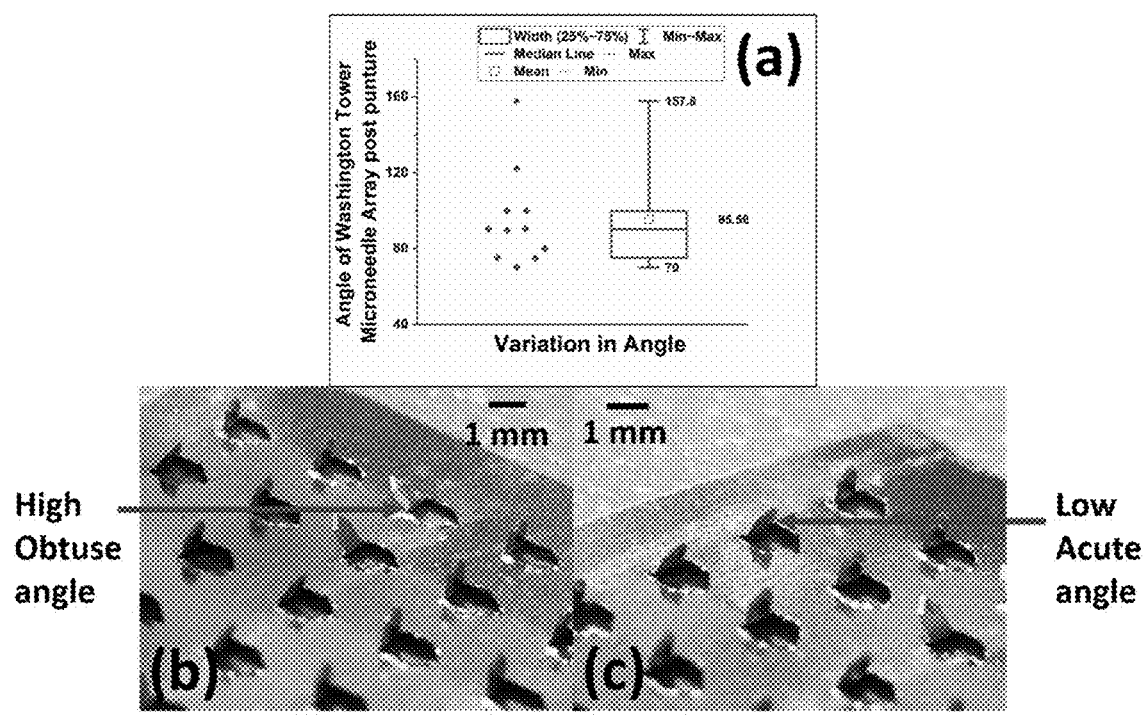
FIG. 51: (a) Box plot of N=10 μMMNs which have been bent from their original positon after pressing onto the stem surface. Representative images of μMMNs dislocated to (b) higher values of obtuse angles or (c) low values of acute angles after pressing into plant stem.

FIG. 47(a-g) shows the self-healing of the puncture sites caused by the μMMNs. As evident from the figure, the puncture sites start self-healing in a few days, with visible scars from the wound starting to close up. Based on the visual observation, most wounds disappear by Day 24 even though the outline of the scar is noticeable. FIG. 51(a) shows the box plot of N=10 μMMNs post puncture sites onto the citrus stem after M=6 cycles. Each cycle corresponds to the penetration of the two 5×1 arrays onto the citrus stem. It is interesting to note here that the μMMNs do not break after repeated, successful citrus stem penetration affirming the hypothesis that the large Young's Modulus of SS can overcome the UTS of citrus stems. However, as observed in the figure, if the μMMNs are not correctly aligned to the plant stem, they may be bent at other angles after treatment. Although the flexible nature of the SS substrate allows for the μMMNs to conform to the curvature of citrus stem, obtuse or acute angles can result due to improper alignment as observed in FIG. 51(b,c) respectively. Nonetheless, a majority of the μMMNs maintain fabricated angular distribution and as a result the array can be reused multiple times.

Figure 52:
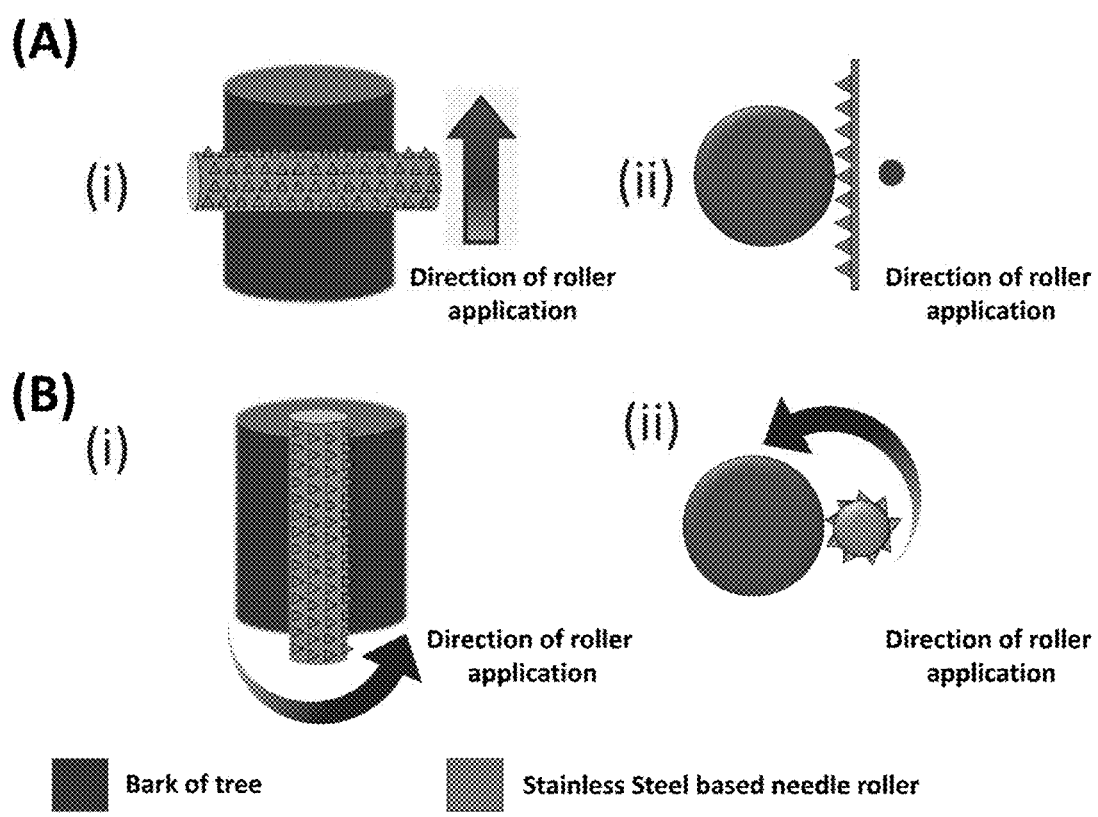
FIG. 52: (A) (i) 3D Schematic of the needle roller being applied vertically, (ii) top-view showing the axis of the roller based needle array being a tangent to the axis of the cylindrical tree trunk while moving into the plane. (B) (i) 3D Schematic of the needle roller being applied horizontally, (ii) top-view showing the roller needle array engaging with the full surface of the tree trunk as it is being rolled.

To demonstrate scalable micro-manufacturing and field-readiness of the μMMNs in a real-world setting outside the lab, two distinct aspects of the reported technology are highlighted and demonstrated. First, the versatility of the micromilling process to realize any customized design and second preliminary results of a roller array based applicator system used on a citrus tree are demonstrated in this paper. FIG. 48(a) shows a photomicrograph of an array of 6×6 trident shaped mesoneedles having a height of ~4 mm suitable for use on fully grown trees. FIG. 48(b) shows the intricate details of the "Trident" in the microscale achieved using micromilling allowing for meso to micro-scale precision of the micromilling technology. Unlike the "Washington Monument" design, the "Trident" design may also allow for extraction of plant tissue with the two pointed edges on either side during withdrawal of the needles allowing for potential plant histology and will allow for better anchoring during penetration. FIG. 48(c) shows an array of 19×20 mesoneedles with a "Triangular tip" design with the microscale features highlighted in the SEM image of the mesoneedle in FIG. 48(d). As the ~100 μm SS substrate is flexible as seen in FIG. 48(c), it can conformally attach to practical applicator systems. The 19×20 array which spans a total area of (95×110) mm2 is affixed onto a commercial paint roller applicator system [FIG. 48(e)] and applied to the bark of a citrus tree parallel to the ground surface as observed in FIG. 48(f). This horizontal approach of rolling the applicator ensures that an entire row of needles (N=19) on the roller engage completely with the cylindrical trunk of the tree. As the axis of the two cylinders, namely the tree trunk and the paint roller applicator are parallel to one another the applicator can roll over the cylindrical conformity of the tree trunk. In this case, an entire row of needles on the roller make full contact with the bark of the tree. This ensures (a) sufficient punctures on the bark of the tree in one rolling action and (b) the entire force applied during the rolling action being transferred to the tips of the needles in one entire row and does not lead to premature roller failure in specific sections of the device. A schematic illustrating the difference between the horizontal approach and vertical approach of the applicator is provided in FIG. 52.

Figure 48:
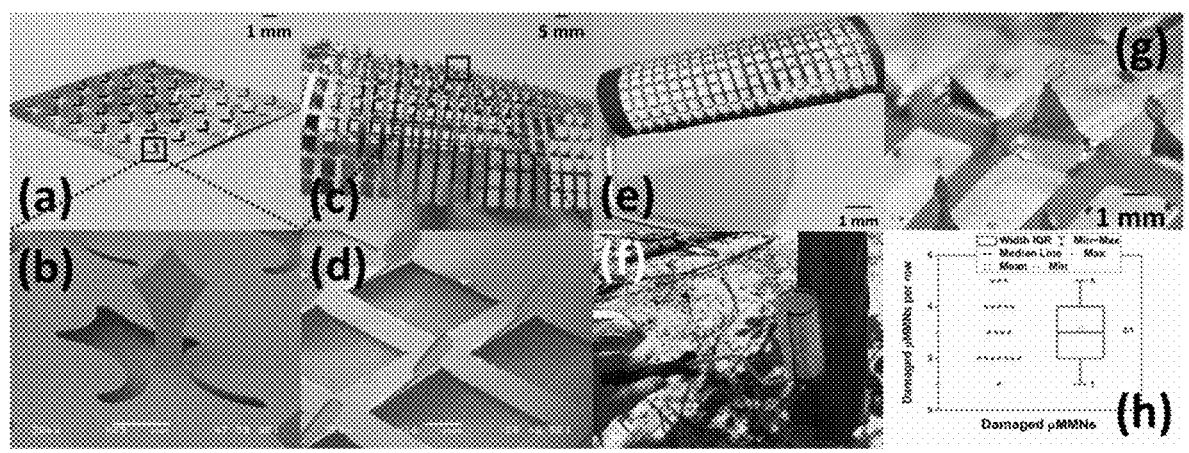
FIG. 48 (a) Photomicrograph of an array of 6×6 trident shaped mesoneedles with (b) SEM image showing the intricate design features; (c) Photomicrograph of an array of 19×20 mesoneedles with a triangular tip with the (d) SEM image of the mesoneedle showing the triangular tip; (e) Photomicrograph of a 19×20 mesoneedle array affixed onto a paint roller with (f) field testing of the applicator system; (g) Optical micrograph of damaged needles in the paint roller based applicator system after rolling onto the tree and (h) number of mesoneedles which were bent after N=5 rolling operations performed by the applicator system.

The microneedle array successfully penetrated the tree in the regions where the microneedle loaded applicator system was delivered. To assess the reliability of the µMMN applicator system in the demonstrated "in field application", a failure analysis of the microneedles was carried out to study the efficacy of the system. As already discussed earlier, alignment of the applicator to the tree bark has to be accounted for since all MNs do not align in such a system. These needles were marked as damaged as observed in FIG. 48(*g*). FIG. 48(*h*) shows the number of mesoneedles which were bent in non-vertical angles after N=5 applications using the system. It is observed that the total number of needles which were bent due to five successive applications was ~15% demonstrating an average of three (3) mesoneedles per row.

Conclusions

Micromilled microneedles (µMMNs) for precision vascular delivery of agrochemicals has been successfully demonstrated. It is seen that makerspace enabled microfabrication allows for rapid, robust, benchtop based, cost-effective fabrication for realization of micro and mesoscale needles which can target specific portions of the vascular bundle of plants, for example xylem and the phloem. µMMNs are able to penetrate plant tissue in a minimally invasive fashion enabling rapid self-healing. A 7.5× increase in the uptake of a therapeutic cargo of Zinkicide™ shows the effectiveness of the puncture and vascular delivery mechanisms. Further, the methodology is capable of rapid and cost-effective customization and has been demonstrated to be scalable and field-ready with an array of 19×20 mesoneedles having reliable behavior in real world settings.

Methods

µMMN Fabrication

For the fabrication of the 5×5 MN array with "Washington Monument" design (chip size: 17 mm×17 mm), a 90-degree T-4 Mill Tool (T-Tech, Peachtree Corners, GA, USA) was spun at 60,000 rpm (1000 Hz) in a T-Tech QC-J5 Quick Circuit Prototyping Systems to cut into a stainless steel sheet (~100 µm thick; Trinity Brand Industries, Countryside, IL, USA). The feed rate was maintained at 3 mm/sec with a depth of cut ≥100 µm. A custom Hypo-Rig was used to transition the µMMNs out of plane. This technology is essentially a custom designed array of hypodermic needles having the exact pitch and number of the MNs that need to be transitioned out-of-plane. The entire array is housed on a custom designed jig with matching dimensions and assembled using proprietary techniques. The 3D µMMNs were subsequently pickled in a solution of DI Water (80 wt %): 70% HNO3 (11 wt %): 49% HF (9 wt %) at 50° C. for 3 minutes with sonication. The 6×6 "Trident" (chip size: 40 mm×40 mm) and 19×20 (chip size: 95 mm×110 mm) "Triangular" MN arrays were micromilled with the same parameters using the appropriate CAD design. For the µMMN roller, the ~100 µm SS sheet with the µMMN array was affixed onto a paint roller frame with adhesive tape after removing the fabric on the paint roller.

µMMN Puncture Onto Saplings and Trees

Citrus seedlings (Citrus reshini, Cleopatra mandarin) approximately 12 month-old were used as plant model for the experiments (6 plants per group). The stem area (about 10 cm above the soil) was indented with µMMNs and covered with plastic container containing 2 mL of each of the therapeutic cargo (5000 ppm Zinkicide™) or Deionized (DI) water. The stem area of the microneedle control group of plant was only covered with the treatments, without being indented by the µMMNs. Plants were kept in a growth chamber (Panasonic Environmental Test Chamber, MLR-352H, Japan) for 48 hours. Controlled day/night cycling temperature, light intensity and humidity were used to simulate the weather conditions of Florida during summer (temperature >26.67° C. with a relative humidity of 60-80%). For the mesoneedle array applicator system affixed onto a paint roller, a six-year-old 'Ruby Red' grapefruit tree located in the Estes Citrus Inc. grove at Vero Beach, Indian River County, Florida was treated in Mar. 14, 2018. The trunk was rolled about 15 cm above the soil level. The rolling direction was parallel to the ground level.

Atomic Absorption Spectroscopy

The plants were taken out from the growth chamber and the plastic container was detached and plants were removed from soil. They were washed and separated in parts (roots, leaves and stem) before being dried in an oven at 45° C. for 24 hours. Dry parts were weighed, ground and digested with nitric acid, hydrochloric acid and hydrogen peroxide (EPA recommended methodology) 30 for Zn content analysis by Atomic Absorption Spectroscopy using Perkin Elmer Analyst 400 Atomic Absorption Spectrometer (Perkin Elmer, MA, USA). The results were plotted by microgram (µg) of metallic Zn per gram (g) of dried plant material.

SEM Imaging

Scanning electron microscope (SEM) imaging of the µMMN array was performed using JSM 6480 (JEOL, Peabody, MA, USA). For plant tissue imaging, lyophilization of the samples was performed. To obtain a slow freezing rate, the stems were frozen at −12° C. for 24 hours. To prevent the samples from being disturbed when vacuum was introduced, the stems were placed in a freeze-drying container and covered with a polystyrene petri-dish with drilled holes to allow vapor to escape. The container was subsequently connected to a sample valve on the drying chamber of a 1 liter benchtop freeze-dry system (FreeZone, Labconco, Kansas City, Missouri). The samples were dried for 12 hours at a vacuum level of 0.033 mbar with a collector temperature of −40° C. After 12 hours, the dried samples were removed and ready to be imaged.

REFERENCES FOR EXAMPLE 7

1. Bruinsma, J. World Agriculture: Towards 2015/2030 An FAO Study (ed. Bruinsma, J.) 28 (Taylor and Francis group, 2017).
2. Shamshiri, R. R. et al. Research and development in agricultural robotics: A perspective of digital farming. International Journal of Agricultural and Biological Engineering 11, 1-14 (2018).
3. Jyung, W. & Wittwer, S. Foliar absorption—an active uptake process. American Journal of Botany 51, 437-444 (1964).
4. Gardener, B. B. M. & Fravel, D. R. Biological control of plant pathogens: research, commercialization, and application in the USA. Plant Health Progress 3, 17 (2002).

5. Pimentel, D. Amounts of pesticides reaching target pests: environmental impacts and ethics. Journal of Agricultural and environmental Ethics 8, 17-29 (1995).
6. PLANT, https://upliftconnect.com/plant-neurobiology-trees-humans/.
7. 3M, https://www.3m.com/3M/en_US/drug-delivery-systems-us/technologies/microneedle/hollow-needle/.
8. van der Maaden, K., Jiskoot, W. & Bouwstra, J. Microneedle technologies for (trans) dermal drug and vaccine delivery. J. Control. Release 161, 645-655 (2012).
9. Santra, S., Rajaraman, S., Lee, W. H., Yunjun, X. & Campos, M. G. N. (Google Patents, 2019).
10. Jagoueix, S., Bove, J.-M. & Garnier, M. The phloem-limited bacterium of greening disease of citrus is a member of the α subdivision of the Proteobacteria. International Journal of Systematic and Evolutionary Microbiology 44, 379-386 (1994).
11. Lacava, P., Araújo, W. L., Marcon, J., Maccheroni, W. Jr & Azevedo, J. L. D. Interaction between endophytic bacteria from citrus plants and the phytopathogenic bacteria Xylella fastidiosa, causal agent of citrus-variegated chlorosis. Letters in applied microbiology 39, 55-59 (2004).
12. Walsh, D. I. III, Kong, D. S., Murthy, S. K. & Carr, P. A. Enabling microfluidics: from clean rooms to makerspaces. Trends Biotechnol 35, 383-392 (2017).
13. Kundu, A., Ausaf, T. & Rajaraman, S. 3D Printing, Ink Casting and Micromachined Lamination (3D PICLμM): A Makerspace Approach to the Fabrication of Biological Microdevices. Micromachines 9, 85 (2018).
14. Kundu, A. et al. Optimization of makerspace microfabrication techniques and materials for the realization of planar, 3D printed microelectrode arrays in under four days. RSC Adv. 9, 8949-8963 (2019).
15. Resin, T. https://supportformlabs.com/s/article/Using-Tough-Resin?language=en_US.
16. PDF, F, https://formlabs.com/media/upload/XL-DataSheet.pdf.
17. Bamboo, https://www.ehow.com/info_12150266_tensile-strength-bamboo-vs-wood.html.
18. 200, S, http://asm.matweb.com/search/SpecificMaterial.asp?bassnum=mq304a.
19. Popov, K., Dimov, S., Ivanov, A., Pham, D. T. & Gandarias, E. New tool-workpiece setting up technology for micro-milling. The International Journal of Advanced Manufacturing Technology 47, 21-27 (2010).
20. Guckenberger, D. J., de Groot, T. E., Wan, A. M., Beebe, D. J. & Young, E. W. Micromilling: a method for ultra-rapid prototyping of plastic microfluidic devices. Lab Chip 15, 2364-2378 (2015).
21. PDF, M, https://pdfs.semanticscholar.org/ee92/1b63870d58bb261dcc19bd5e200b86784819.pdf.
22. Didier, C. M. & Swaminathan Rajaraman, A. K. Facile, packaging substrate-agnostic, microfabrication and Assembly of scalable 3D metal microelectrode arrays for in vitro Organ-on-a-chip and cellular disease modeling. The 20th International Conference on Solid-State Sensors, Actuators and Microsystems Solid-State Sensors, Actuators and Microsystems Transducers 2019—EUROSENSORS XXXIII (2019).
23. Johnson, E. Zinkicide: A novel therapeutic zinc particulate based formulation for preventing citrus canker and HLB, Project No. 907, University of Florida. CRDF Comprehensive Final Report (2016).
24. Covino, B., Scalera, J., Driscoll, T. & Carter, J. Dissolution behavior of 304 stainless steel in. HNO 3/HF mixtures. Metallurgical Transactions A 17, 137-149 (1986).
25. Shatla, M. & Altan, T. Analytical modeling of drilling and ball end milling. Journal of Materials Processing Technology 98, 125-133 (2000).
26. Diaz, N., Redelsheimer, E. & Dornfeld, D. In Glocalized solutions for sustainability in manufacturing 263-267 (Springer, 2011).
27. Dweiri, F., Al-Jarrah, M. & Al-Wedyan, H. Fuzzy surface roughness modeling of CNC down milling of Alumic-79. Journal of Materials Processing Technology 133, 266-275 (2003).
28. Thinning, C. http://www.helicaltool.com/secure/Content/Documents/Tech_ChipThinning.pdf.
29. Erner, Y. & Shomer, I. Morphology and anatomy of stems and pedicels of spring flush shoots associated with Citrus fruit set. Annals of Botany 78, 537-545 (1996).
30. Agency, U. E. P. Method 7000B—Flame atomic absorption spectrophotometry (2007).

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

What is claimed is:

1. A method of fabricating micromilled microneedles from a planar substrate, the method comprising
micromilling a plurality of cut-outs onto the planar substrate, the cut-outs each comprising a cut electrode portion and an intact region that is intact with the planar sheet; and
transitioning material at the plurality of the cut-outs such that the material extends orthogonal to the planar substrate,
wherein the transitioning step comprises
(i) aligning an array of transition-effecting structures with the planar substrate such that individual transition-effecting structures are oriented with the plurality of cut-outs, the array of transition-effecting structures comprising elongated bodies; and
(ii) inserting the array of transition-effecting structures through the planar substrate to bend the cut electrode portion of the cut-outs about the intact region such that the cut electrode portion is out of plane with the planar substrate.

2. The method of claim 1, wherein the planar substrate is metal.

3. The method of claim 2, wherein the metal is stainless steel.

4. The method of claim 1, further comprising subjecting the substrate and microneedles to an acid and sonication to remove debris caused by the micromilling.

5. The method of any of claim 1, wherein the microneedles are at a greater than 60, 70 or 80 degree angle respective to the planar substrate.

6. The method of claim 1, wherein the transition-effecting structures are hypodermic needles or dispensing needles.

7. A substrate comprising a plurality of microneedles produced by the method of claim 1.

8. The method of claim 1, wherein the array of transition effecting structures comprises a hollow needle array comprising
   a base; and
   a plurality of hollow needles secured to the base and extending orthogonally from the base.

9. The method of claim 8, wherein the base is produced by 3-D printing.

10. A 3D MEA platform comprising
    a 3D printed substrate;
    one or more conductive traces deposited on the 3D printed substrate;
    one or more microneedles disposed suprajacent to the one or more traces, wherein the microneedles are comprised of cut-outs in a planar substrate, the cut-outs each comprising a cut electrode portion and an intact region with the cut electrode portion being bent about the intact region so as to be out of plane with the planar substrate;
    an insulation layer disposed on to the microneedles; and
    a culture well disposed suprajacent to the insulation layer, wherein the microneedles protrude through the insulation layer into the culture well.

11. The 3D MEA platform of claim 10, wherein the substrate is comprised of a resin.

12. The 3D MEA platform of claim 11, wherein the resin comprises 3DP.

13. The 3D MEA platform of any of claim 10, wherein the one or more microneedles are aligned on top of the one or more traces.

14. The 3D MEA platform of any of claim 10, wherein the substrate layer comprises one or more recesses into which traces of the trace layer are deposited.

\* \* \* \* \*